United States Patent [19]

Onishi et al.

[11] Patent Number: 5,449,902
[45] Date of Patent: Sep. 12, 1995

[54] APPARATUS FOR DIRECTLY COUPLING ANALYTICAL COLUMN WITH MASS SPECTROMETER

[75] Inventors: Kouzi Onishi, Nishinomiya; Norio Tada, Ikeda; Yoshinobu Yoshimura, Ibaraki; Yoshiaki Kato, Mito, all of Japan

[73] Assignees: Hitachi, Ltd., Tokyo; Takeda Chemical Industries, Ltd., Osaka, both of Japan

[21] Appl. No.: 168,884

[22] Filed: Dec. 16, 1993

[30] Foreign Application Priority Data

Dec. 17, 1992 [JP] Japan .................................. 4-336496
Jan. 8, 1993 [JP] Japan .................................. 5-001626

[51] Int. Cl.⁶ .................................................. H01J 49/04
[52] U.S. Cl. ................................... 250/288; 250/281; 250/282
[58] Field of Search .................. 250/288 A, 288, 282, 250/281

[56] References Cited

U.S. PATENT DOCUMENTS 4,866,270 9/1989 Hall et al. ...................... 250/288 A
5,117,109 5/1992 Asakawa et al. ................ 250/288 A

OTHER PUBLICATIONS

Biological and Environmental Mass Spectrometry, vol. 16, pp. 393–397 (1988).
Biological Mass Spectrometry, vol. 21, pp. 305–314 (1992).

*Primary Examiner*—Jack I. Berman
*Attorney, Agent, or Firm*—Kenyon & Kenyon

[57] ABSTRACT

An apparatus for directly connecting an analytical column and a mass spectrometer comprising a fixed member having at least four holes which respectively introduce washing solution, eluate containing a component eluted from the analytical column, desalting solution and eluent for eluting the component, and a movable member rotated with respect to an axis having at least four tubes around the axis and mounting the four trapping columns, whereby the trapping columns are respectively washed, trapped, desalted and eluted in parallel. Furthermore, a common trapping column may be used instead of the four trapping columns by controlling the apparatus with four analytical modes.

20 Claims, 41 Drawing Sheets

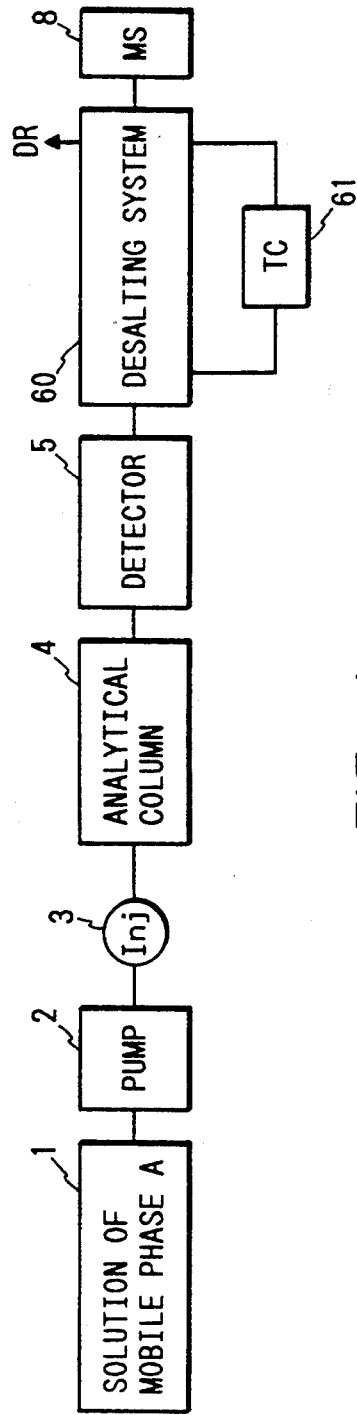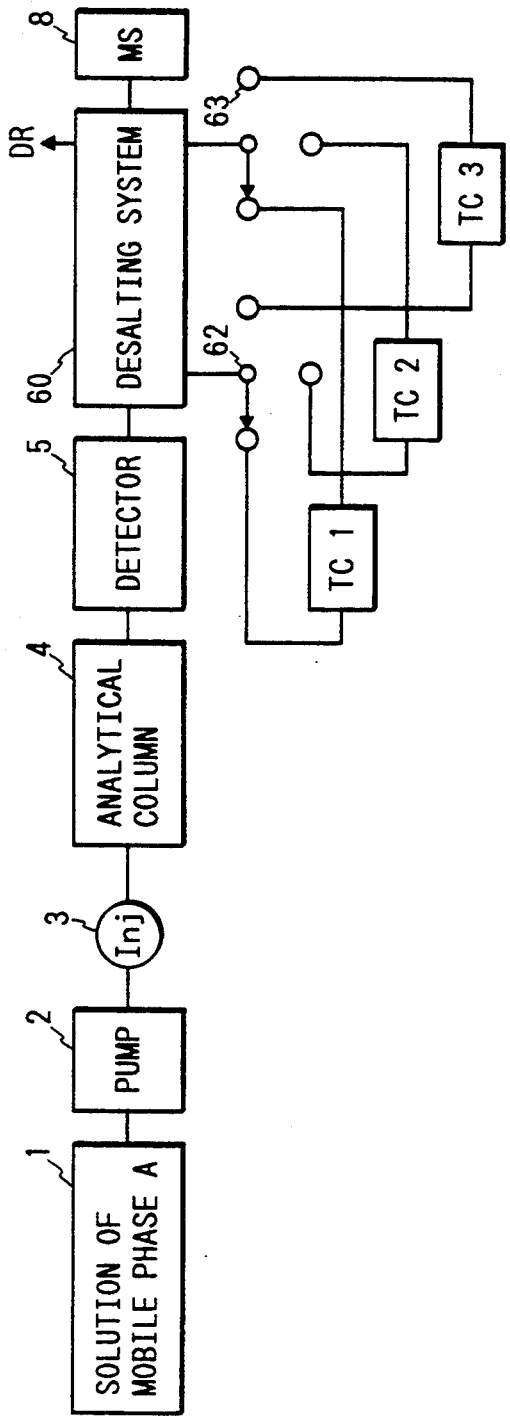

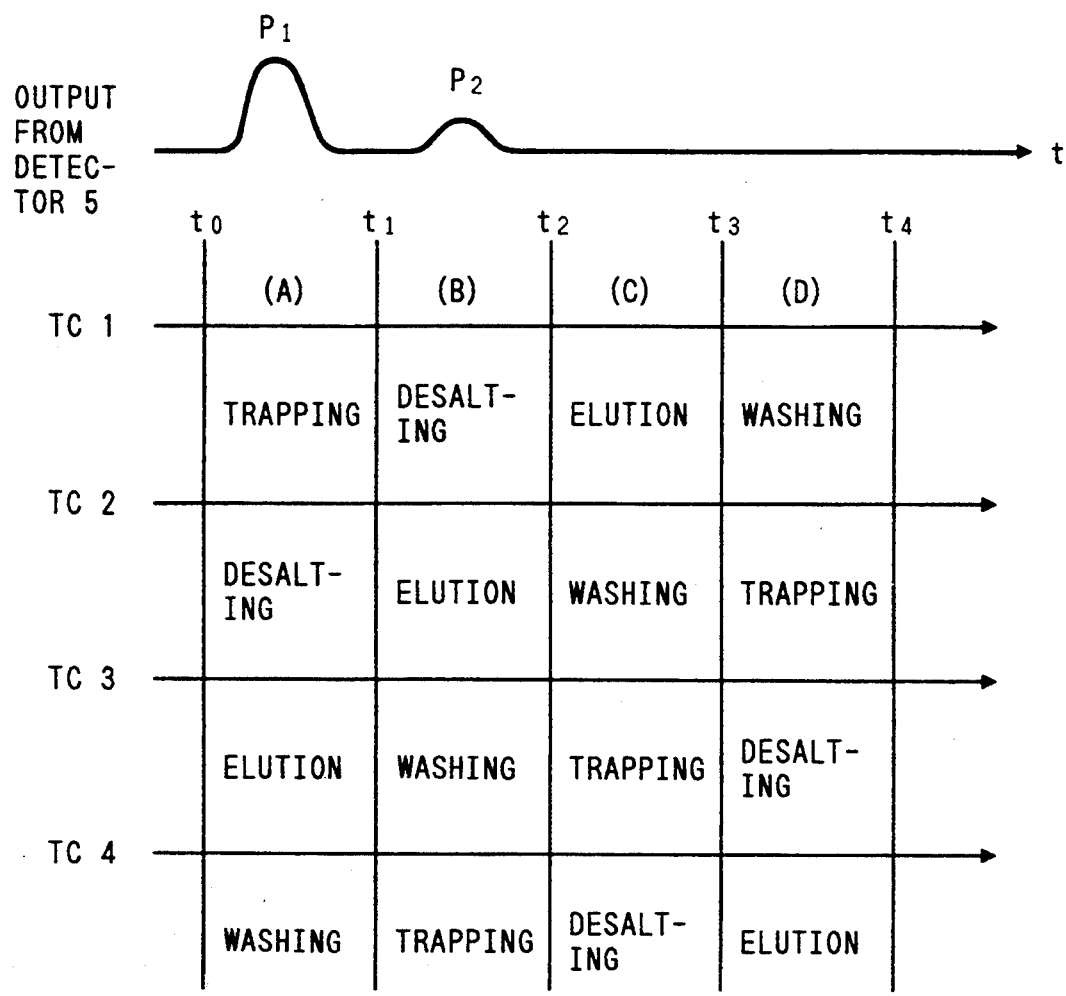
FIG. 10
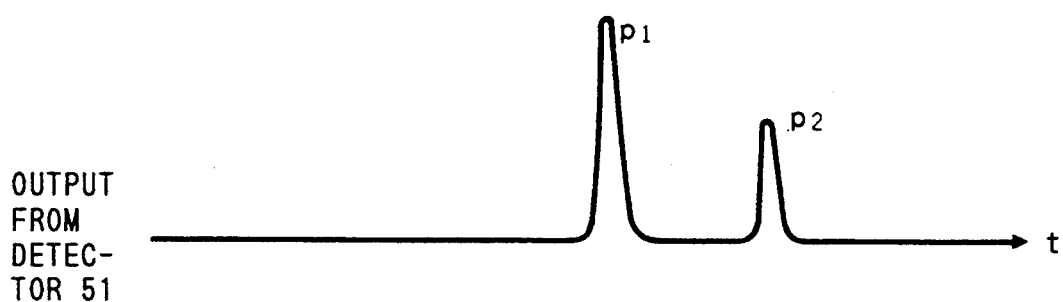

FIG. 14

| | $t_0$ | $t_1$ | $t_2$ | $t_3$ | $t_4$ | $t_5$ | $t_6$ |
|---|---|---|---|---|---|---|---|
| TC 1 | TRAPPING | DESALTING | DESALTING | ELUTION | WASHING | WASHING | |
| TC 2 | DESALTING | DESALTING | ELUTION | WASHING | WASHING | TRAPPING | |
| TC 3 | DESALTING | ELUTION | WASHING | WASHING | TRAPPING | DESALTING | |
| TC 4 | ELUTION | WASHING | WASHING | TRAPPING | DESALTING | DESALTING | |
| TC 5 | WASHING | WASHING | TRAPPING | DESALTING | DESALTING | ELUTION | |
| TC 6 | WASHING | TRAPPING | DESALTING | DESALTING | ELUTION | WASHING | |

APPARATUS FOR DIRECTLY COUPLING ANALYTICAL COLUMN WITH MASS SPECTROMETER

BACKGROUND OF THE INVENTION

The present invention relates to an apparatus for directly coupling an analytical column used in a liquid chromatograph (herein after called LC) or a flow injection analysis device (herein after called FIA) with a mass spectrometer (herein after called MS), and more particularly to an apparatus for successively trapping a component of interest in a trapping column, washing (desalting) the trapped component of interest, eluting the trapped component of interest and washing the trapping column so as to transmit an eluate from the trapping column to MS.

In the conventional LC/MS apparatus, the trapping, the washing(desalting), the eluting and the washing processes are performed as shown in FIG. 24.

That is, liquid sample is injected in solution of a mobile phase A through an injection port by using a micro-syringe and is separated according to components of the sample by analytical column 4.

Then, an eluate A eluted from the analytical column 4 is diluted with solution of mobile phase B and is transmitted to a trapping column TC, whereby a component of interest for analysis in the eluate is trapped by the column TC and others in the eluate are wasted to a drain DR.

After that, as shown in a central position of FIG. 24, only the solution of mobile phase B such as water, flows in the column TC so as to wash, that is, desalt the column TC and eluate D from the column TC are wasted to the drain DR.

Then, as shown in a right-hand side of FIG. 24, solution of the mobile phase C such as organic solvent etc. flows in the column TC, whereby the components of interest trapped in the column TC are successively eluted as eluate C and are transmitted to the mass spectrometer so as to analyze mass of the components.

Meanings of the words frequently used hereinafter will be explained as shown in a following table.

| Words | Meanings |
| --- | --- |
| solution of the mobile phase A | eluent for being analyzed by LC |
| eluate A | eluate eluted from the analytical column 4 |
| solution of the mobile phase B | diluent for diluting the eluate A, and washing (desalting) liquid for the trapping column TC |
| confluenced eluate | mixed solution of the eluate A and the mobile phases B |
| eluate B | the confluenced eluate eluted from the TC |
| eluate D | the solution of the mobile phase B eluted from the TC after washing (desalting) |
| solution of the mobile phase C | eluent for eluting the components of interest trapped in the TC |
| eluate C | eluate containing the components of interest eluted from the TC |

Sample solutions analyzed by the LC or FIA generally contain nonvolatile ionic substances, and solutions containing nonvolatile salt and buffer substances are widely used as the solution of the mobile phase A.

When such nonvolatile substances are used solely in LC or FIA, few problems arise.

In the case of an LC/MS, the LC/MS may be used to sample gas, liquid, ions etc., which must pass through a small aperture or a capillary tube into a high vacuum region. In such a situation, the nonvolatile substances may be deposited around the small aperture or inside of the capillary tube, so that deposits clog them. Therefore, this problem has prevented the use of mobile phases containing nonvolatile substances in LC/MS apparatuses.

The Japanese laid-open Patents Nos. 3-175355(1991), 62-138753(1987) and 62-19758(1987) show an apparatus which traps component of analyte in a trapping column, the components of interest are washed (desalted) with solution of the mobile phase B, and the components of interest are eluted with a solution of the mobile phase C in order to solve the above problem.

FIG. 3 shows a block diagram of a conventional system for washing, desalting, trapping and eluting the components of interest as shown in the above Japanese laid-open Patent.

Numeral 1 shows a solvent of the mobile phase A containing the nonvolatile buffer which is transmitted by a pump 2, and a sample solution is injected through a sample injection port 3 by a micro-syringe. The sample solution is separated according to the components thereof in a analytical column by the solvent of the mobile phase A so as to successively elute from the analytical column and to be detected by a detector 5.

Then, eluate A from the analytical column 4 is desalted by a desalting system 60. Desalting process in the desalting system 60 is performed by changing the flow path using a plurality of valves.

At first, after trapping the components of interest in a trapping column 61, the components of interest are washed, that is, are desalted with the solution of the mobile phase B such as water. Then, the component of analyte is eluted by the solution of mobile phase C which does not contain nonvolatile substance and is transmitted to a mass spectrometer 8 or a fraction collector.

In the system shown in FIG. 3, there is a problem as that the component being desalted may be analyzed, but other components contained in the sample are wasted to the drain DR and are not analyzed.

Further, FIG. 4 shows a system having a plurality of trapping columns TC1, TC2, TC3 which are used by successively collecting eluate from analytical column 4. This is accomplished by exchanging trapping columns by change-over valves 62, 63 in order to analyze multiple successive components of interest.

That is, the trapping columns TC1, TC2, TC3 are changed over when the components of interest eluted from a analytical column 4 are detected and thereby successively trapping the components of interest. After every column finishes trapping the components, the valves 62, 63 are changed over again, and the trapped components of interest are desalted, then eluted by the solution of the mobile phase C and transmitted to a mass spectrometer 8 or a fraction collector.

Further, a system using only one trapping column with a plurality of sampling loops was proposed.

In the conventional system as shown in FIG. 3, the component of analyte trapped in the trapping column is desalted and eluted when measuring the sample solution with LC, and therefore, it is needed for the trapping columns to be pretreated before every measurement of the liquid sample.

In order to analyze one objective component, it takes a time T as follows;

T={measuring time by LC+desalting and eluting time+analyzing time by the MS+pretreating time of TC}

Therefore, it takes so much time for analysis that it is difficult to perform it quickly and automatically.

Further, in order to analyze one component of interest in the conventional system as shown in FIG. 4, it takes a time T as follows;

T={measuring time by LC+desalting and eluting time+analyzing time by the MS+(pretreating time of TC) (number of components of interest trapped in TC)}

Therefore, more time for analysis is needed when the number of the components of interest is more than number of the TC. The analysis by the LC as above is performed by using the solution of the mobile phase A for nonvolatile substance, but the system becomes more complicated and more expensive in the following cases;

(1) The solution of mobile phase used for the analysis contains volatile substances.
(2) An analysis means is used which does not need separation by analytical column.
(3) The MS needs a means for preventing an introduction of the components of non-interest.

SUMMARY OF THE INVENTION

The present invention overcomes the above-mentioned problems of the conventional analytical methods.

An object of the present invention is attained by providing a device described as follows:

(a) At least one fixed member and a movable member which is rotated with respect to an axis and is slidable to and connected to a fixed member.
(b) The fixed member has at least four output holes therein.
(c) The movable member has four tubes around the axis and mounts at least four trapping columns respectively connected to the tubes, thereby the tubes are slidable and change over the holes so as to successively connect to the tubes.
(d) The four output holes are respectively connected to the trapping columns so as to perform four processes in parallel as follows;
(1) washing the trapping columns,
(2) trapping a component of interest contained in an eluate eluted from the analytical column,
(3) washing(desalting) the trapping columns, and
(4) eluting the component of interest from the i trapping columns.

Furthermore in the present invention, the movable member may mount more than five trapping columns thereon and at least two of the trapping columns are changed over so as to perform the same one of the process as the washing, the trapping of the component of interest, the washing(desalting) and the eluting of the component of interest.

Furthermore in the present invention, the movable member has a bypass tube between the tubes connected to the trapping columns for bypassing a drain from the fixed member.

Furthermore in the present invention, the flow direction of the solution of the mobile phase A and B in the trapping columns are opposite to the flow direction of the mobile phase C in the trapping columns.

As stated above, the present invention is characterized by having a movable member mounting thereon at least four trapping columns which are processed with four processing modes as (1) washing, (2) trapping, (3) washing (desalting), (4) eluting.

Further in the present invention, the above four processing modes are improved so as to use the same trapping columns in common by adding further modes processing thereto as follows;

(1) first analytical mode for washing the trapping column and introducing eluate from the analytical column to the mass spectrometer,
(2) second analytical mode for trapping a component of interest contained in eluate eluted from the analytical column by the trapping columns and washing the mass spectrometer,
(3) third analytical mode for eluting the component of interest trapped in the trapping columns and introducing the component of interest to the mass spectrometer, and
(4) fourth analytical mode for washing the trapping columns and the mass spectrometer, and for draining the eluate from analytical column.

BRIEF DESCRIPTION OF THE DRAWINGS

FIGS. 3 and 4 show examples of a block diagram of a conventional LC/MS system.

FIG. 10 shows a operating flow view of the LC/MS system in the present invention.

FIG. 14 shows a flow chart of the system shown in FIG. 13.

DETAILED DESCRIPTION OF THE PREFERRED EMBODIMENTS

Figure 5:
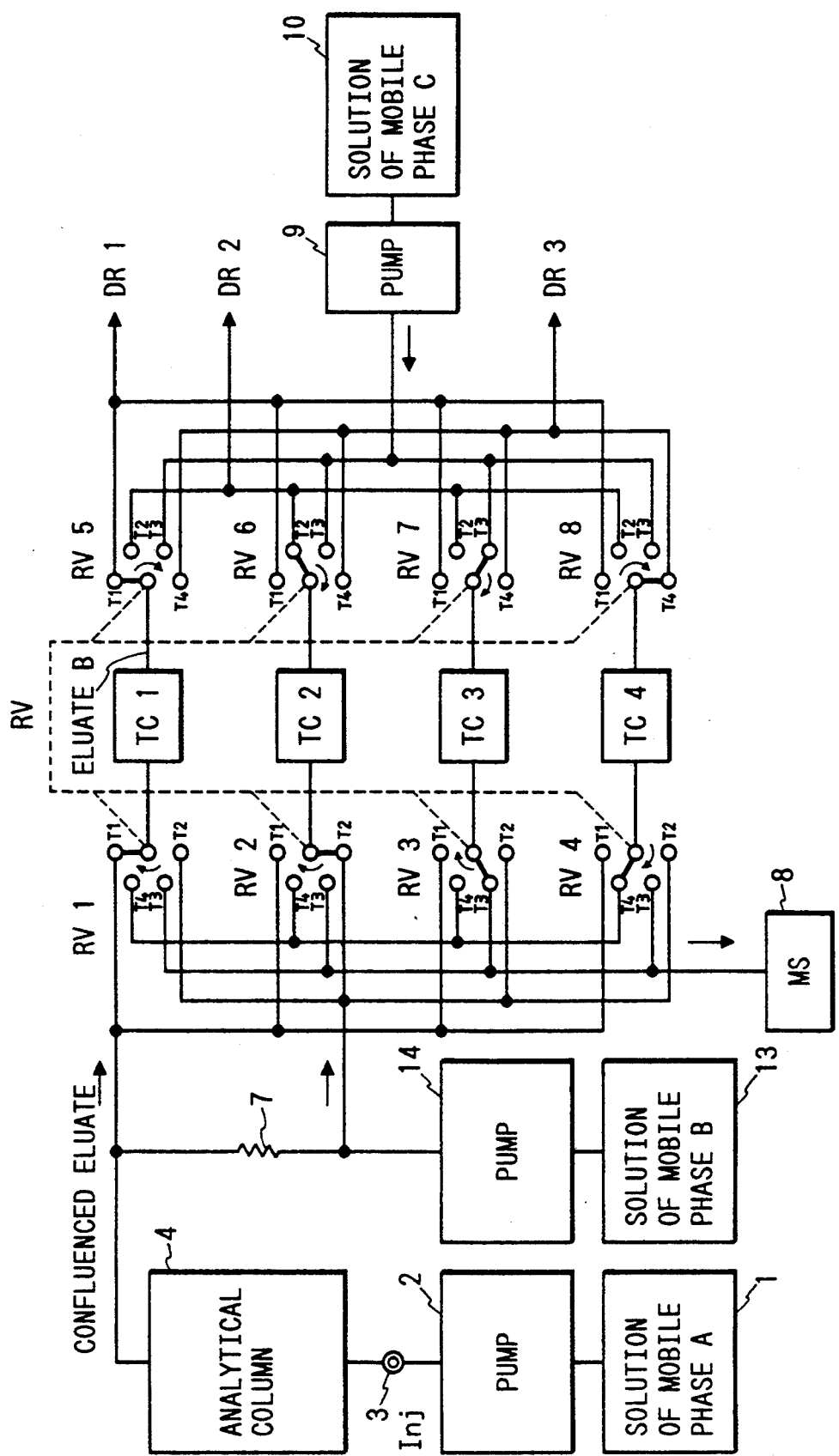
FIGS. 5 is a block diagram for showing a function which is a premise of the LC/MS system in the present invention.

FIG. 5 is a block diagram for showing the function of the LC/MS system including desalting process, from the introduction of eluate A to the recovery of eluate C in the present invention. The analytical processes of the washing, the trapping, the washing(desalting) and the eluting with respect to all components of the eluate A collected from an analytical column 4 are repeatedly performed by using the multiple trapping columns.

In the system shown in FIG. 5, the solution of the mobile phase A transmitted from the column 4 by a pump 2 is delivered by changing over four trapping columns TC1 to TC4 sequentially with eight rotational changing valves RV1 to RV8.

The four processing steps of washing, trapping, washing(desalting) and eluting are performed as follows; (First step)

All of the rotational change-over valves RV1 to RV8 are set as shown in FIG. 5 at first. The sample solution injected in the solution of the mobile phase A from a sample injection port 3 is separated according to the components in the sample by an analytical column 4. The solution 13 of the mobile phase B such as water is transmitted by a pump 14 through a path of a resistance column 7 and dilutes the eluate A so as to provide confluenced eluate.

The confluenced eluate flows into a trapping column TC1 through a rotational valve RV1 so as to trap the component of interest which is in the confluenced eluate. Eluate B then flows into a drain DR1 through a rotational valve RV5.

Simultaneously, the trapping column TC2 is washed with the solution 13 of the mobile phase B transmitted through the change-over valve RV2 by a pump 14, the trapping column TC3 is washed by the solution 10 of the mobile phased C transmitted through the change-over valve 7 by a pump 9, and the trapping column TC4 is washed with the branched solution 13 of the mobile phase B.

Under a condition as stated above, all of the rotational change-over valves are changed over so as to come into second step when the trapping column TC1 finishes to trap the components of interest. (Second step)

The rotational change-over valves are changed over 1 to 2 in RV1, 2 to 3 in RV2, 3 to 4 in RV3, 4 to 1 in RV4, 1 to 2 in RV5, 2 to 3 in RV6, 3 to 4 in RV7, and 4 to 1 in RV8.

Thereby, the trapping column TC1 is washed(desalted) by the solution 13 of the mobile phase B, and the trapping column TC3 is washed with the solution 13 of the mobile phase B.

The trapping column TC4 (changed over from the trapping column TC1) traps the next component of analyte in the confluenced eluate, and all of the rotational change-over valves are again changed over into third step when the trapping column TC4 finishes to trap the next components of interest. (Third step)

The rotational change-over valves are changed over 2 to 3 in RV1, 3 to 4 in RV2, 4 to 1 in RV3, 1 to 2 in RV4, 2 to 3 in RV5, 3 to 4 in RV6, 4 to 1 in RV7, and 1 to 2 in RV8.

Thereby, the trapping column TC1 is washed by the solution 10 of the mobile phase C, then the components of interest trapped on the first step are eluted and transmitted to a mass spectrometer 8 so as to provide a mass spectrum.

The trapping column TC2 is washed and desalted with the solution 13 of mobile phase B and the trapping column TC3 traps the third components of interest eluted from the analytical column 4. The trapping column TC4 is washed(desalted) with the solution 13 of the mobile phase B. All of the rotational change-over valves are changed over into fourth step. (Fourth step)

The rotational change-over valves are changed over 3 to 4 in RV1, 4 to 1 in RV2, 1 to 2 in RV3, 2 to 3 in RV4, 3 to 4 in RV5, 4 to 1 in RV6, 1 to 2 in RV7, and 2 to 3 in RV8.

Thereby, the trapping column TC4 is washed by the solution 10 of the mobile phase C, then the components of interest trapped in the second step are eluted and transmitted to a mass spectrometer 8 so as to provide a mass spectrum.

The trapping column TC1 is washed with the solution 13 of mobile phase B and the trapping column TC2 traps the fourth components of interest eluted from the analytical column 4. The trapping column TC3 is washed(desalted) with the solution 13 of the mobile phase B.

All of the rotational change-over valves may be changed over periodically by using a timer.

In the apparatus shown in FIG. 5, as the plurality of trapping columns are processed in parallel in order to wash, trap, wash(desalt) and elute the components of interest, following problems in the conventional system should be improved upon;

(1) It is difficult to desalt and analyze many components of interest.

(2) It takes a long time for analytical processing.

However the system described above needs so many valves so as to damage its high quality separating function and also makes it expensive.

Figure 1:
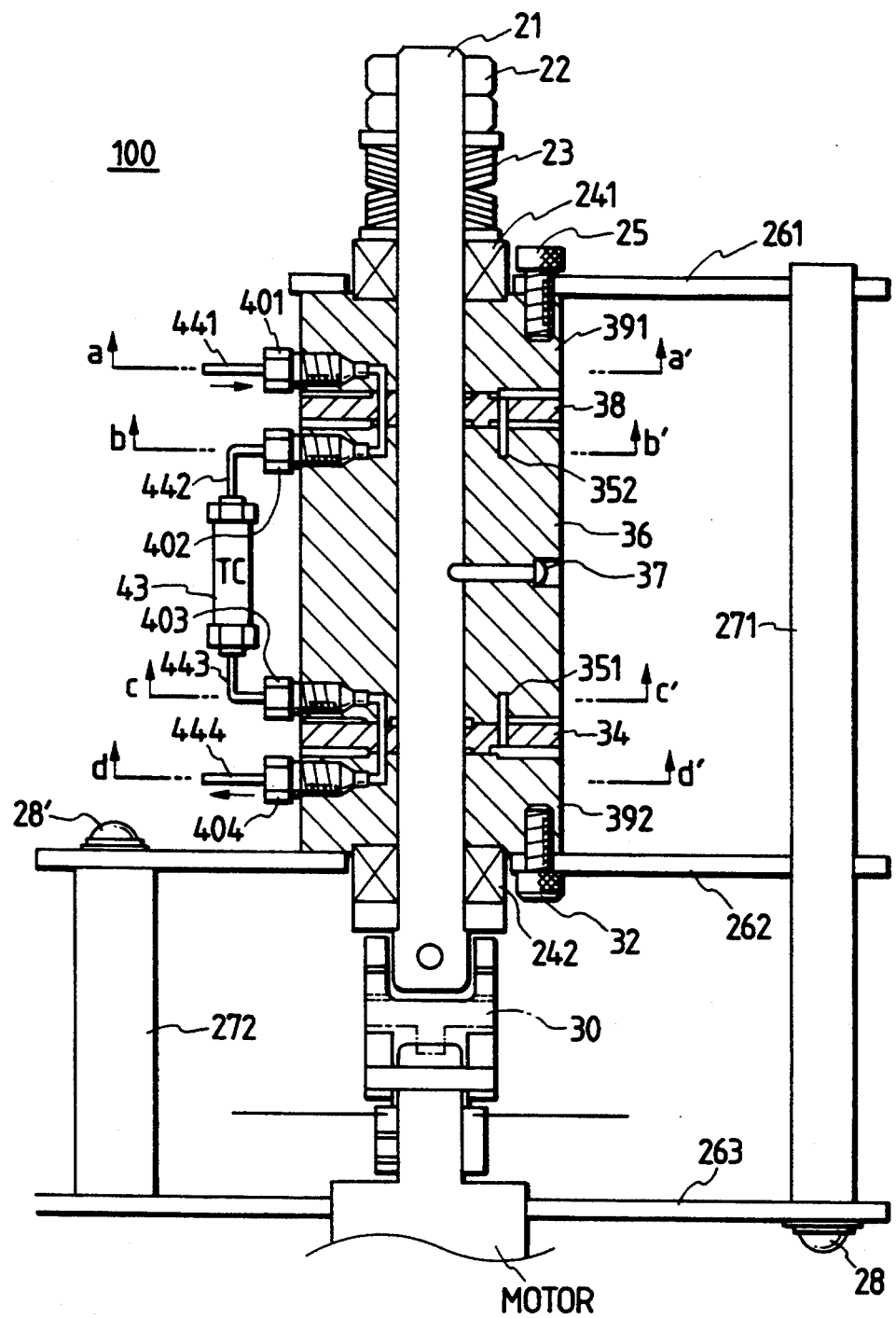
FIG. 1 shows a sectional view of an embodiment of change-over valves in the present invention.

FIG. 1 shows a sectional view of an embodiment of a change-over valve 100 for improving the above problems in the present invention.

The changing-over valve 100 shown in FIG. 1 eliminates many rotational valves and can simultaneously perform at least four process of trapping, washing-(desalting), eluting and washing in parallel. Thereby, complexed flow paths are simplified and many rotational valves are eliminated so as to make the production cost of the apparatus lower.

In FIG. 1, a movable member 36 fixed on a rotational axis 21 by a screw 37 is rotated by a motor through a universal coupling 30. Seal members 38, 34, formed from a material which has a high chemical resistance, low friction coefficient and does not wear easily, are fixed on an upper portion and a lower portion of the movable member 36 with fixing pins 351, 352. The movable member 36 is disposed between fixed members 391, 392 through seal member 38, 34, and the fixed members 391, 392 are respectively fixed on supporting plates 261 to 263 and supporting pole 271, 272 with screws 25, 32.

The rotational axis 21 is supported on the supporting plates 261, 262 with bearings 241, 242 and is rotated by sliding on both surfaces of the seal members 38, 34.

There are provided n number of input holes and n number of output holes at equal distances on outer circumference of sections a-a′, d-d′ of the fixed members 391, 392. In the same way, there are provided m number of input holes and m number of output holes at equal distances on outer circumference of sections b-b′, c-c′ of the movable member 36. Where both of the numbers n and m are four, angles between the input holes and angles between the output holes are respectively 90 degrees.

The input holes and the output holes are formed with a same structure and are connected to thin tubes 441 to 442 therein with setscrews 401, 404.

Figure 2:
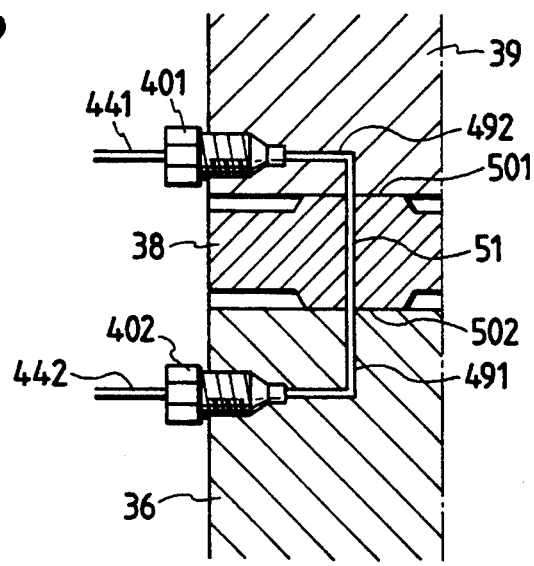
FIG. 2 shows a partial sectional view of a movable member and the fixed member of FIG. 1.

FIG. 2 shows an enlarged partial view of the input and output holes shown in FIG. 1.

Thin tube 492 is provided at inner end portion of the input hole in the fixed member 39 and thin tube 491 is provided at inner end portion of the output hole in the movable member 36. The thin tubes 491, 492 are provided so as to contact with respective sliding surfaces 502, 501 of the seal member 38 and are connected with each other through a thin tube 51 provided in the seal member 38. Thereby, solution flows from the tube 441 to the tube 442.

Spring washer 23 and nut 22, as shown in FIG. 1, make the movable member 36 and the fixed members 391, 392 firmly contacted through the respective seal members 34, 38 and no leakage of the solution arises at the sliding surfaces.

In the same way, the movable member and the fixed member are firmly contacted at all of the input and the output holes. In FIG. 1, a trapping column 43 is connected between the thin tubes 442 and 443 and the solution flows through a path of the thin tube 441 the setscrew 401—the setscrew 402—thin tube 442 the trapping column 43—the thin tube 443—the set screw 403—the setscrew 404—thin tube 444.

As the number of the trapping column are increased according to subject and needs of the analysis, m number of the trapping columns more than n may be mounted on the movable member 36.

EXAMPLE 1

A basic operation of the change-over valve in the present invention will be explained using FIGS. 6 to 10.

Figure 6:
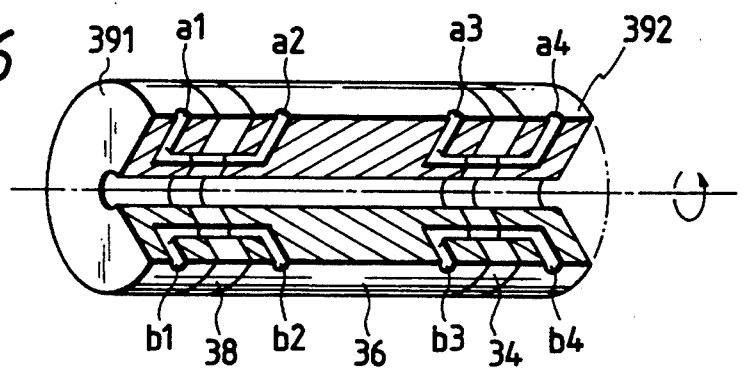
FIG. 6 is a partial perspective sectional view of an embodiment of change-over valves in the present invention.

FIG. 6 shows a partial sectional view of the change-over valve 100 having four input holes and four output holes on the movable member 36 and the fixed members 391, 392 respectively. As the input and the output holes are respectively four, each of the trapping columns is changed over when the movable member 36 rotates 360/4=90 degree. A hole a1 on the fixed member 391 is connected to a hole a2 on the movable member 36 and a hole a3 on the movable member 36 is connected to a hole a4 on the fixed member 392.

Figure 7:
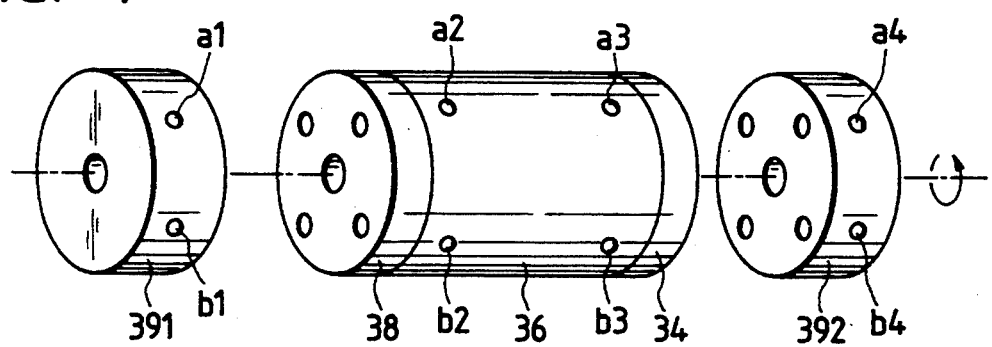
FIG. 7 shows an exploded view of the change-over valve in the present invention.

FIG. 7 shows an exploded view of the above change-over valve 100 in the present invention.

Figure 8A:
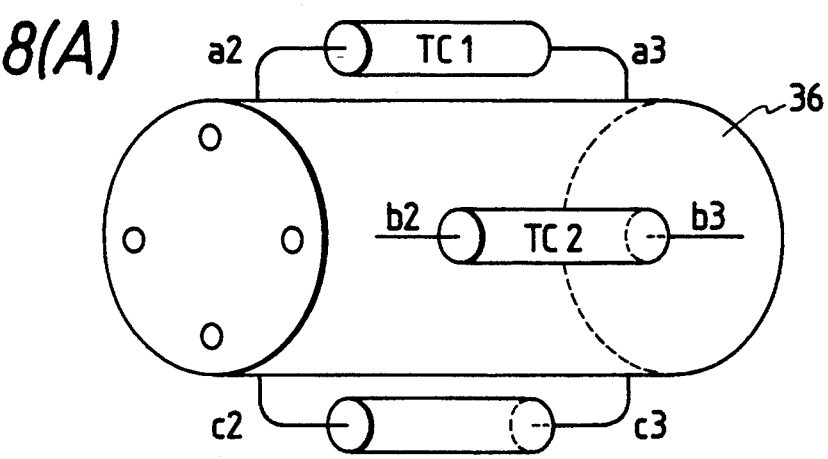
FIGS. 8(A), 8(B), 8(C), 9(A), 9(B), 9(C), 9(D) show a change-over system of the trapping column by the change-over valves in the present invention.
Figure 8B:
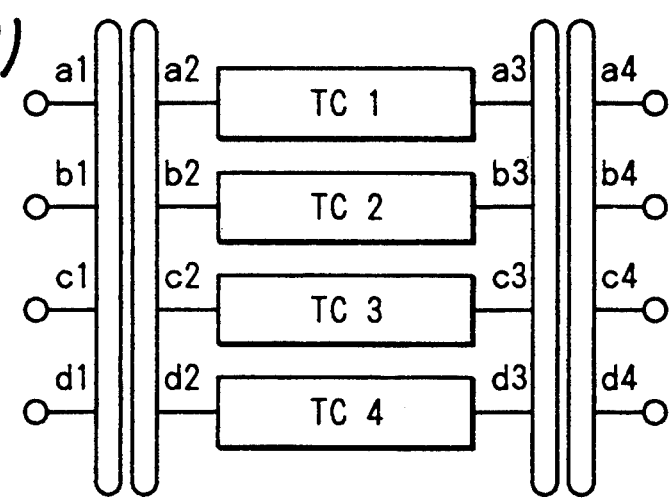
Figure 8C:
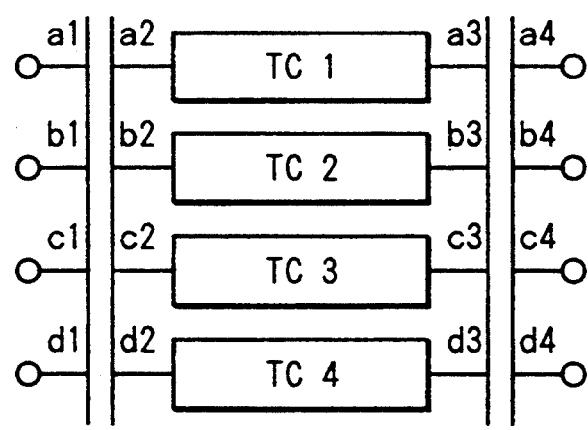
Figure 9A:
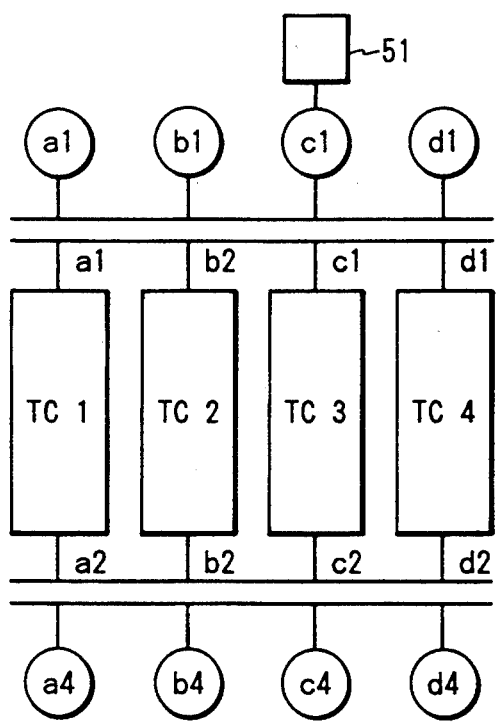
Figure 9B:
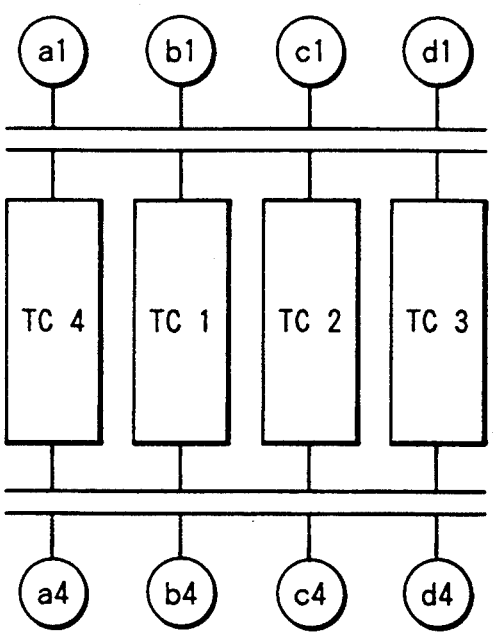
Figure 9C:
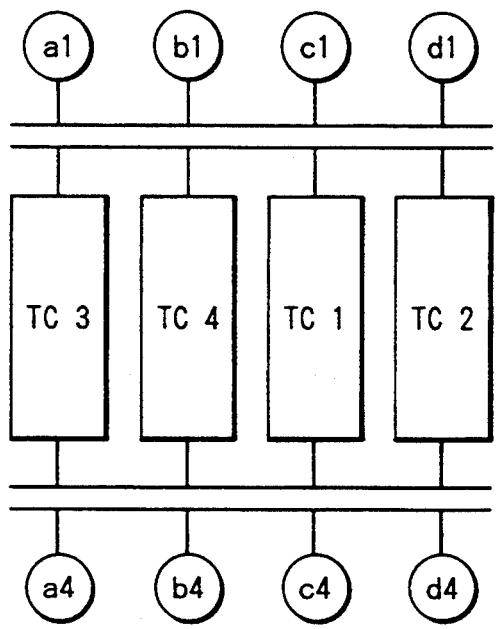
Figure 9D:
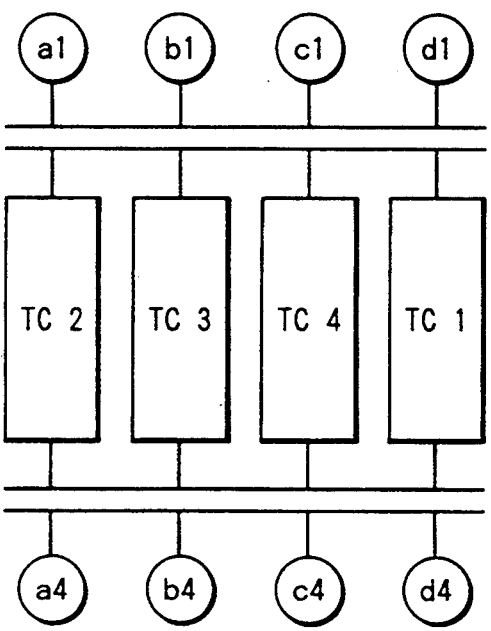

FIG. 8(A) shows the movable member 36 mounting the trapping column in the present invention, FIG. 8(B) shows a flow path in the change-over valve 100, and FIG. 8(C) shows a simplified figure of FIG. 8(B).

As shown in FIG. 8(B), each of the four trapping columns are respectively connected between paired holes, a2-a3, b2-b3, c2-c3 and d2-d3 and the solution flows in the hole a1 flows out of the hole a4 through a path of a2-TC1-a3.

The flow path a1-a4 is arranged to trap the analytical component of interest by the trapping column, flow path b1-b4 is arranged to wash so as to desalt the component of analyte in the trapping column, the flow path c1-c4 is arranged to elute the component of analyte trapped in the trapping column by back-flushing it, and the flow path d1-d4 is arranged to washing the trapping column by the solution of the mobile phase B such as water before trapping the next component of analyte.

Therefore, when the movable member 36 is rotated by every 90 degrees, the trapping columns are newly arranged allowing the four processing steps to be simultaneously performed in parallel and such change-over conditions are shown in FIGS. 9(A), 9(B), 9(C) and 9(D).

FIG. 10 shows a situation of the desalting in the condition shown in FIGS. 9(A), 9(B), 9(C), 9(D).

A detector 5, provided after the analytical column 4, detects components P1, P2 as shown in upper portion of FIG. 10 and a case for desalting the components P1, P2 will be explained. The movable member 36 is rotated at times of t0, t1, t2, t3, t4 so as to change over the trapping columns and change processing mode from (A) to (D).

For example in the case of the trapping column TC1, the processing is performed in order of the trapping, the desalting, the eluting and the washing, and in the case of the trapping column TC2, the processing is performed in order of the desalting, the eluting, the washing and then the trapping. In the same way, other processing relating to other trapping columns is performed, and the processing of the four trapping columns are performed by being either one step ahead or behind the respective adjacent column.

The components of interest P1, P2 are trapped by the trapping columns which are in the trapping processing when the components of interest P1, P2 are detected by the detector 51. Therefore, the component of analyte P1 is trapped by the trapping Column TC1 at the processing mode (A), then desalted at the processing mode (B) and is eluted by at the processing mode (C) so as to be detected as P1 by a detector 51. In the same way, the component of analyte P2 is trapped by the trapping column TC4 at the processing mode (B), is eluted at the processing mode (D) and is detected as p2 by a detector 51.

The bottom of FIG. 10 shows a chromatogram detected by the detector 51 and peaks P1, P2 are more sharp than peaks P1, P2 because of an effect of the back-flush.

Another embodiment of the present invention using the above change-over valve 100 will be explained next.

EXAMPLE 2

Figure 11:
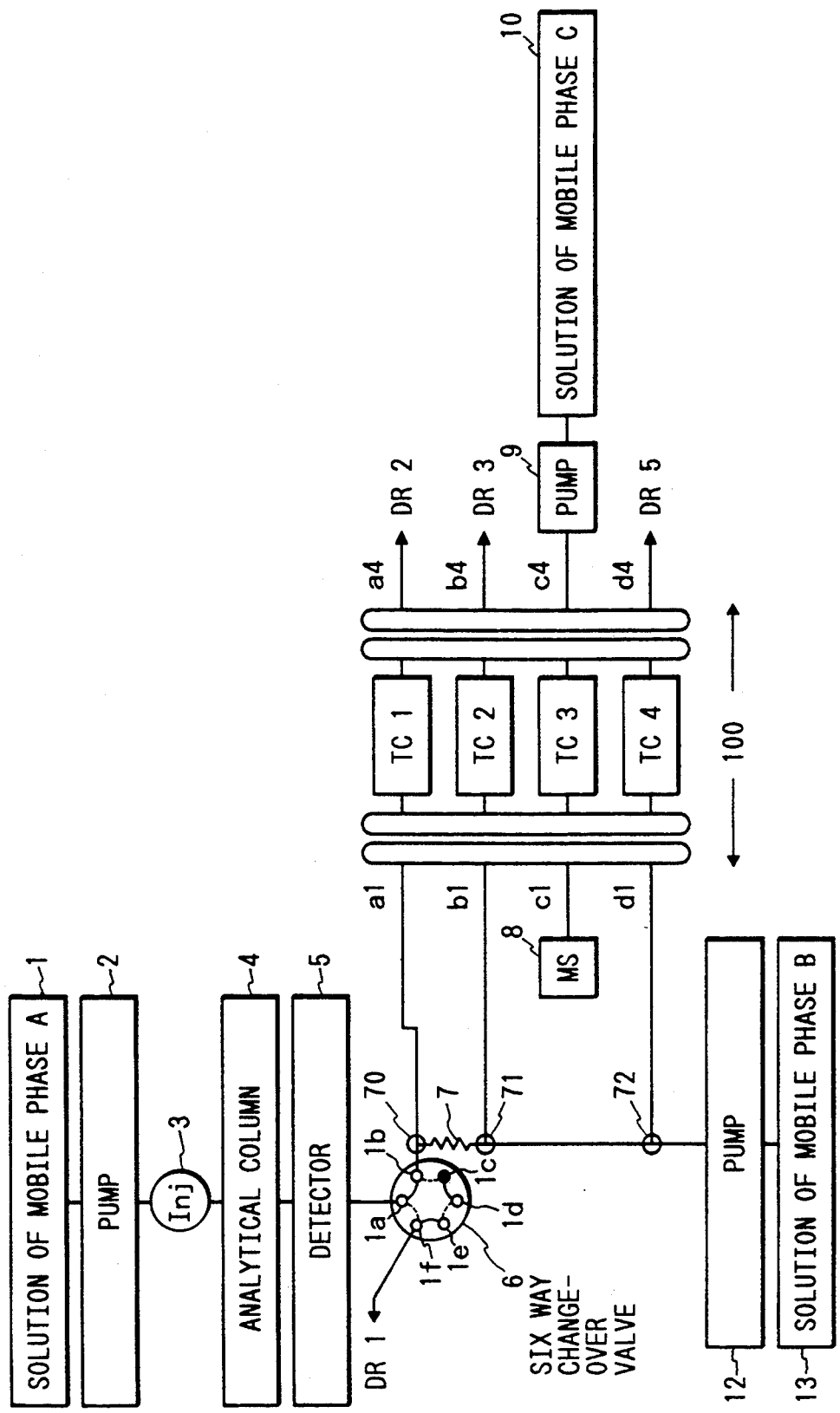
FIG. 11 shows a block diagram for showing another embodiment of the LC/MS system in the present invention.

FIG. 11 shows a block diagram of another embodiment of the LC/MS system of the present invention, in which components of non-interest in eluate A from the analytical column 4 are drained so as to avoid contaminating the system.

The solution of the mobile phase A is injected sample solution through a sample injection port 3 by a pump 2 and is separated by the analytical column 4 according to components of interest and detected by the detector 5. A flow path of the eluate A from the analytical column is changed over by a six way change-over valve 6 and is indicated by a solid line or a dotted line as shown in FIG. 11. A port 1c is sealed.

The eluate A is transmitted to a T-shaped tube 70 through 1a, 1b of the six way change-over valve 6 and is diluted with the solution of the mobile phase B transmitted by a pump 12 in order to effectively trap the analyte by increasing polarity thereof, and confluenced eluate is provided from input hole a1 of the change-over valve 100.

The analyte in the confluenced eluate is trapped by the trapping column TC1 and the eluate B from the trapping column TC1 is drained from the output hole a4 into a drain DR2.

The solution of the mobile phase B is a branch-ratio thereof, determined by a resistance column 7 so as to be branched to a flow path b1, d1, and washes the trapping columns TC2, TC4, and wasted into drains DR3, DR4 respectively through b4, d4. A needle valve may be used instead of the resistance column 7.

The solution 10 of the mobile phase C is transmitted by a pump 9, elutes the analyte trapped in the trapping column TC3, and eluate C containing the analytes are transmitted to a mass spectrometer 8 through output hole c1 so as to generate a mass spectrum.

Just before components of non-interest are eluted from the column 4, the change-over valve 6 is changed over to a state shown in the dotted line and the eluate A from the column 4 is wasted into a drain DR1. Thereby, the components of non-interest are not introduced into the change-over valve 100 and mass spectrometer 8, and the contamination in the system may be avoided.

Figure 12:
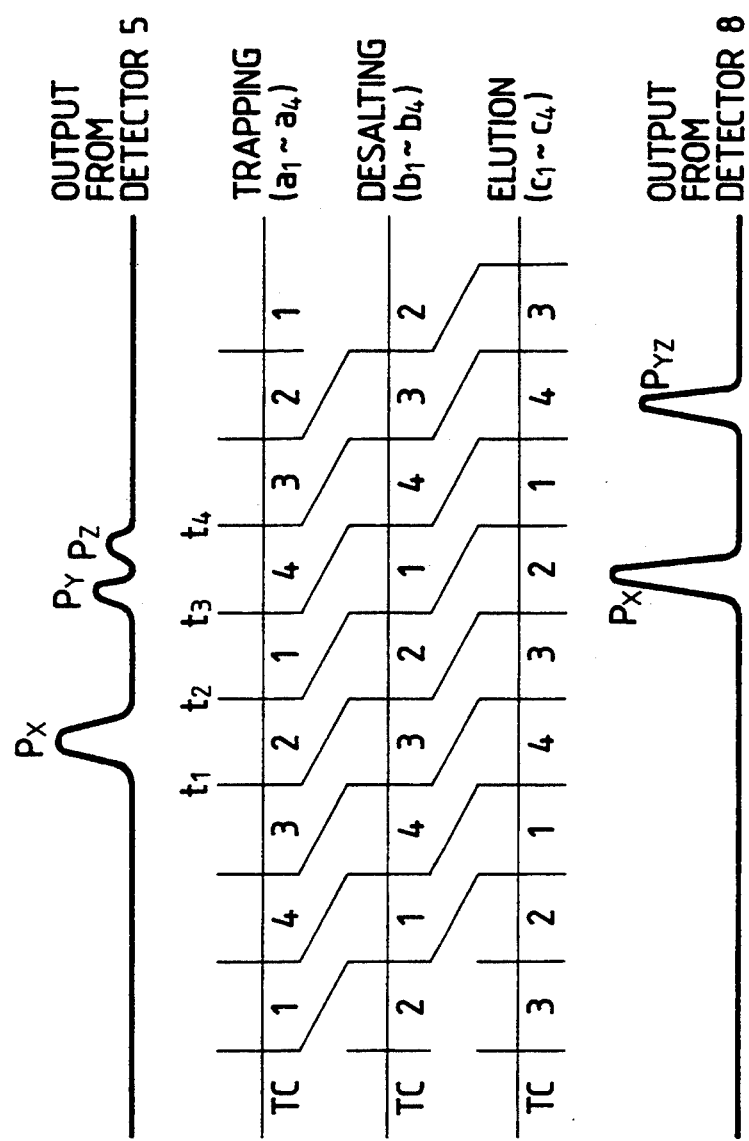
FIG. 12 shows an analytical processing view of the system shown in FIG. 11 in the present invention.

FIG. 12 shows an analytical processing view of the system in FIG. 11 in the present invention.

At the top of FIG. 12, a chromatogram of LC from the detector 5 is shown, a component Px is generated at time interval from t1 to t2 and eluted components Py and Pz are generated at time interval from t3 to t4.

The change-over valve 100 is rotated so as to be changed over with every 90 degrees in a predetermined cycle, for example one minute, whereby trapping columns as shown by column number in FIG. 12 are set in the flow paths of (a1-a4), (b1-b4), (c1-c4), (d1-d4).

Therefore, the trapping column TC2 is set in the flow path (a1-a4) at the time interval from t1 to t2 when the component Px is eluted. At the time interval from t2 to t3, the trapping column TC1 is set in the flow path (a1-a4) and the trapping column TC2 moves to the flow path (b1-b4) so as to be washed and desalted. At the next time interval from t3 to t4, the components Py and Pz are trapped by the trapping column TC4, simultaneously the trapping column TC1 moves to the flow path (b1-b4) so as to be washed and desalted and further the trapping column TC2 moves to the flow path (c1-c4) and the component Px is eluted by back-flush and is fed into the MS 8 so as to detect peak value px as shown at the bottom of the FIG. 12 by the detector 8.

In the same way, the analytes represented by peak values Py, Pz are trapped by the trapping column TC4 and finally eluted so as to generate one peak pyz. As shown in FIG. 12, the peak shape from the detector 8 is more sharp than those from the detector 5.

As stated above, the components eluted from analytical column are continuously desalted, eluted, washed and trapped without failing to analyze any component and a clear mass spectra of the components of interest are obtained.

EXAMPLE 3

In the system shown in FIG. 11, in the case that the peak value Py, Pz before fractionation are contained in one sampling cycle, the number of the peaks of the components of interest from the detector 8 does sometimes not correspond to that of the components eluted from analytical column.

In order to avoid such non-correspondence, the time between change-overs should be shorter. But, there is needed time for introducing into the inside of the trapping column other solvent types in order to desalt and wash, and further it is needed a constant time for completely removing the salt from the trapping column. Therefore, there is a limitation of the time for change-over the valve.

Figure 13:
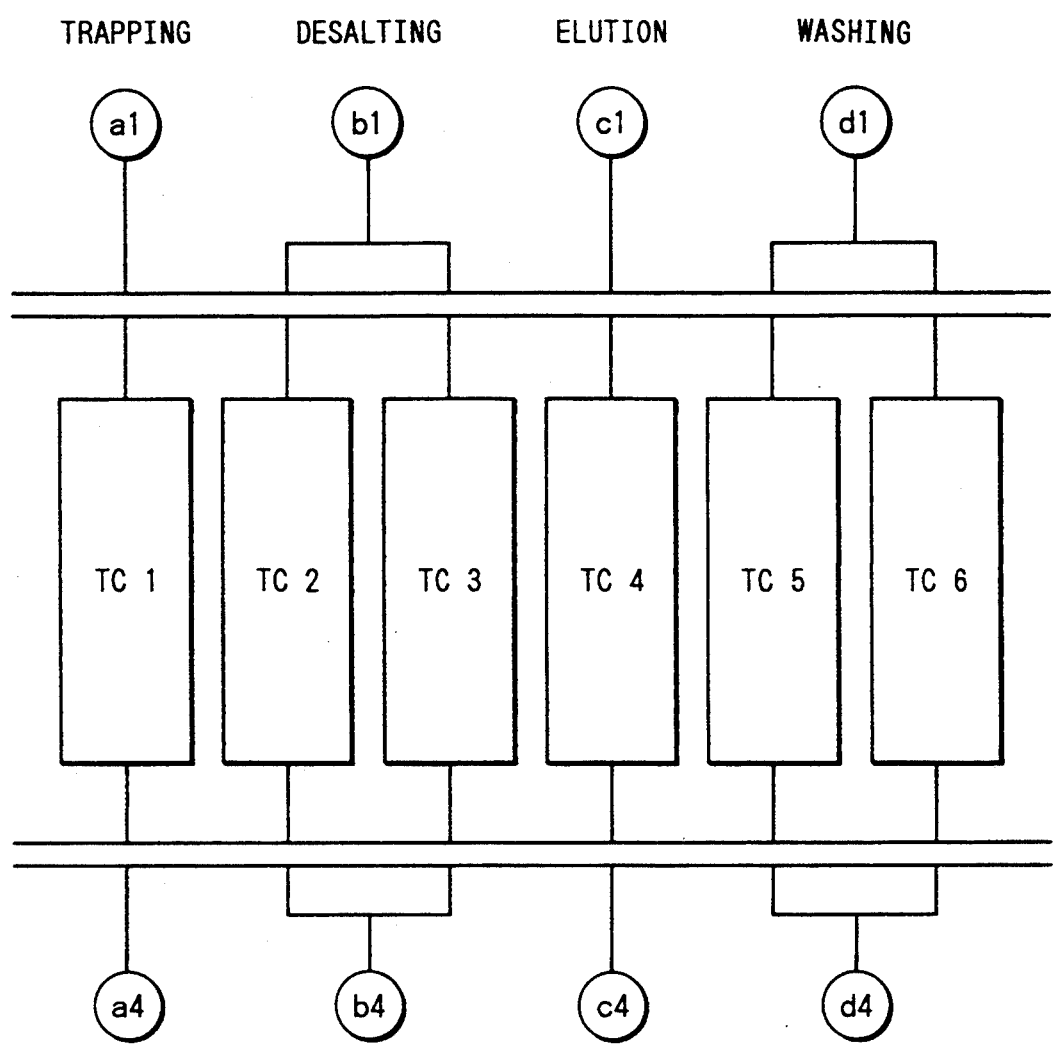
FIG. 13 shows another example of a change-over system of the trapping columns in the present invention.

In the embodiment shown in FIG. 13, the flow paths of the change-over valve 100 are increased and multiple trapping columns are provided in the flow path which for the steps that need are time for processing such as desalting, washing etc.

In FIG. 13, two trapping columns are provided in the flow paths for desalting b1-b4 and the flow path for washing d1-d4, and these two processing steps in the two trapping columns are simultaneously performed in parallel. Therefore, six trapping columns are provided in the four flow paths. That is, the trapping processing is performed in the flow path d1-d4 through the trapping column TC1, the desalting processing is performed in the flow path b1-b4 through the two columns TC2, TC3 in parallel, the eluting processing is performed in the flow path c1-c4 through the trapping column TC4, and the washing processing is performed in the flow path d1-d4 through the two columns TC5, TC6 in parallel. The change-over valve 100 is rotated 360/6=60 degree next by next so as to change over the flow paths.

The linear velocity of the solution flow in each of the parallel two columns is equal the flow in the other single columns. The processing speed of each columns in this embodiment can be half of that in the embodiment having four trapping columns.

Therefore, the time chart for showing analytical process of the trapping columns TC1, TC2, TC3, TC4, TC5, TC6 is as shown in FIG. 14 and those trapping columns take one cycle for the trapping, two cycles for the desalting, one cycle for the eluting and two cycles for the washing. Thereby, the peak values Py, Pz as shown at the top of FIG. 12 are respectively trapped in the different trapping columns each other and the peak pyz are separated.

EXAMPLE 4

As shown in FIG. 11, the six way change-over valve 6 is provided after the analytical column 4 and the detector 5, whereby the components of non-interest are selectively removed. But the six way change-over valve 6 is very expensive and it's preferable to avoid contamination. The embodiment shown in FIG. 15(A), 15(B) improves such problem.

Multiple bypass tubes are provided on the change-over valve 100 and the components of non-interest are drained to the outside through the bypass tubes so as to bypass the trapping column. Such bypass tubes may be provided in the change-over valve 100.

Figure 15A:
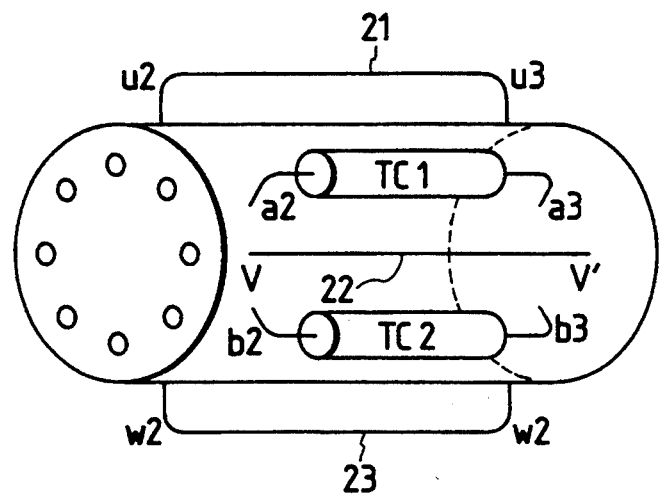
FIGS. 15(a), (b), 16 and 17 show further another examples of a change-over system of the trapping columns in the present invention.
Figure 15B:
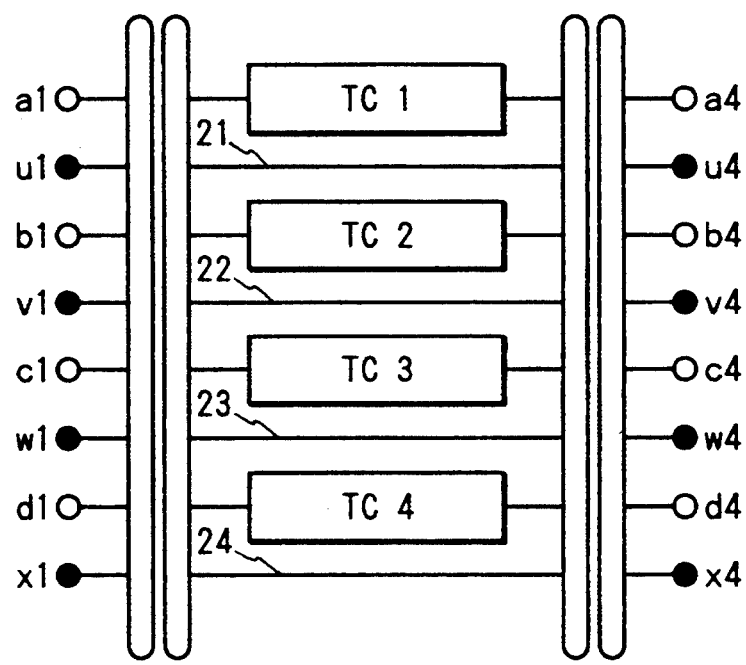

Thin tubes 21, 22, 23, 24 for bypassing are respectively provided between trapping columns TC1, TC2, TC3, TC4 as shown in FIG. 15(A) and the flow paths of the thin tubes 21, 22, 23, 24 are constructed as shown in FIG. 15(B). The trapping columns are arranged in the flow paths a1-a4, b1-b4, c1-c4, d1-d4 in the same way as in FIGS. 8, 11.

The flow paths u1-u4, v1-v4, w1-w4, x1-x4 may be used for other flow systems and input and output holes on the fixed member are sealed or may not be provided from the first.

Figure 16:
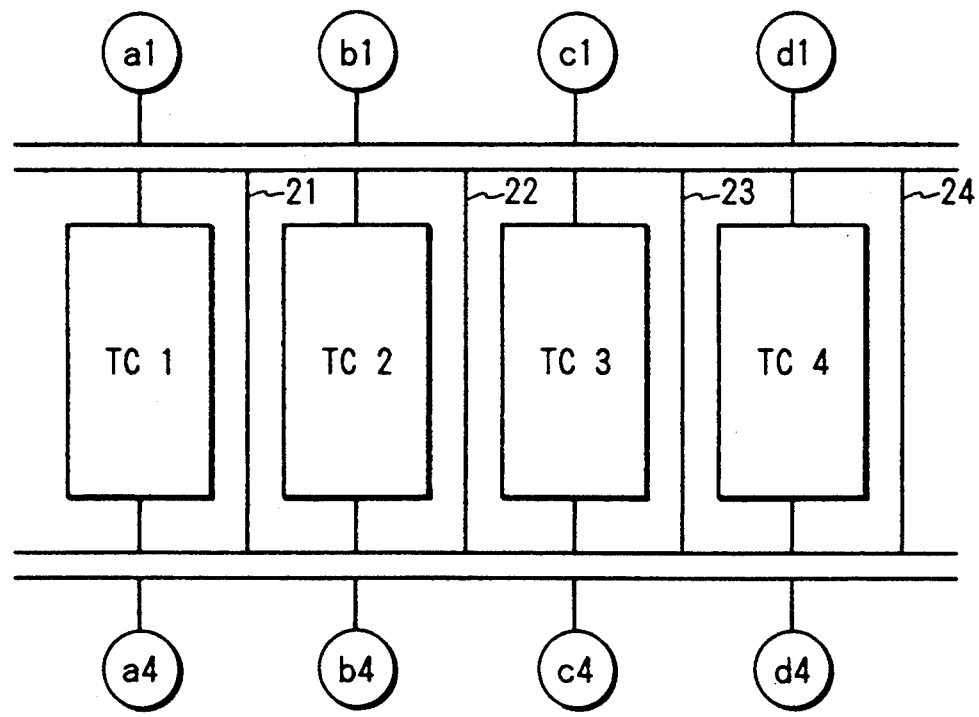
Figure 17:
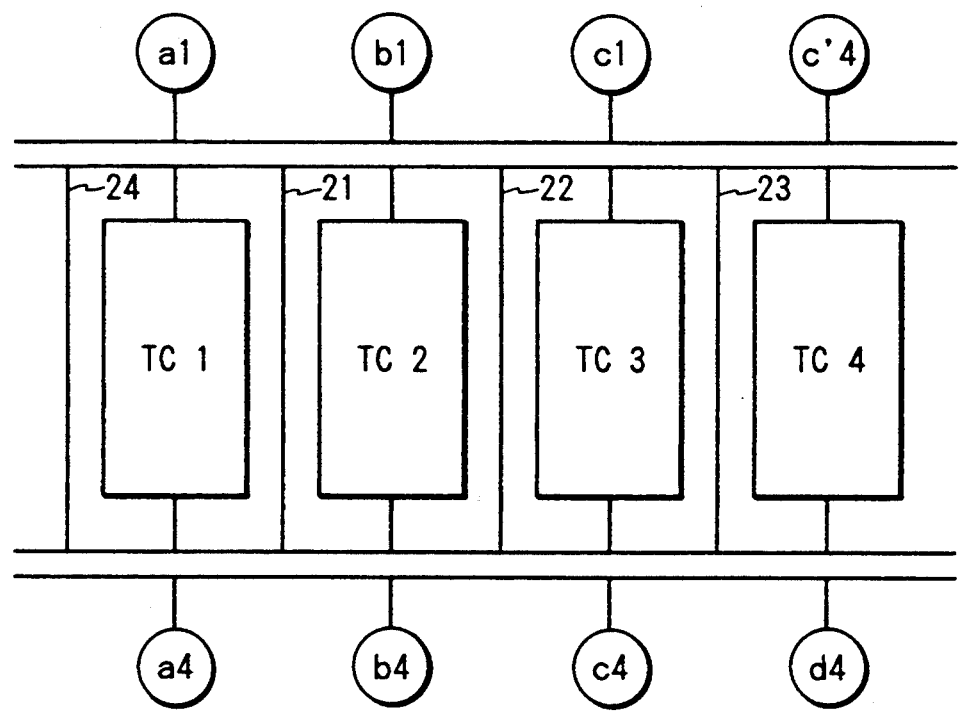

Change-over systems of the flow paths in the FIGS. 15(A), 15(B) is shown in FIGS. 16 and 17.

In FIG. 16, the change-over valve is rotated by 90 degree sequentially, and the change-over valve is operated in the same way as the cases in FIGS. 9, 11.

Further in FIG. 16, the change-over valve is rotated by 45 degree from the state shown in FIG. 16, the state of the change-over valve becomes as a state shown in FIG. 17, and all of the four flow paths a1-a4, b1-b4, c1-c4, d1-d4 are changed into a bypass state. Therefore, for example, when the eluate A flows into the flow pass a1-a4 from the analytical column 4, the nonobjective component is drained to the outside through the drain without being trapped by the trapping column, and after the nonobjective component is drained to the outside, the normal flow path for the processing system of the trapping, the desalting, the eluting, and the washing as shown in FIG. 16 is reestablished.

Figure 18:
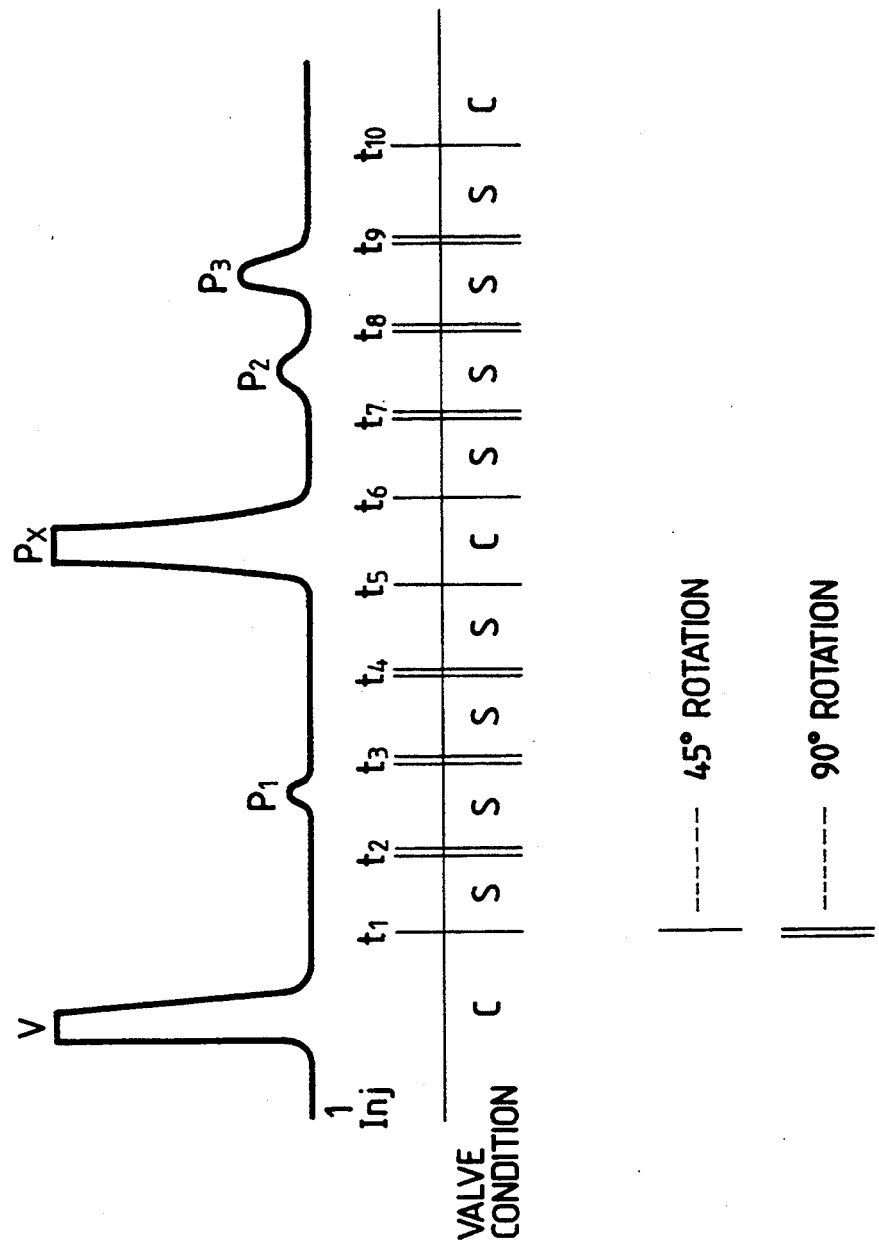
FIG. 18 shows a graph of an analytical process carried out by the system in FIG. 15 in the present invention.

FIG. 18 shows the process operation stated above. A chromatogram of LC detected by the detector 5 is shown at the top of FIG. 18, and V and Px are components of non-interest which should be removed and P1, P2, P3 are components of interest. The components of interest trapped by the trapping column are eluted by the solution of the mobile phase A containing much nonvolatile buffer.

The bottom of FIG. 18 shows a change-over mode of the change-over valve 100 and code "C" means a removing mode of the component of non-interest and code "S" means a sampling mode of the component of interest. One vertical solid lines means a rotation of 45 degrees of the change-over valve 100 and two vertical solid lines means a rotation of 90 degrees of the change-over valve 100.

At the same time as injecting the sample solution, the change-over valve is changed over into the mode C and then at a time t1 after finishing the elution and voiding said volume components the change-over valve 100 is rotated 45 degree so as to be the sampling mode S and the change-over valve 100 is rotated 90 degree next by next and the sampling process is performed.

Then, at a time t5 just before a peak value Px arises, the change-over valve 100 is rotated over 45 degrees and is changed over to be in the mode C, and at a time t6 when the component Px is finished eluting, the valve 100 is again rotated 45 degree so as to come back to the sampling mode. Then, after the sampling are repeated by changing over the valve 100 sequentially and at a time t10 when all of the analysis are finished, the valve 100 is rotated 45 degree so as to be changed to be in the removing mode C to remove the components of non-interest, and all of the components of non-interest are drained to outside through the drain. Further, conditioning of the analytical column 4 may take place at this time.

Figure 19:
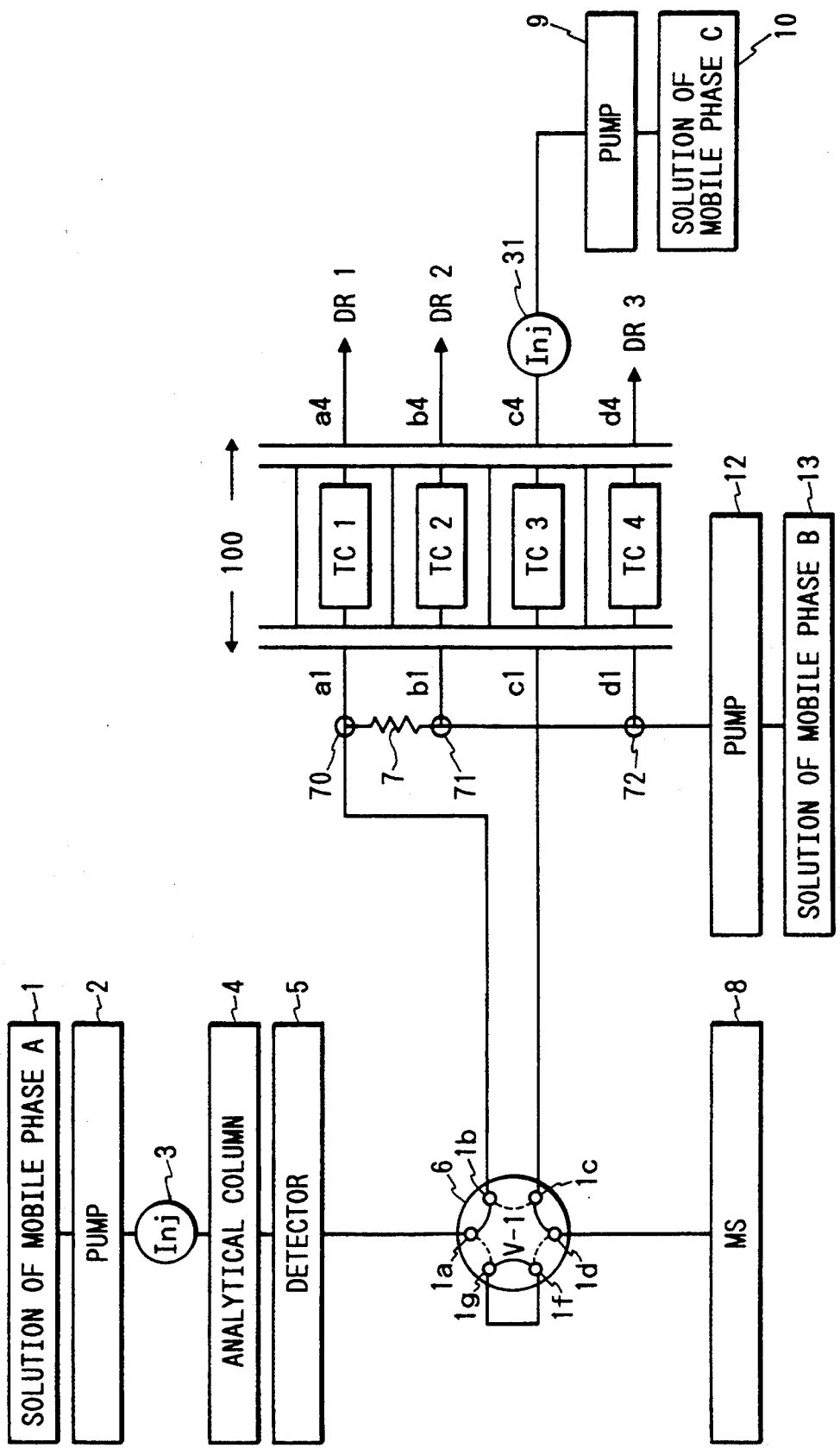
FIG. 19 shows a block diagram for showing a further embodiment of the LC/MS system in the present invention.

FIG. 19 shows a block diagram of LC/MS system based on the above explained embodiments having function as follows;
(1) Continuous analyzing of multiple components of interest in the solution of the mobile phase containing non-volatile components
(2) Directly introducing eluate A of LC by volatile solution of the mobile phase into the MS,
(3) Removal of the components of non-interest, and
(4) Analysis by flow injection.

Process for performing the above function will be explain as follows;
(1) Process for desalting and removing the component of non-interest, The solution of the mobile phase A which consist of carrier solvent transmitted by the pump 2 and the sample solution is injected thereto and is separated by the analytical column 4 according to the components therein and is detected by the detector 5. The eluate A from the detector transmitted through ports 1a, 1b of a six way change-over valve 6 is transmitted to a tee 70, is diluted with the solution 13 of the mobile phase B transmitted from the pump 12 so as to form the confluenced eluate and is then transmitted to the flow path a1-a4 of the change-over valve 100. The dilution ratio of the confluenced eluate is determined by the resistance column 7 and the resistance column 7 may be substituted with a needle valve etc.

Further the solution 13 of the mobile phase B is supplied to the flow paths b1-b4, d1-d4 etc.

The flow path c1-c4 is used for eluting the components of interest trapped in the trapping column and the components of interest are eluted by backflushing the solution 10 of the mobile phase C transmitted by the pump 9 into the trapping column. The eluate C from the port cl is transmitted to the MS 8 through port 1c, 1d of the six way change-over valve 6 so as to be mass-analyzed. The desalting process is performed by changing over the valve 100 in the same way as shown in FIG. 9. The components of non-interest are removed by using the bypass flow path of the changeover valve 100 in the same way as shown in FIGS. 16, 17, 18.

(2) Process for directly introducing eluate A of LC into the MS by use of volatile solution of the mobile phase.

There is no need to perform the processes for trapping, desalting, eluting etc. in the case of the solution of the mobile phase which does not contain non-volatile components and the eluate A from the analytical column 4 is directly transmitted to the MS 8. Therefore, the six way change-over valve 6 is changed over shown as dotted lines and the eluate A is transmitted to the MS 8 through the path of 1a, 1g, 1f, 1d. At this time, the path of the change-over valve 100 may be either in the mode for removing the component of non-interest or in the mode S for sampling and in the both mode all of the flow paths are washed with solvent so as to prevent plugging and contamination of the flow paths.

(3) Process for flow injection analysis,

In the case for analyzing by optimizing the analytical condition, flow injection analysis without the analytical column is widely used.

In this flow injection analytical mode, all of the flow paths of the change-over valve 100 are set to be in the bypass mode C. The solution 10 of the mobile phase C injected the sample solution from the sample injection port 31 is transmitted by the pump 9 from port c4 to port cl through the thin tube of the change-over valve 100, and further transmitted to the MS 8 through path of 1c, 1d shown as solid lines in the six way change-over valve.

At this time, the eluate A is wasted to the drain DR1 by the pump 2 through the path of ports 1a, 1b, tee 70, path a1-a4 in the bypass mode. Further the pump 12 is operated so as to wash the system.

As stated above, conditioning of the analytical column 4 is performed while the MS is operated.

EXAMPLE 5

Figure 20:
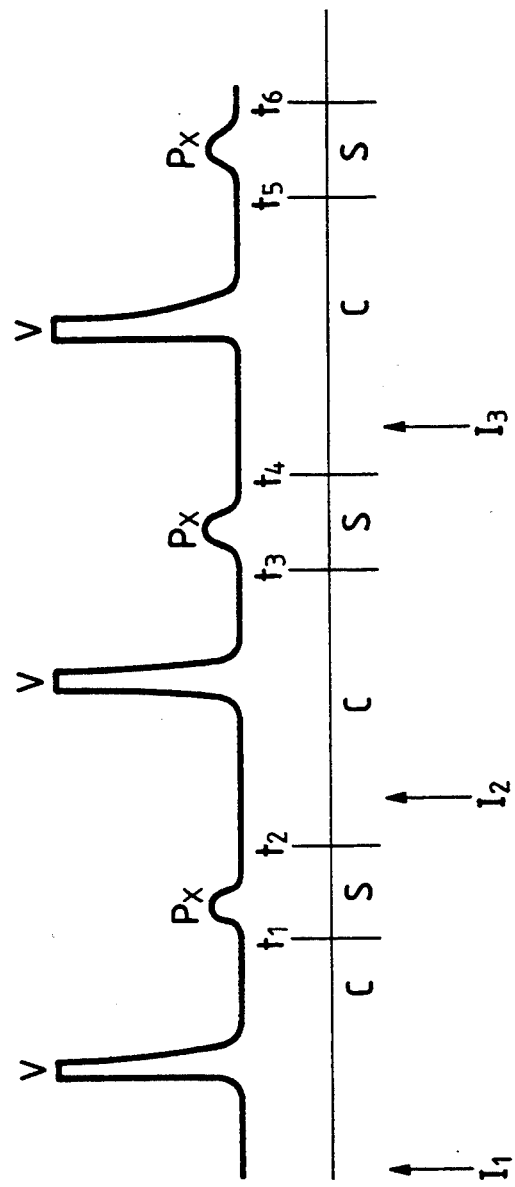
FIG. 20 shows a graph of an analytical process carried out by the system in FIG. 19 in the present invention.

FIG. 20 shows an analytical process of the apparatus for concentrating trace components in post-column in the present invention.

At first, the six way change-over valve 6 is changed over shown as solid lines so as to be changed in the mode C, the sample solution is injected in the injection port 3 at time I1 and component of non-interest V is removed.

Second, the change-over valve 100 is rotated 45 degrees so as to be changed over to be in the sampling mode S at time t1 just before the component of interest Px is eluted from analytical column, and the component of interest Px is trapped by the trapping column TC1, then at time t2 when the trapped eluate is finished eluting, the change-over valve 100 is rotated back 45 degree so as to be in the mode C for removing the components of non-interest. Then the process from the time-interval I1 to t2 is repeated and the concentrated components of interest are trapped in the trapping column TC1. Subsequently the processes of desalting, eluting for analyzing are taken place. As stated above, as desired trace component in the mixture are concentrated after being eluted from the analytical column, the trace component is analyzed in high sensitivity.

EXAMPLE 6

Figure 21:
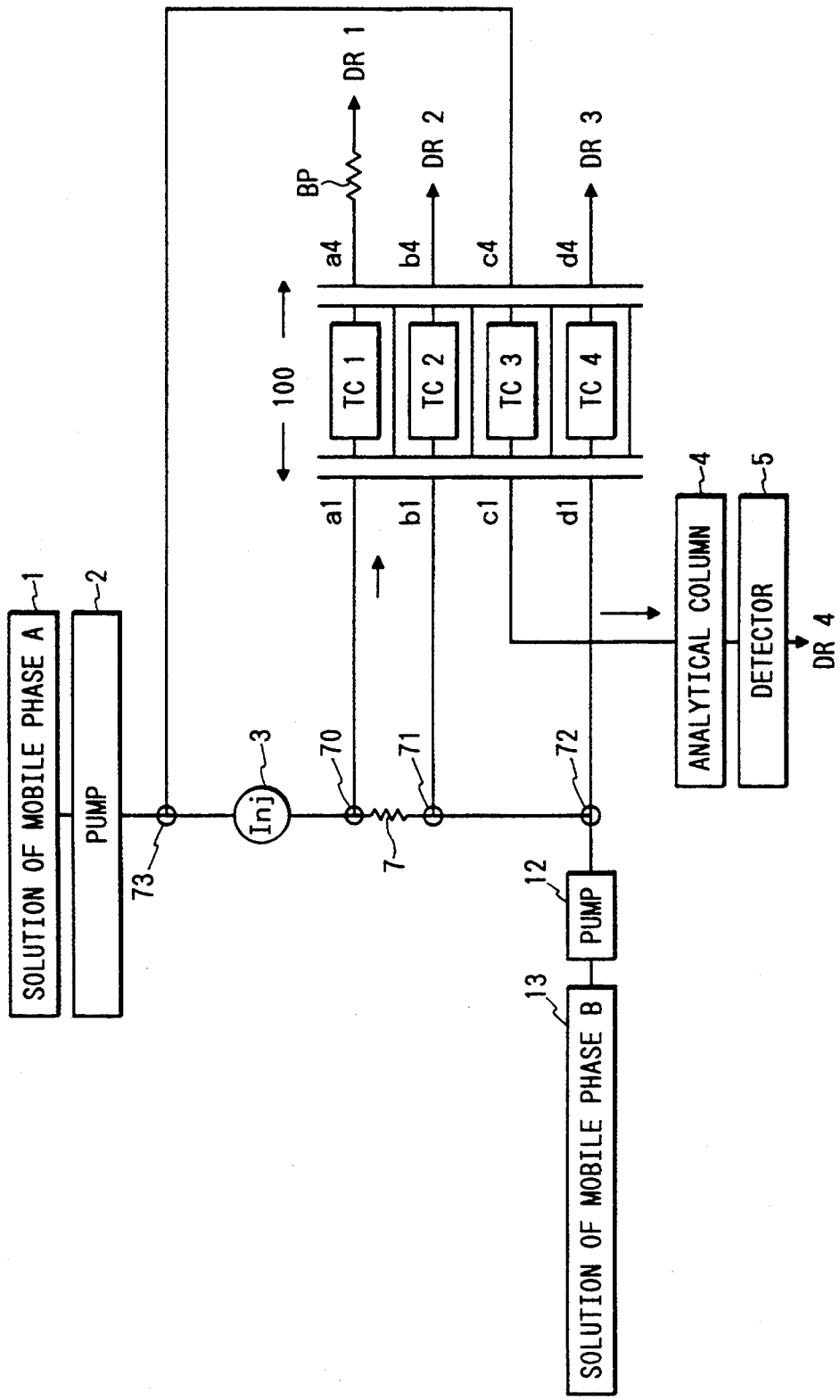
FIG. 21 shows a block diagram for showing an embodiment of sample concentration by a pre-column using change-over valve in the present invention.

FIG. 21 shows a block diagram for showing an embodiment of sample concentration by using a pre-column before injection into the analytical column 4 in the present invention.

In order to concentrate multiple trace components, the concentration of the components is performed before being transmitted to the analytical column 4, and after that the analytical column separates the trace components, thereby a sensitive analysis becomes possible.

The carrier solvent 1 transmitted by the pump 2 is divided into two paths by tee 73 and is transmitted from one of the paths to the tee 70, and other of the paths is connected to the input hole C4 of the change-over valve.

The solution of the mobile phase A transmitted to the tee 70 is diluted by the solution 13 of the mobile phase B, and the component of interest therein is trapped by the trapping column TC1. The eluate B is wasted to the drain DR1 through hole a4 and the resistance column BP. The resistance column BP is provided in order to make the pressure of the column TC1 balanced to the that of the other flow path. The sample injection process as above is repeated so as to make the components of interest in the trapping column TC1 concentrated.

After finishing the concentration of the components of interest, the change-over valve 100 is changed over in the same way as shown in FIGS. 9, 10 and the components of interest trapped in the trapping column TC1 are desalted and eluted.

The trapping column TC1 is moved into the flow path of c1-c4 so as to make the components of interest flow into the analytical column 4 and the components of interest are separated and detected by the detector 5.

Figure 22:
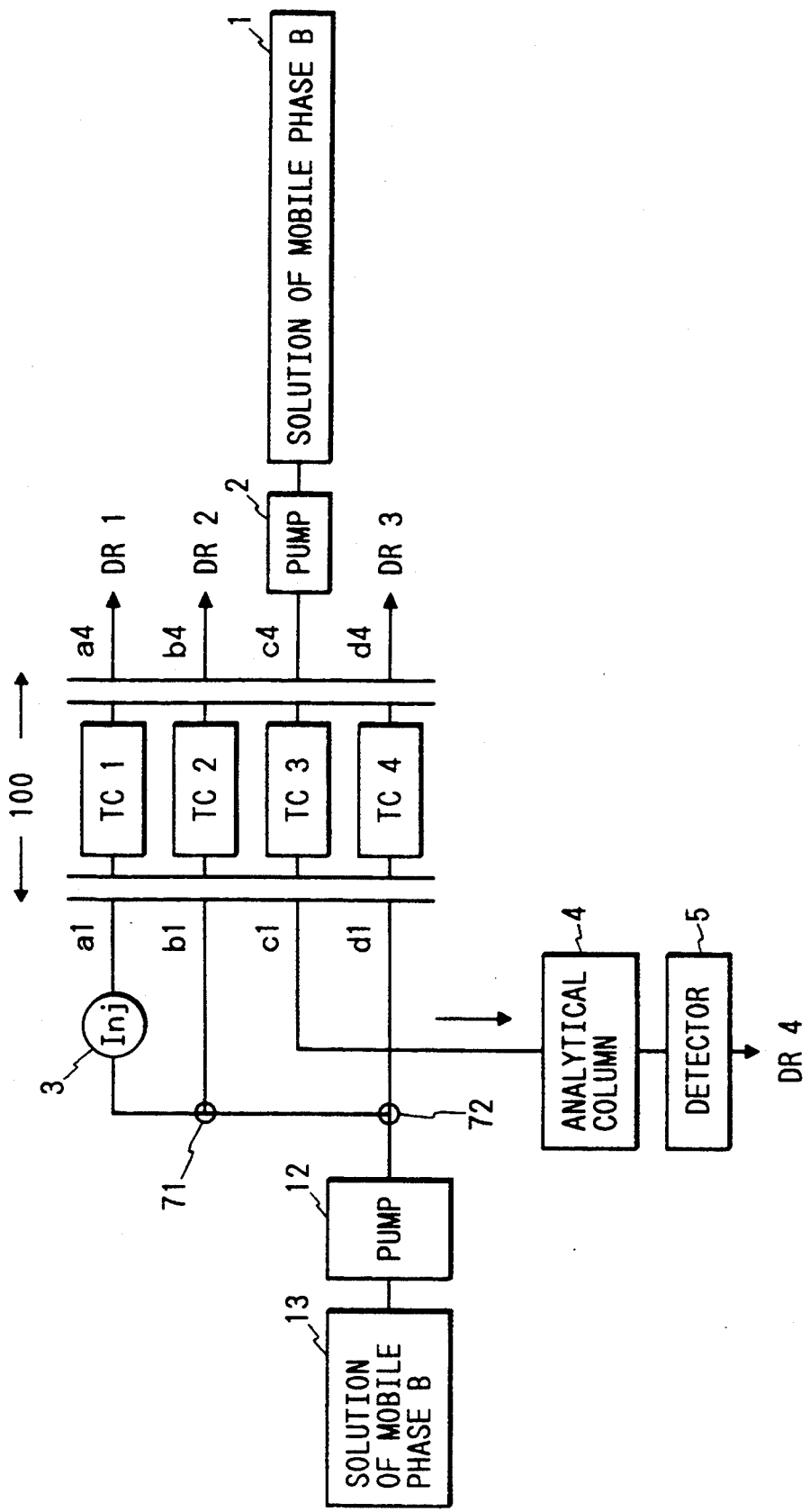
FIG. 22 shows a block diagram for showing another embodiment of a concentrate analysis by a precolumn using a change-over valve in the present invention.

FIG. 22 shows another block diagram for concentrating components of interest using the pre-column. The solution 13 of the mobile phase B injected the sample solution injected through the injection port 3 is transmitted to the flow path a1-a4. The sampling injection as above is repeated so as to fully concentrate the component of analyte in the trapping column TC1.

Then, the change-over valve 100 is changed over to the flow path b1-b4 so as to wash the trapping column TC1. Further, the change-over valve 100 is changed over to the flow path c1-c4 so as to elute the concentrated component in the trapping column TC1 by using the solution 1 of the mobile phase A transmitted by the pump 2 and the eluate from the trapping column TC1 is transmitted to the analytical column 4 so as to analyze the components.

Furthermore, as the change-over valve has a plurality of the same trapping columns, the concentrated component by the trapping column TC3 may be analyzed by using LC while the concentration operation is performed in the trapping column TC1 so that the efficiency of the analysis is improved more remarkably than the method using only one trapping column.

In the above system, the sample solution is injected in the solution 13 of the mobile phase B, and alternatively, the sample solution may be injected directly by using a syringe.

Further, an auto-sampler may be used and the analyzer such as a post column desalting system shown in FIG. 19 or the MS may be used.

EXAMPLE 7

Figure 23:
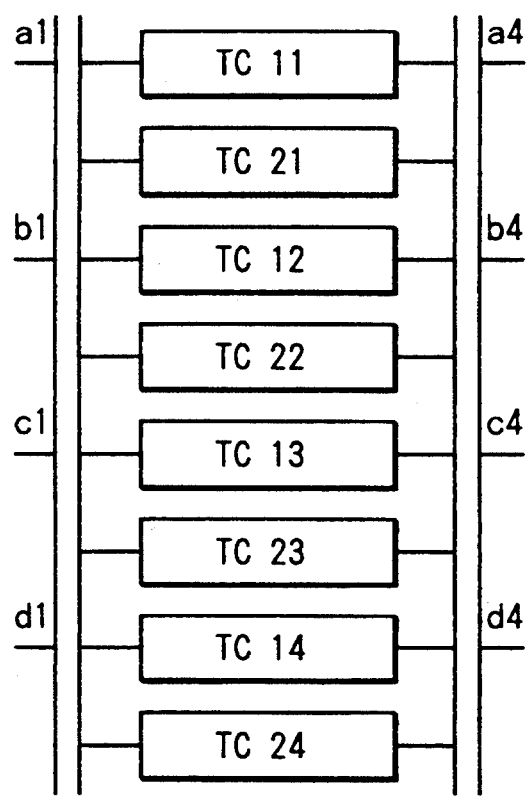
FIG. 23 shows another example of a changed over system of the trapping columns in the present invention.
Figure 24:
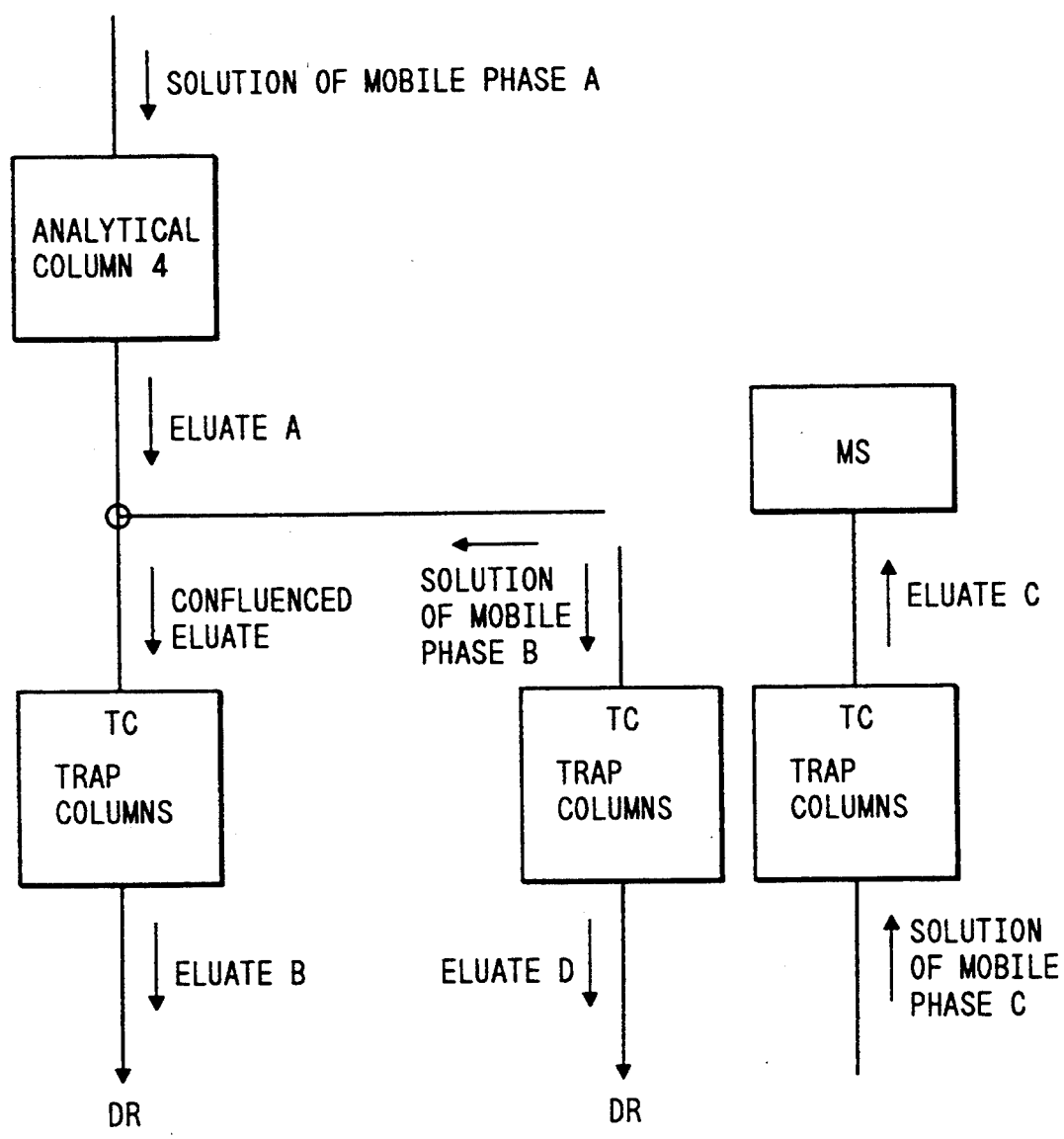
FIG. 24 shows the conventional processes carried out by LC/MS apparatus.

FIG. 23 shows a block diagram for showing another embodiment of the change-over valve in the present invention. A number of channels of the trapping columns are mounted on the movable member 36 in FIG. 23, and for example the eight trapping columns are mounted wherein the same kind of the trapping columns are alternately arranged. That is, when two kind of the trapping columns such as first group of (TC11, TC12, TC13, TC14) and second group of (TC21, TC22, TC23, TC24) are provided, one of the first group of (TC11, TC12, TC13, TC14) and one of the second group of (TC21, TC22, TC23, TC24) is alternately arranged on the movable member 36.

Each of the first group of (TC11, TC12, TC13, TC14) is used for a reversed-phase column ODS and each of the second group of (TC21, TC22, TC23, TC24) is used for ion-exchange column, and the first group may be used as a reverse-phase chromatography and the second group may be used as a ion-exchanging chromatography.

By rotating the change-over valve 100 every 90 degrees, either one of the reverse-phase chromatography and the ion-exchanging chromatography is used and by rotating the valve 100 45 degrees once and thereafter by rotating the valve every 90 degree, another one is selected, and therefore any one of the reverse-phase chromatography and the ion-exchanging chromatography may be selected and used whenever the operator wants.

In the above embodiments, LC is connected to the input side of the valve 100 and the MS is connected to output side of the valve 100, but FIA may be connected to the input side and other analyzing device may be connected to the output side.

Instead of the detector 5, an ultraviolet spectrometer or fluorescence spectrometer may be used.

The change-over valve 100 is used as a fraction c collector and the eluate A is substituted into solvent which is easily processed after being desalted so as to simplify the processing thereafter.

As explained above in the present invention, at least four trapping columns corresponding to four processing steps are used on the movable member, but herein after in the present invention, improved four processing modes make it possible to use a single common trapping column instead of the above four trapping columns.

Figure 25:
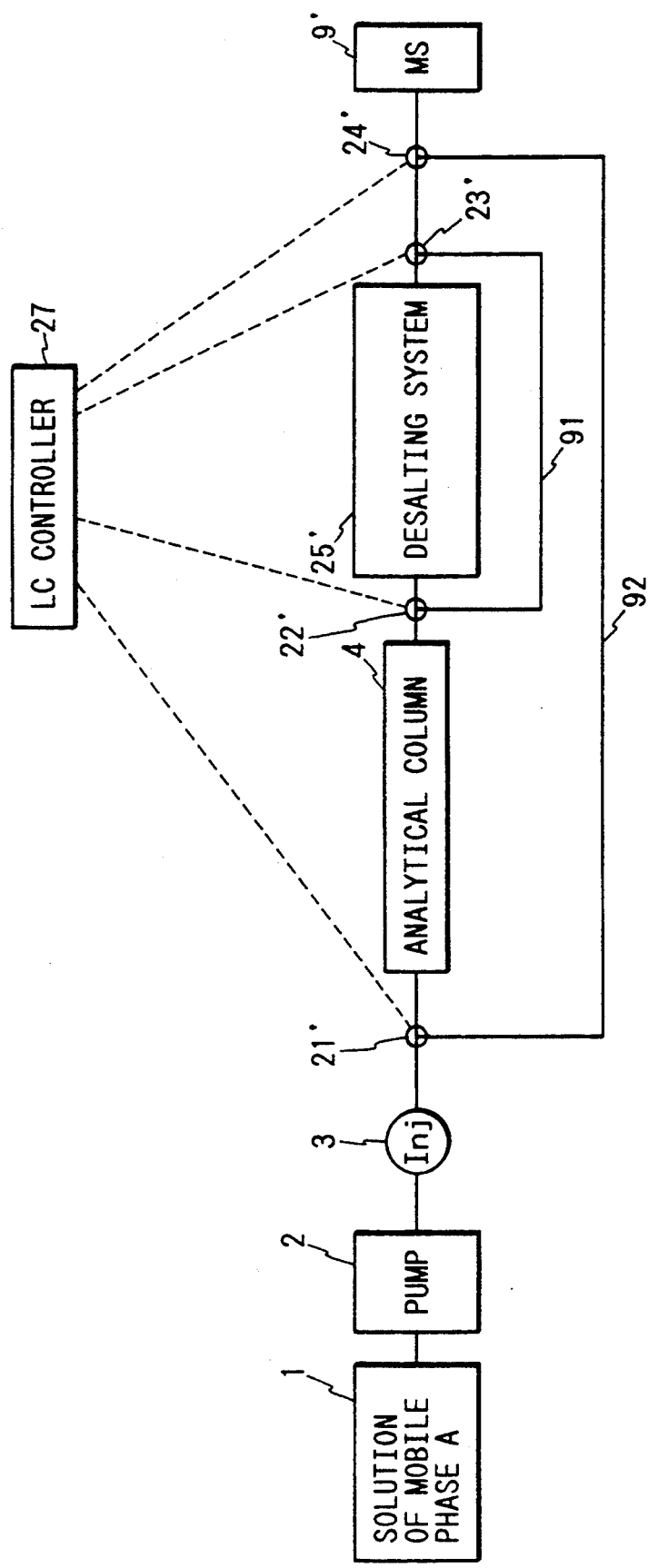
FIG. 25 is a block diagram for showing another embodiment in the present invention.

FIG. 25 shows a schematic block diagram of an embodiment of such invention.

In FIG. 25, numeral 9' means an ion source of the MS; 21', 22', 23', 24' respectively three way change-over valves; 25' desalting system for non-volatile salt; 27' controller for LC; 91', 92', respectively flow paths. Other numerals which correspond to those in the former figures represent the same elements as in the former figures.

The system shown in FIG. 25 uses the following three analytical systems (1), (2), (3) by changing over the respective three way change-over valves 21', 22', 23', 24' which are controlled by the LC controller 27'.

(1) Analytical system by the volatile solution of the mobile phase,

In this case, the sample solution is injected from the injection port 3 and the three way change-over valve 21' is changed over so as to transmit the solution to the analytical column 4 and components of the solution are separated. At this time, the three way change-over valves 22', 23' are changed over so as to flow the eluate A to the flow path 91'.

Then the eluate A containing analytes is fed to the ion source 9' of the MS through the three way changeover valves 23', 24', whereby the eluate A containing the components of interest is directly transmitted to the ion source 9' of the MS by bypassing the desalting system 25' and the analytes so as to provide a mass spectra.

(2) Analytical system of the non-volatile solution of the mobile phase by desalting, The solution 1 of the mobile phase A containing the non-volatile buffer and the non-volatile salt is transmitted by the pump 2. The sample solution is injected through the sample injection port 3, and the change-over valve 21' is changed so as to transmit the sample solution to the analytical column 4, thereby the analytical components are separated by the analytical column 4.

The valve 22' is changed over so that the separated components with the eluate A are transmitted to the desalting system 25' and further transmitted through the desalting system 25'.

The components of interest are once trapped in the trapping column 12' (not shown in the figure) in the desalting system 25', and washed so as to be desalted. The trapped components of interest are eluted by the solution of the mobile phase C (not shown in the figure) which does not contain the non-volatile salt. The eluate C containing the components of interest is transmitted to the ion source 9' of the MS by changing over the valves 23', 24' so as to be ionized and provide a mass spectrum.

(3) Flow injection system,

In this case, the sample solution injected from the sample injection port 3 is transmitted to the ion source 9' of the MS from the three way change-over valves 21' with the carrier solvent, that is the solution 1 of the mobile phase A, through the flow path 92' and through the three way change-over valve 24' so as to be ionized and provide a mass spectrum.

In this way as explained above, the three analytical systems are easily performed by changing over multiple three way change-over valves.

EXAMPLE 8

Figure 26:
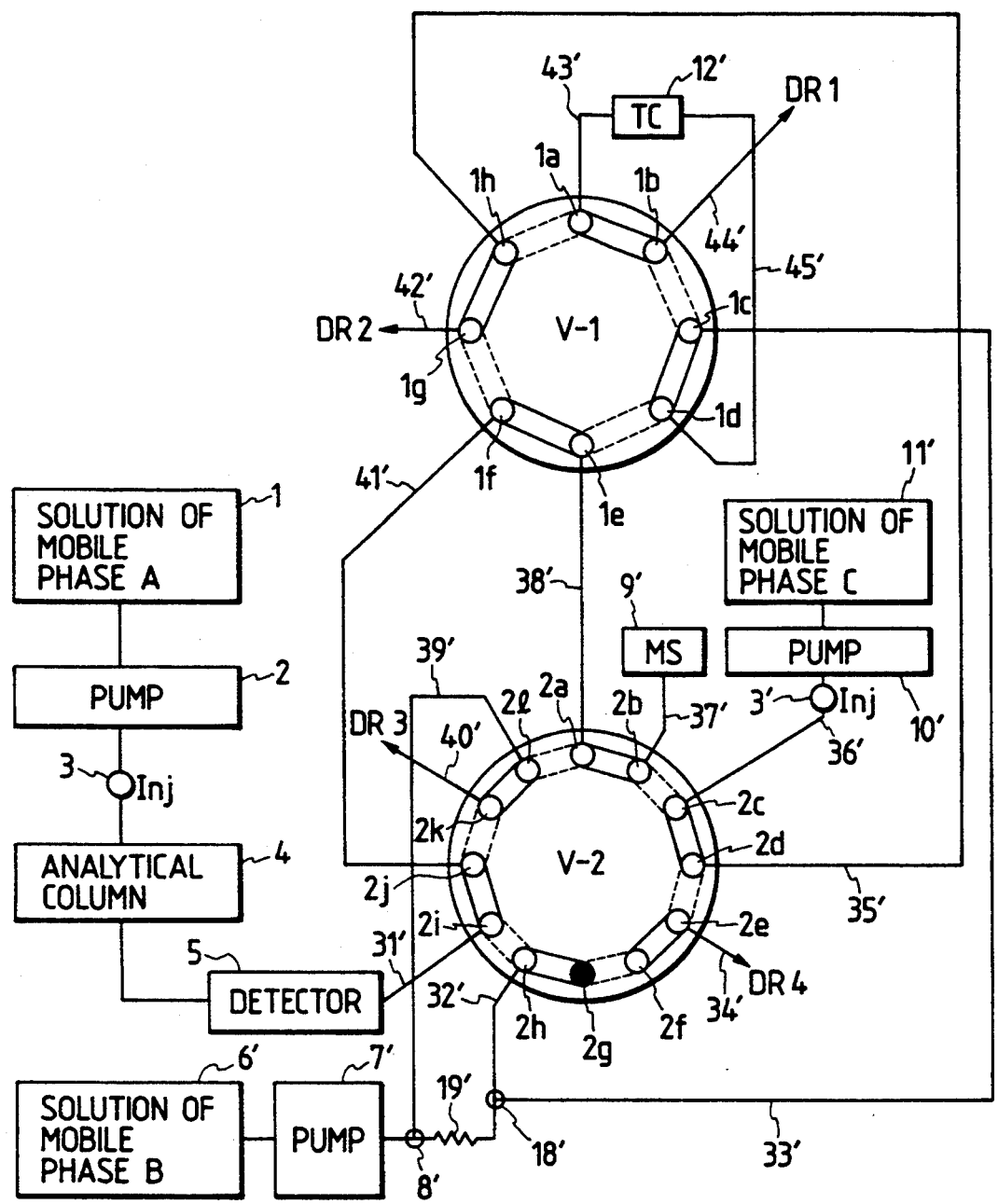
FIG. 26 is an embodiment of a LC/MS analytical system in the present invention.

FIG. 26 shows a practical embodiment of LC/MS analytical system in the present invention. FIGS. 27 to 30 show a characteristic four modes, that is, first, second, third and fourth analytical mode, in the LC/the MS analytical system.

Figure 31:
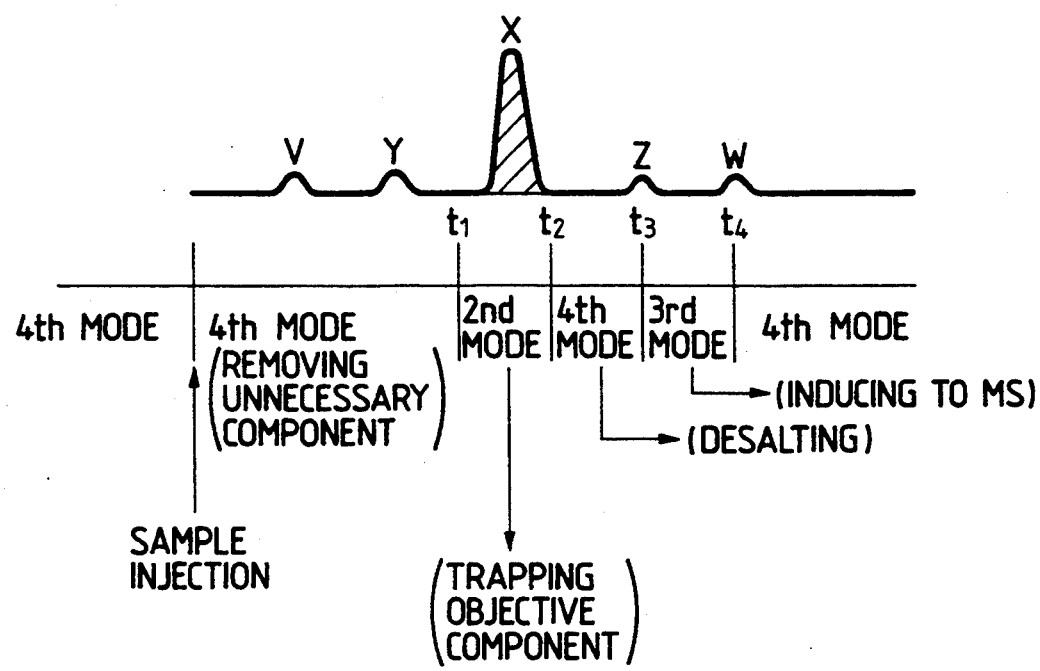
FIG. 31 is a schematic diagram for showing a change-over of the analytical mode in LC/MS by using nonvolatile solution of the mobile phase in the present invention.

FIG. 31 is a schematic diagram for showing a change-over of the analytical mode in LC/MS by using non-volatile solution of the mobile phase in the present invention.

Figure 32:
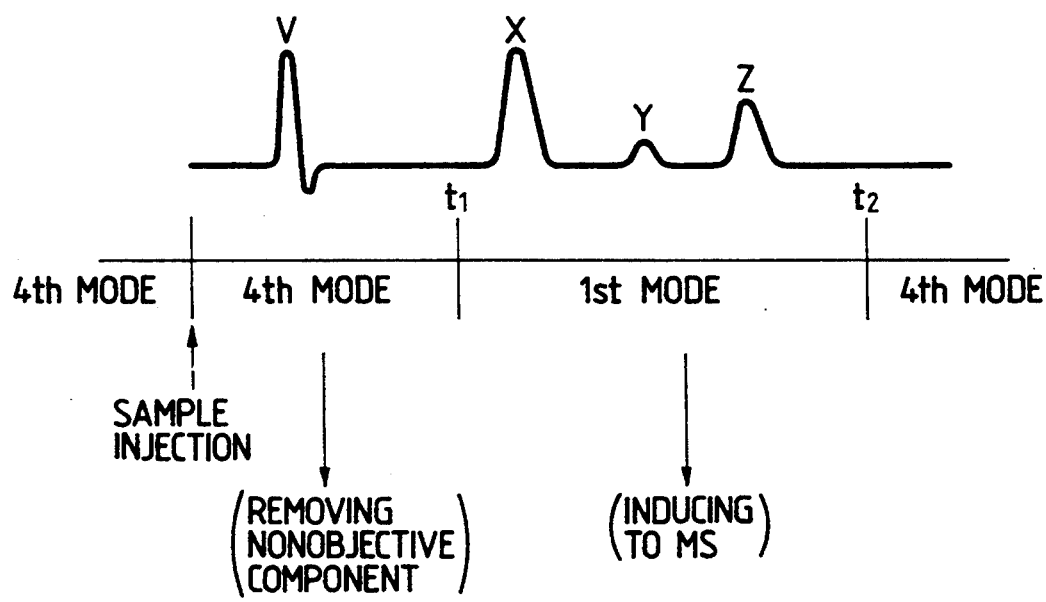
FIG. 32 is a schematic diagram for showing a change-over of the analytical mode in a case of front removing by using volatile solution of the mobile phase in the present invention.

FIG. 32 is a schematic diagram for showing a change-over of the analytical mode in a case of removing void volume component by using volatile solution of the mobile phase in the present invention.

Figure 33:
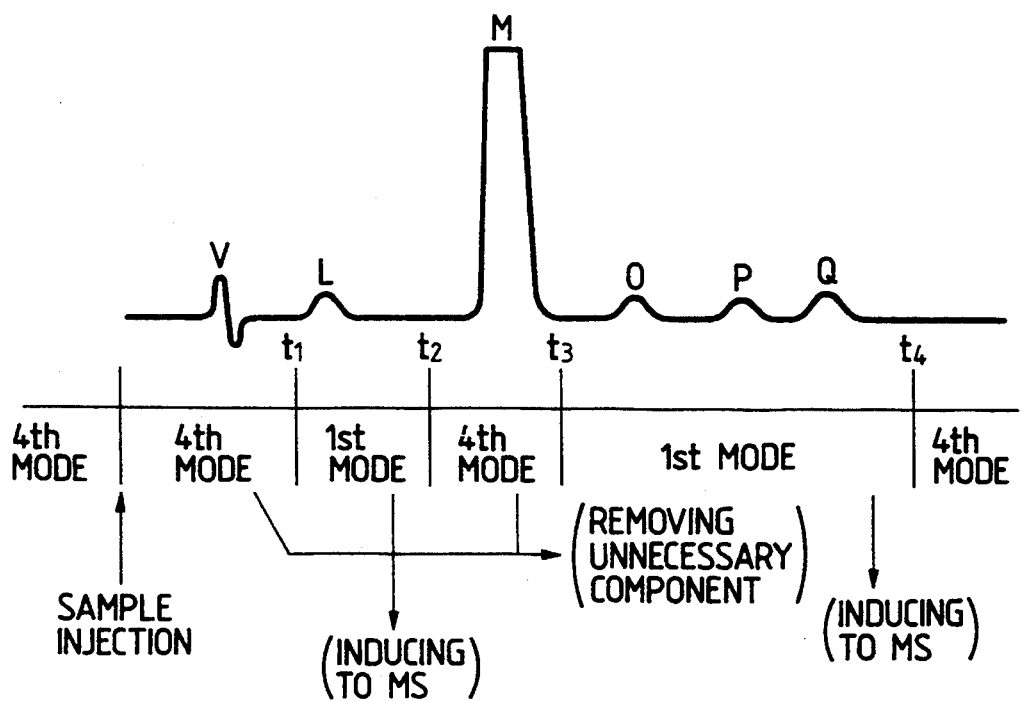
FIG. 33 is a schematic diagram for showing a change-over of the analytical mode in a case of removing components of non-interest in the present invention.

FIG. 33 is a schematic diagram for showing a change-over of the analytical mode in a case of removing components of non-interest in the present invention.

Figure 34:
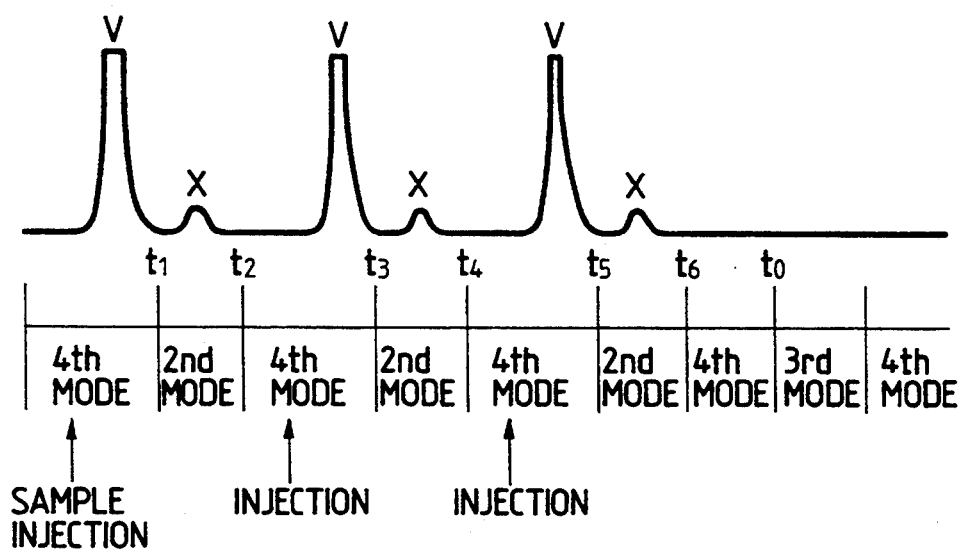
FIG. 34 is a schematic diagram for showing a change-over of the analytical mode in a case of a sample concentration by a repetition thereof in the present invention.

FIG. 34 is a schematic diagram for showing a change-over of the analytical mode in a case of a sample concentration by a repetition thereof in the present invention.

In FIGS. 26 to 30, numeral 6' means solution of the mobile phase A; 7', 10' respectively pumps; 8', 18' respectively tees; 9' an ion source of the MS; 11' solution of the mobile phase C; 12' a trapping column; 19' branched resistance column; DR1, DR2, DR3, DR4 respectively drains; V-1, V-2 multi-way change-over valves; 1a, 1b, 1c, 1d, 1e, 1f, 1g, 1h respectively ports of the valve V-1; 2a, 2b, 2c, 2d, 2e, 2f, 2g, 2h, 2i, 2j, 2k, 2l port of the valve V-2; 30' to 45' respectively thin tubes forming flow paths of the solutions connected between various constructive members.

As shown in FIG. 26, the solution 1 of the mobile phase A for being analyzed stored in an eluate storage chamber is transmitted by the pump 2. The sample solution is injected from the sample injection port 3 by syringe etc. and transmitted to the analytical column 4 in the solution 1 of the mobile phase A. The sample solution is eluted according to the components contained therein from the analytical column 4. The eluted components are detected by the detector 5 and transmitted to the port 2i through thin tube 31 and the valve V-2.

The thin tube may be any of a stainless tubes having a diameter from 0.1 to 1.0 mm, and preferably is a stainless tube having a diameter of 0.5 mm.

The valve V-1 is a eight way change-over valve and the valve V-2 is a twelve way change-over valve, of course, multi way change-over valve having more ports than eight or twelve ports may be used instead of them, and the valves V-1, V-2 are changed over by a motor controlled manually, by CPU or by LC controller (not shown in the figure). Flow paths changed over by the valves are alternately changed between a state I shown by solid lines and a state II shown by dotted lines.

As the system shown in FIG. 26 has two valves and each valve has two states I and II, the system are used in four states combined with the two states of the valves.

Then, the analytical modes (1), (2), (3), (4) of the system will be explained.

Figure 27:
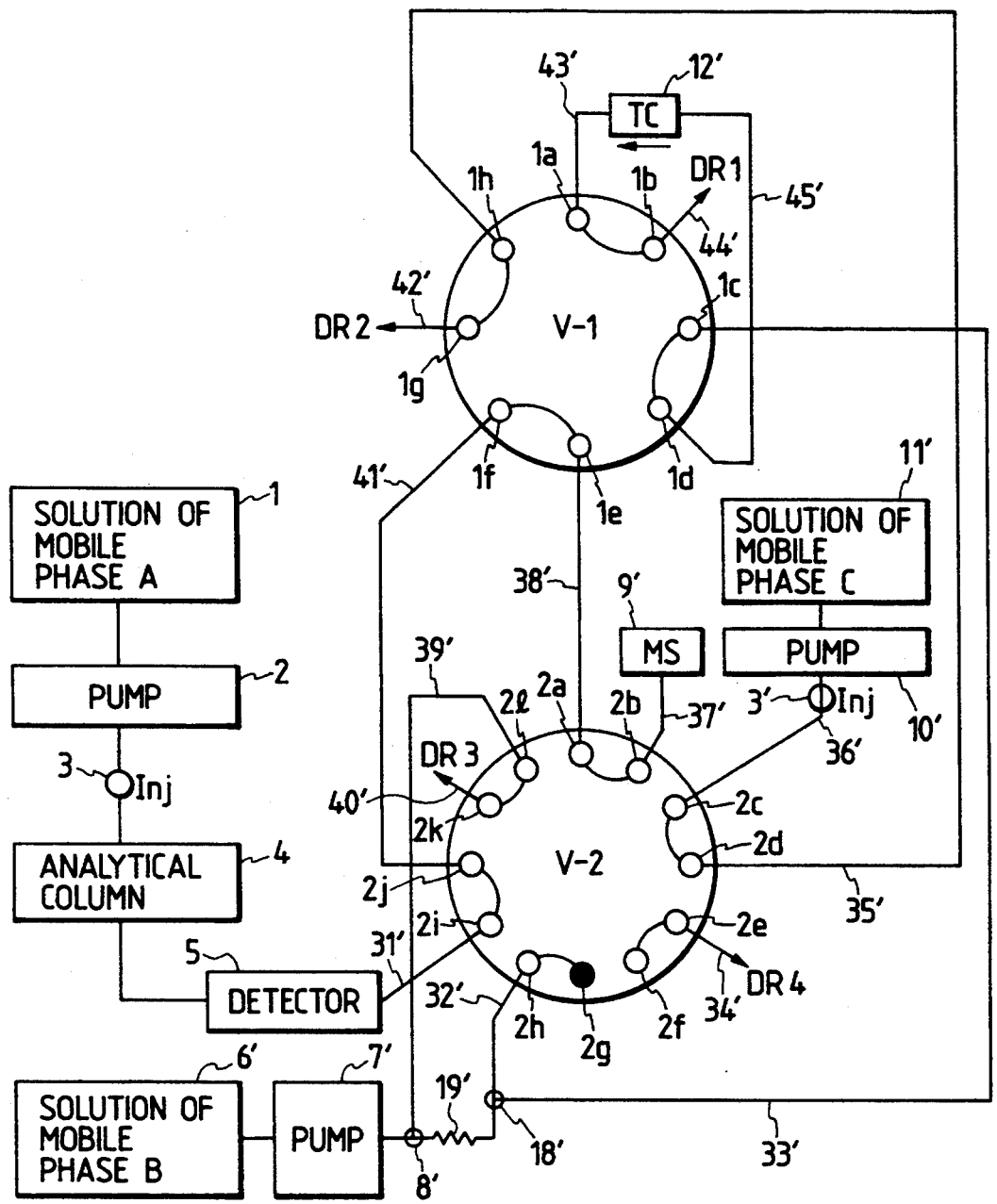
FIG. 27 is an embodiment of a first analytical mode of a LC/MS analytical system shown in FIG. 26 in the present invention.

(1) First analytical mode,

In this mode, the valve V-1 is in the state I and the valve V-2 is in the state I as shown in FIG. 27 in which connecting states between the every ports are shown by solid lines.

For example, the ports 1a and 1b of the valve V-1 are connected, but the ports 1a and 1h are not connected.

The eluate A eluted from the analytical column 4 is transmitted to the ion source 9' of the MS through a path of the detector 5 the thin tube 31' the ports 2i, 2j, the thin tube 41', the ports 1f, 1e, the thin tube 38', the ports 2a, 2b, the thin tube 37', and is ionized so as to finally provide a mass spectrum.

The solution 11' of the mobile phase C for eluting, which does not contain non-volatile salt, such as water and acetonitrile mixed with 1:9 ratio, for example, is transmitted by the pump 10' so as to be drained to the outside through a path of the thin tube 36', the ports 2c, 2d, the thin tube 35', the ports 1h, 1g, the thin tube 42', and the solution 11' of the mobile phase C is used for washing the flow paths in the first analytical mode.

The solution 6' of the mobile phase B such as water, for example, is transmitted to the tee 8' by the pump 7' so as to be branched, and the solution 6' in one path branched from the tee 8' is drained to the outside through the drain DR 3 through a path of the thin tube 39', the ports 21', 2k', the thin tube 40' and the solution 6' in other path branched from the tee 8' is further branched by the tee 18' after its flow rate has been limited by the branched resistance column 19.

The solution 6' in one path branched from tee 18' transmitted to the ports 2h, 2g through the thin tube 32', but stops at the port 2g as the port 2g is sealed. The other solution 6' in other path branched from the tee 18' flows into the trapping column 12' with a direction as shown by an arrow in the figure through a path of the thin tube 33', the ports 1c, 1d, the thin tube 45'.

The eluate D from the trapping column 12' is wasted to the outside through the drain DR1 through a path of the thin tube 43', the ports 1a, 1b. The flow rate between the flow paths 32' and 33' is adjusted by the branch resistance column 19' and it may be substituted by the needle valve.

As stated above, the eluate A is continuously transmitted to the ion source 9' of the MS so as to provide a mass spectrum. The trapping column 12' is washed by the solution 6' of the mobile phase B which flows in a direction as shown by an arrow in the figure and the solution 11' of the mobile phase C for eluting washes the flow paths.

(2) Second analytical mode,

In this mode, the valve V-1 is in the state I, and the valve V-2 is in the state II and the components of interest are trapped by the trapping column 12'.

Figure 28:
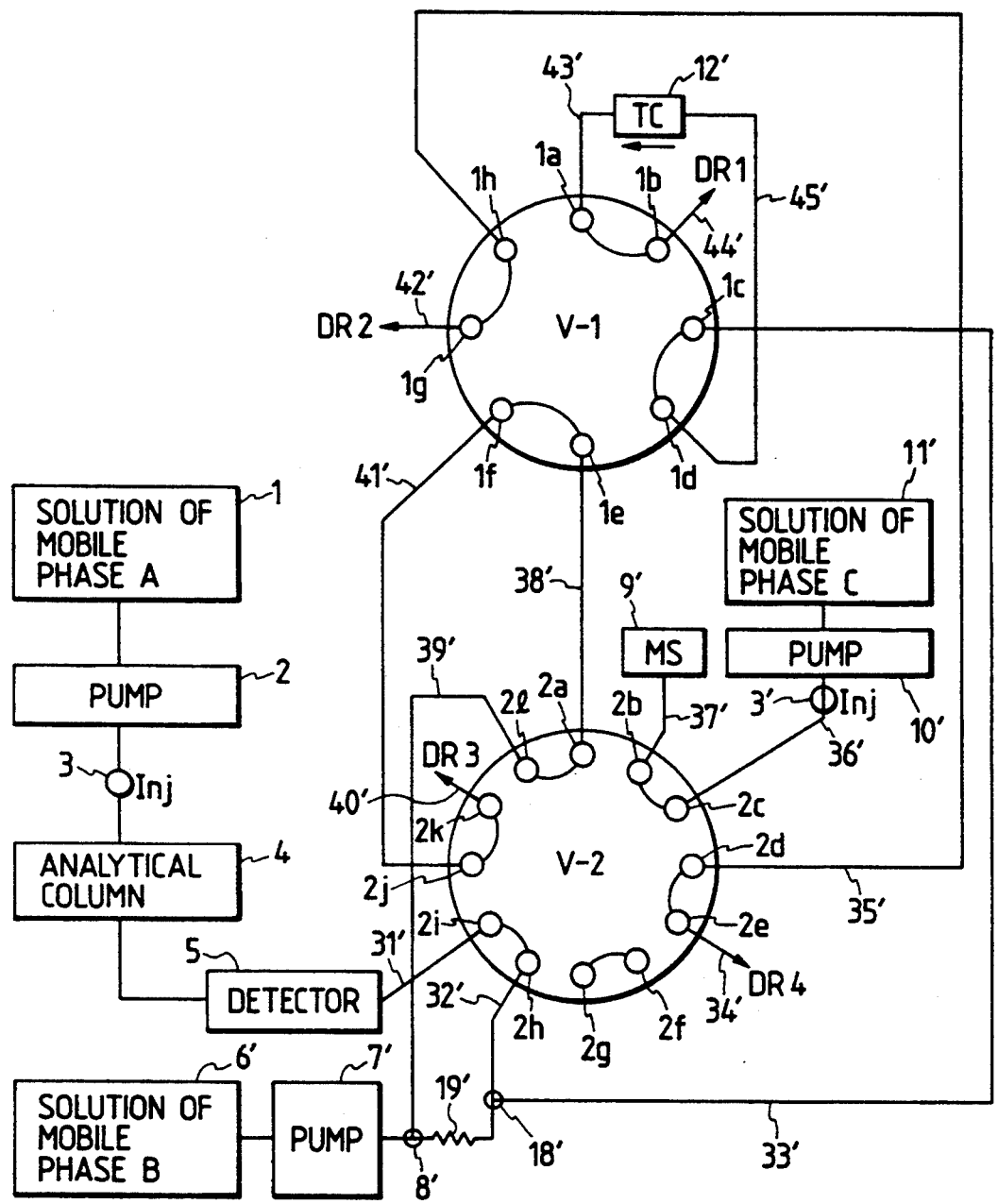
FIG. 28 is an embodiment of a second analytical mode of a LC/MS analytical system shown in FIG. 26 in the present invention.

In FIG. 28, the eluate A eluted from the analytical column 4 is transmitted to the thin tube 32' through a path of the detector 5, the thin tube 31', and ports 2i, 2h.

The solution 6' of the mobile phase B is mixed with the eluate A at the tee 18' through the branch resistance column 19' and dilute the eluate A so as to provided the confluenced eluate. The confluenced eluate is transmitted from the thin tube 33' to the valve V-1 and further transmitted to the trapping column 12' with a direction as shown by an arrow in the figure through the ports 1c, 1d, and the thin tube 45'.

The components of interest dissolved in the confluenced eluate are directly trapped with the trapping column 12'. The confluenced eluate other than trapped components is wasted to the outside through the drain DR 1 through the thin tube 43', and the ports 1a, 1b. The solution C of the mobile phase C for eluting which does not contain the non-volatile salt is transmitted to the ion source 9' of the MS by the pump 10', through a path of the thin tube 36, the ports 2c, 2b, the thin tube 37' and wash the ion source 9' of the MS and the flow path thereof.

The solution 6', of the mobile phase B from the path branched from the tee 8' is drained through a path of the thin tube 39', the ports 21, 2a, the thin tube 38', the ports 1e, 1f, the thin tube 41', the ports 2j, 2k, and the thin tube 40'.

As stated above, the components of interest eluted from the analytical column 4 are trapped by the trapping column 12', and the ion source 9' of the MS is washed by the solution 11' of the mobile phase C, and then the third analytical mode is applied. (3) Third analytical mode, In this mode, the valve V-1 is in the state II and the valve V-2 is in the state I and the components of interest trapped by the trapping column 12' in the second mode is eluted and thereafter introduced into ion source 9' of the MS.

Figure 29:
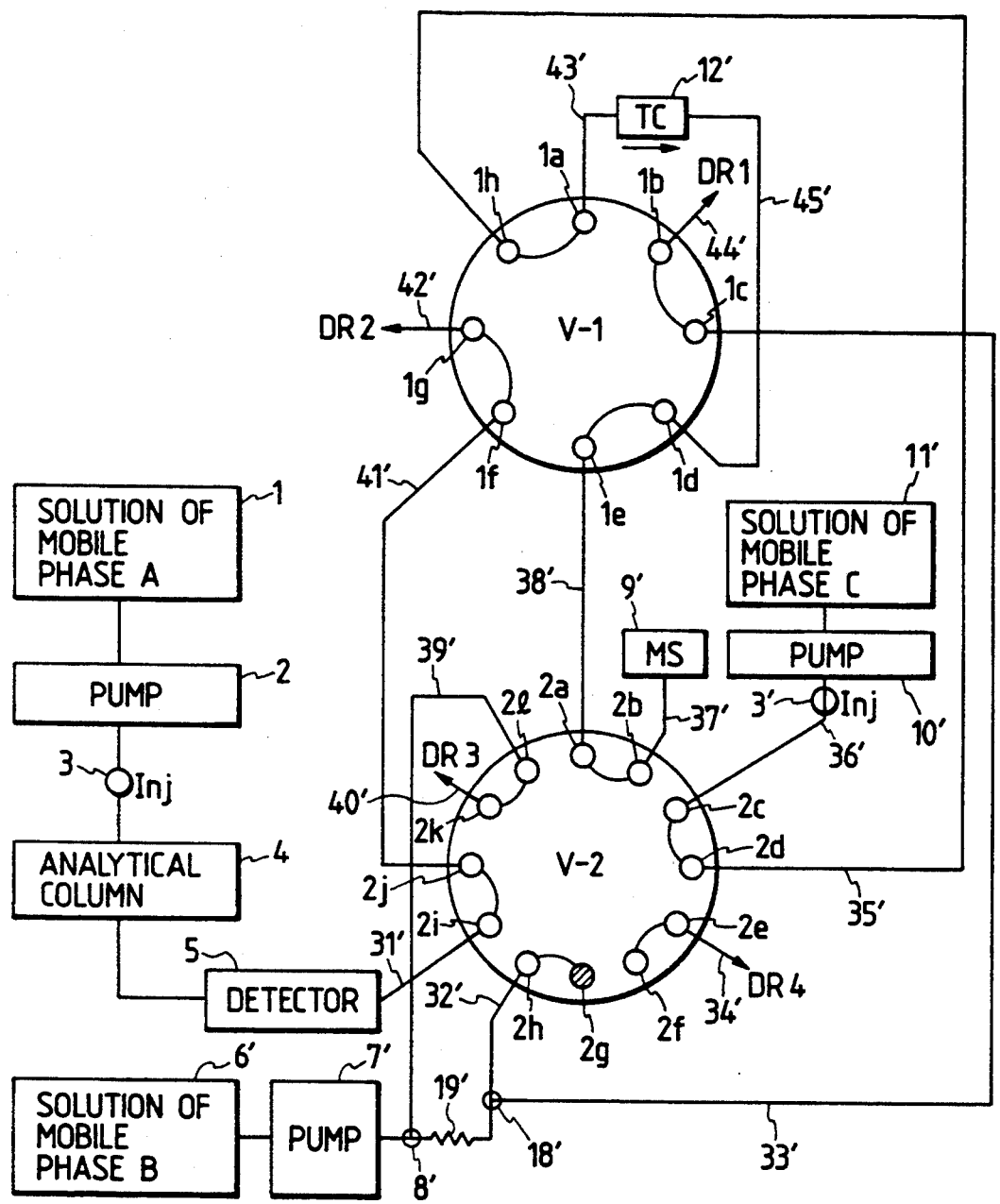
FIG. 29 is an embodiment of a third analytical mode of a LC/MS analytical system shown in FIG. 26 in the present invention.

In FIG. 29, the eluate A from the analytical column 4 is wasted to the outside through the drain DR 2 through a path of the ports 2i, 2j, the thin tube 41', the ports 1f, 1g, and the thin tube 42'.

The solution 11' of the mobile phase C for eluting which does not contain non-volatile salt is transmitted by the pump 10' and flows into the trapping column 12' with a direction as shown by an arrow in the figure through a path of the thin tube 36', the ports 2c, 2d, the thin tube 35', the ports 1h, 1a, and the thin tube 43'. The flow direction of the solution 11' of the mobile phase C in the third analytical mode is reverse to those of the solution 11' in the first and second modes.

The components of interest trapped in the trapping column 12' in the second analytical mode are eluted in a reverse direction to that in trapping, desalting and washing.

The eluate C, containing the eluted components of interest, is introduced to ion source 9' of the MS through a path of the thin tube 45', the ports 1d, 1e, the thin tube 38' the ports 2a, 2b, and the thin tube 37'. The analyte is ionized by the ion source 9' of the MS and a mass spectrum is provided.

The solution 6' of the mobile phase B is transmitted by the pump 7' and is branched by the tee 8'. The solution 6' in one path branched from the T tube 8' is wasted through the drain DR 3 through a path of the thin tube 39', the ports 2f, 2k and the solution 6' in other path branched from the T tube 8' is wasted through the drain DR 1 through a path of the branch resistance column 19', the tee 18', the thin tube 33', the ports 1c, 1b, and the thin tube 44'.

Therefore as stated above, the eluate A from the analytical column 4 is wasted to the outside, and the components of interest trapped in the trapping column 12' are eluted by the back-flush of the solution 11' of the mobile phase C. The analyte is introduced to the ion source 9' of the MS so as to provide a mass spectrum and the flow paths are washed by the solution 6' of the mobile phase B. (4) Fourth analytical mode, In this mode, the valve V-1 is in the state II and the valve V-2 is in the state II and the trapping column 12' and the ion source 9' of the MS are washed and the trapping column, if having trapped the component, is washed and desalted while the component is adsorbed onto the trapping column.

Figure 30:
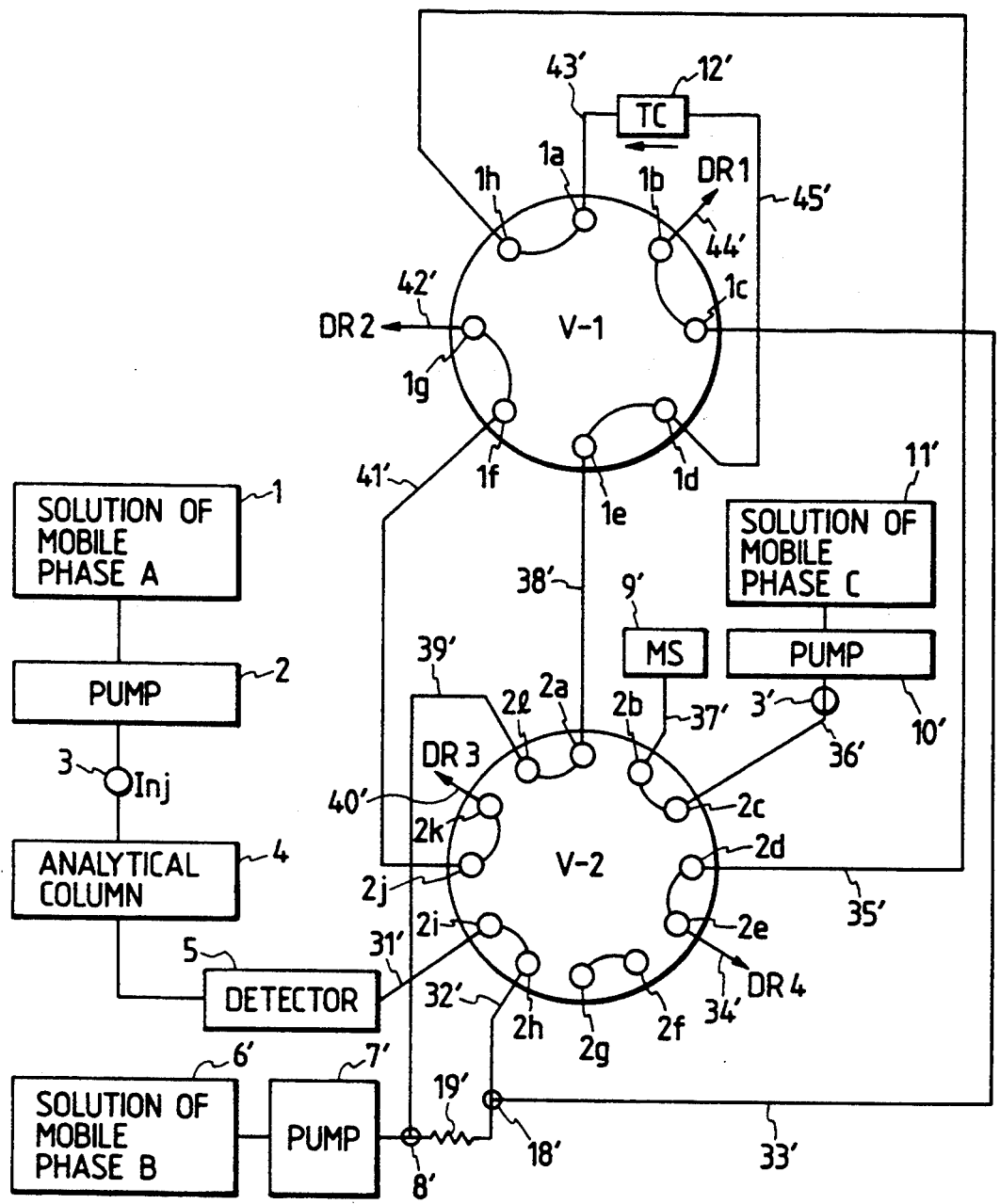
FIG. 30 is an embodiment of a fourth analytical mode of a LC/MS analytical system shown in FIG. 26 in the present invention.

In FIG. 30, the eluate from the analytical column 4 is transmitted to the tee 18' through a path of the thin tube 31', the ports 2i, 2h, the thin tube 32'.

The solution 6', of the mobile phase B is transmitted by the pump 7', and is branched at the tee 8'. The branched solution 6' is transmitted to the T shape tube 18' and is confluenced with the eluate A so as to dilute the eluate A. The confluenced solution is wasted to the drain DR 1 through a path of the thin tube 33', the ports 1c, 1b, and the thin tube 44'.

Further, the solution 6' of the mobile phase B in other path branched from the tee 8' flows into the trapping column with a direction shown by an arrow in the figure through the thin tube 39', the ports 21, 2a, and the thin tube 38', the ports 1e, 1d, and the thin tube 45'.

The eluate D from the trapping column 12' is wasted to the drain DR 4 through a path of the thin tube 43', the ports 1a, 1h, the thin tube 35', the ports 2d, 2e, the thin tube 34'. The solution 11' of the mobile phase C is transmitted by the pump 10' and wash the ion source 9' of the MS through a path of the thin tube 36', the ports 2c, 2b, the thin tube 37'.

Therefore as stated above, the eluate A from the analytical column 4 is wasted to the outside and the trapping column 12' is washed by the solution 6' of the mobile phase B flows in a forward direction and the ion source 9' of the MS is washed with the solution 11' of the mobile phase C which does not contain the nonvolatile salt. When the components of interest are trapped in the trapping column 12', the components of interest are washed without being eluted by selecting the appropriate polarity of the solution of the mobile phase B.

Next, various practical analysis will be explained by using the combinations of the above stated first, second, third and fourth modes referring to FIGS. 31 to 4.

(1) Process for introducing into the MS after desalting,

In FIG. 31, the chromatogram shown at the top thereof is a liquid chromatogram detected by the detector 5, and code X means a component of analyte and codes Y, Z, V, W mean analytical components of non-interest.

The analytical modes shown at the bottom of the figure changed by operating the valve shows the process from desalting to introducing to the MS.

The process from desalting the component of analyte X in order to measure using the LC/MS to introduce the component X to the MS will be explained hereinafter.

At first, before analyzing the solution, the trapping column 12' is processed in the fourth analytical mode by changing the valve for the pretreatment.

Then, the sample solution is injected and is kept in the fourth analytical mode till a time t1 just before the component X is eluted. While at that time, the components of non-interest V, Y eluted from the analytical column 4 are wasted to the outside with the eluate A and simultaneously trapping column 12' is washed with the solution 6' of the mobile phase B.

Then, on the time t1, the valve is changed so as to be in the second analytical mode. The component of interest X is trapped by the trapping column 12'. At a time t2 when the component X is finished eluting, the valve is changed so as to be in the fourth analytical mode.

It takes few minutes to perform the fourth analytical mode, practically from 3 to 5 minutes, and the trapping column 12' is washed and desalted by the solution 6' of the mobile phase B. While the desalting process is performed, the component is kept to be trapped in the column 12'.

Then, on the time t3, the valve is changed so as to be in the third analytical mode and the components X trapped in the column 12' is eluted by the back-flush of the solution 11' of the mobile phase C. The eluate C containing the component X is introduced to the ion source 9' of the MS so as to generate a mass spectrum.

On the time t4 when the component X is finished being introduced to the MS, the valve is changed so as to be in the fourth analytical mode again, and the trapping column 12' is washed with the solution 6' of the mobile phase B. In this fourth analytical mode, only the component X is trapped in the trapping column 12' and the mass spectrum is provided after desalting and eluting it. And all of the components of non-interest V, Y, Z, W are wasted to the outside.

(2) Process in the LC/MS by the solution of the mobile phase which does not contain the non-volatile salt, In FIG. 32, the chromatogram shown at the top thereof is a liquid chromatogram detected by the detector 5, and the four components denoted V, X, Y, Z are successively eluted from the analytical column 4. The components X, Y, Z are the analytes and the component V is the component of non-interest eluted by the void volume.

The changing over of the analytical mode by the valve changing operation shown at the bottom of FIG. 32 shows the removal of components eluted by the void volume.

In the case of reversed-phase chromatography, ionic compounds, salts and compounds with high polarity are generally not held in the analytical column and are eluted by the voided volume. Such chemical compounds may plug the ion sampling aperture and the ion source 9' of the MS may be contaminated when these components are introduced into the ion source 9'.

If a mass-spectrum of the components is obtained, it is the mass-spectrum relating to the mixture thereof and does not offer any useful information. Therefore, by removing the components eluted by the void volume and keeping the ion source 9' free from contamination, the ion source 9' is kept clean for a long time and capable of providing useful information.

In FIG. 33, L represents a component of analyte, O, P, Q represent trace components, V represents a component eluted by the void volume and the M, V are commonly the components of non-interest.

In the case of analyzing impurities, after the main component M is introduced into the ion source 9', the trace components O, P, Q may not be detected because of the carry-over of the component M. When the contaminating components such as M above are frequently introduced in the ion source 9', the contamination of the ion source 9' is occurs easily so as to make frequent cleaning necessary. In order to improve such problem, the contaminating components such as M should be wasted to the outside without being introduced into the ion source 9'.

In FIGS. 32, 33, the component V eluted by the voided volume and the contaminating components of no interest are wasted to the outside in the fourth analytical mode. At this time, the ion source of the MS is flushed with the solvent, that is, the solution 11' of mobile phase C so as to be washed and the ionization of the ion source 9' is prevented from being unstable.

After eluting the components of non-interest M, V, the first analytical mode is provided and the eluate A from the analytical column 4 is introduced into the ion source 9' and the mass spectrum is obtained. In the case the trapping time of the component of non-interest is known, the first analytical mode may be provided based on the trapping time.

Referring to FIG. 32, the removing of the component V eluted by the void volume will be explained.

At first, the fourth analytical mode is provided, and the sample solution is injected through the sample injection port 3. The fourth analytical mode is provided and the eluted components of non-interest are wasted to the outside until time t1.

Then, the first analytical mode begins at time t1 and the eluate A is directly introduced into the ion source 9' of the MS. The components of interest X, Y, Z are successively ionized thereby providing the mass spectra corresponding thereto. Further, the fourth analytical mode begins at time t2, the LC/MS finishes measuring and preparation of the washing of the columns and the following analysis are performed.

In FIG. 33, examples such as the components eluted by the void volume and the contaminating components of non-interest are shown.

The fourth analytical mode begins and the sample solution is injected. The fourth analytical mode is held till time t1 and the component of non-interest V is wasted.

At time t1, being changed to the first analytical mode, the component of analyte L is measured.

At time t2 just before the main component M is eluted, the fourth analytical mode is started and is performed until time t3 when the elution of the main components finishes, and the main component M is wasted to the outside.

At the time t3, the first analytical mode is again started and the components of interest O, P, Q are measured. At the time t4, the fourth analytical mode is started and the preparation for the next measurement is performed.

As explained above, the first and fourth analytical modes are selectively and repeatedly performed, and the introduction and removal of the components to the ion source 9' separated by the LC are easily performed.

(3) Process for FIA,

In the case of analyzing pure compounds, it is enough to get these mass spectra. In this case, it is not necessary to separate by using the analytical column. Sometimes, the FIA is convenient and is used in selecting a kind of the ionization of the sample solution such as APCI and ESI, optimizing of the ionizing condition and selecting a positive or negative ionizing mode.

The FIA system is obtained by providing an injection port 3' at a portion of the flow paths of the solution 11' of the mobile phase C as shown in FIG. 30.

As shown in FIG. 30, when the fourth analytical mode is set, the analytical column 4 is always washed with the solution 1 of the mobile phase A and the trapping column 12' is washed with the solution 6' of the mobile phase B and further the ion source 9' of the MS is washed with the solution 11' of the mobile phase C. The sample solution is repeatedly transmitted to the ion source 9' of the MS from the injection port 3' through the thin tube 36' so as to obtain the mass spectrum easily and in a short time.

In the second analytical mode shown in FIG. 28, the FIA may be performed in the same way as above. But, in the second analytical mode, eluate A from the analytical column 4 is diluted by the solution 6' of the mobile phase B and flows into the trapping column 12'.

In the fourth analytical mode, the analytical column and the trapping column are operated in the different paths and there is no relation therebetween. Therefore, the fourth analytical mode is suitable for FIA.

(4) Process for analyzing by concentrating the components of interest,

When measuring by the LC/MS, the low concentration of the components of interest makes it difficult to measure them accurately.

Referring to FIG. 34, such process for concentrating the components will be explained.

At first in the LC/MS, the sample solution is injected in the fourth analytical mode. At time t1 just before the component of analyte is eluted, the second analytical mode is started, the trapping column 12' traps the component of analyte X. At time t2 when the elution of the component of interest X is finished, the fourth analytical mode is changed to be processed. After the elution of all the components except the components of interest is finished, the sample solution is again injected.

As explained above, the fourth and second analytical modes are alternately repeated so as to repeat the injection of the sample solution, the components of interest X is repeatedly trapped in the trapping column 12', and is concentrated. At the time t0 when the trapping and the concentration of the component of interest X are finished, the component of analyte X is eluted by back-flush and introduced to the ion source 9' of the MS.

By repeating the injection of the sample solution, the band-width of the component of analyte X trapped in the trapping column becomes many times broader than observed when trapping once, but, the broadening of the bandwidth may be fully suppressed by considering the kind and length of the trapping column 12', polarity of the solution of the mobile phase B, and dilution ratio. The elution by the back-flush has an effect to cancel the broadening of the band-width.

As explained above, the valve operation as above makes it possible to desalt and analyze the sample solution, analyze the solution of the mobile phase which does not contain the non-volatile salt and removing the components of non-interest, analyzing by FIA, and concentrating the trace components.

EXAMPLE 9

Further, another embodiment of the LC/MS using three sets of six way change-over valves in the present invention will be explained. FIGS. 35 to 38 show a analysis system of the LC/MS in the present invention.

In FIGS. 35 to 38, V-1, V-2, V-3 mean six way valves; 3a, 3b, 3c, 3d, 3e, 3f mean ports of the six way change-over valve V-3; 80', 81', 82', 83', 84', 85', 86', 87', 88', 89' mean thin tubes.

Figure 35:
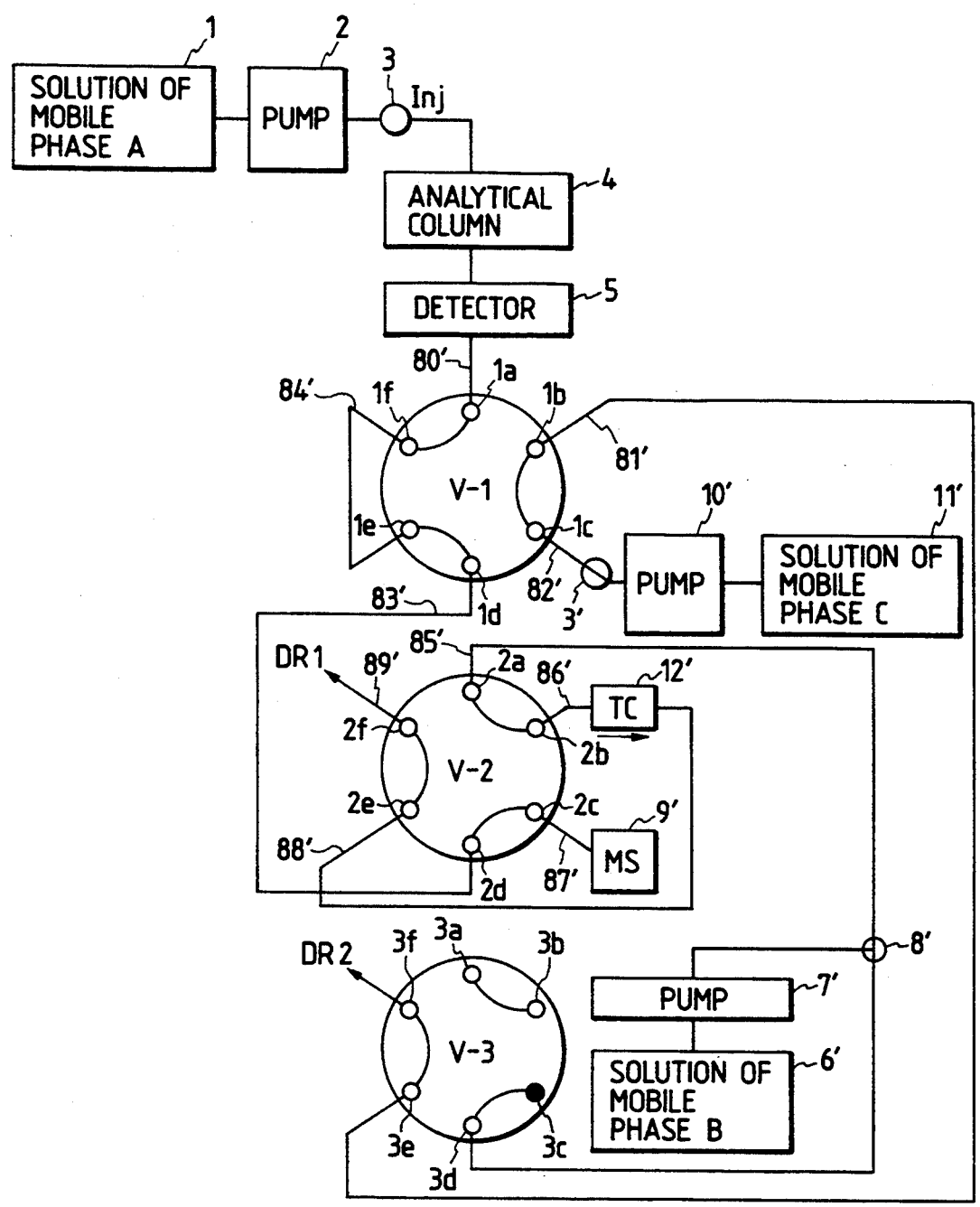
FIG. 35 is another embodiment of a first analytical mode of a LC/MS analytical system of the present invention.

The system shown in FIG. 35 corresponds to the first analytical mode in the above example 8.

The solution 1 of the mobile phase A is transmitted by the pump 2. The sample solution injected from the sample injecting port 3 is separated by the analytical column 4 according to the components thereof and is detected by detector 5.

Eluate A containing the analytes passing through the detector 5 is introduced into the ion source 9' of the MS through the thin tube 80' through a path of the ports 1a, 1f of the valve V-1, the thin tube 84', ports 1e, 1d, the thin tube 83' the ports 2d, 2c of the valve V-2, the thin tube 87'. At this time, the trapping column 12' is washed by the solution 6 of the mobile phase B transmitted by the pump 7 through a path of the tee 8', the thin tube 85', the ports 2a, 2b, the thin tube 86' with a direction shown by an arrow in the figure. The port 3c in the valve V-3 is sealed.

In the first analytical mode, the components of interest eluted from the analytical column 4 are directly introduced into the ion source 9' of the MS so as to analyze them.

Figure 36:
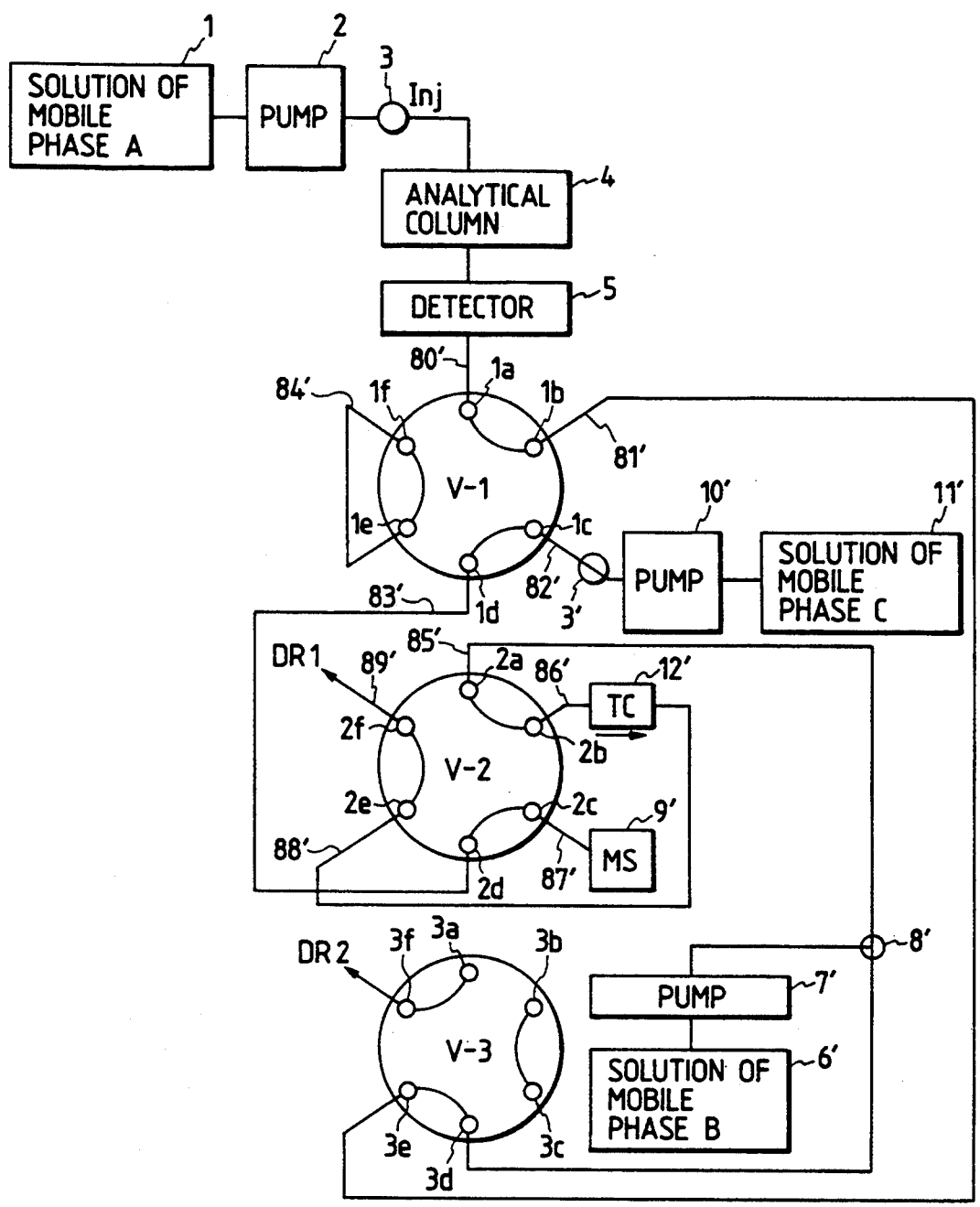
FIG. 36 is another embodiment of a second analytical mode of a LC/MS analytical system of the present invention.

The system shown in FIG. 36 corresponds to the second analytical mode in the above example 8.

The eluate A containing the components of interest eluted from the analytical column is transmitted to the thin tube 85' through the ports 1a, 1b of the valve V-1, the thin tube 81', ports 3e, 3d of the valve V-3. Further, eluate A is confluenced with the solution 6' of the mobile phase B at the tee 8' on the way to the thin tube 85' and diluted by the solution 6' of the mobile phase B. The confluenced solution flows into the trapping column 12' through a path of ports 2a, 2b of the valve V-2, the thin tube 86' with a direction shown by an arrow in the figure.

The eluate B containing the components which is not trapped in the trapping column TC is wasted to the outside through the drain DR 1 through a path of the thin tube 88', ports 2e, 2f, the thin tube 89'. All the while, the ion source 9' of the MS is washed with the solution 11' of the mobile phase C transmitted by the pump 10' through a path of the thin tube 82', ports 1c, 1d, the thin tube 83', ports 2d, 2c, and the thin tube 87'.

In the second analytical mode, the components of interest eluted from the analytical column 4 are trapped by the trapping column 12'.

Figure 37:
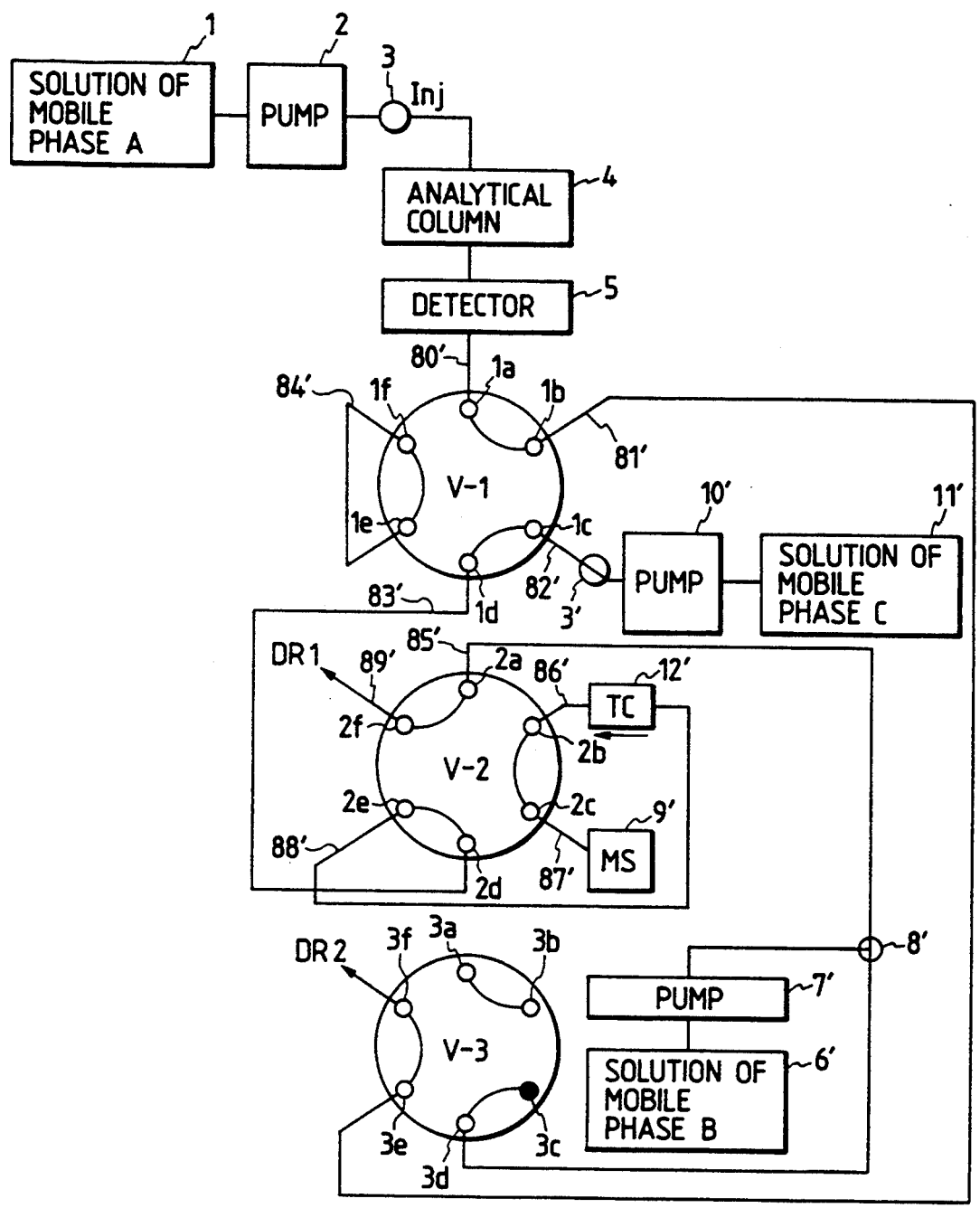
FIG. 37 is another embodiment of a third analytical mode of a LC/MS analytical system of the present invention.

The system shown in FIG. 37 corresponds to the third analytical mode in the above example 8.

The solution 11' of the mobile phase C is transmitted by the pump 10' to the valve V-1. Then, the solution 11' is transmitted to the valve V-2 through the ports 1c, 1d, the thin tube 83' and further to the trapping column 12' through a path of the ports 2d, 2e, and the thin tube 88 with a direction as shown by an arrow in the figure.

The analytical components trapped by the solution 11' of the mobile phase C is eluted by the back-flush. The eluate C containing the analytical components is transmitted to the valve V-2 through the thin tube 86' and then transmitted to the ion source 9' of the MS through a path of the ports 2b, 2c, the thin tube 87'. All the while, the eluate A from the analytical column 4 is wasted to the outside through a path of the detector 5, the thin tube 80', ports 1a, 1b, the thin tube 81', ports 3e, 3f.

In the third analytical mode, the analytical component trapped in the trapping column 12' is eluted by the back-flush and is introduced to the ion source of the MS so as to provide the mass spectrum.

Figure 38:
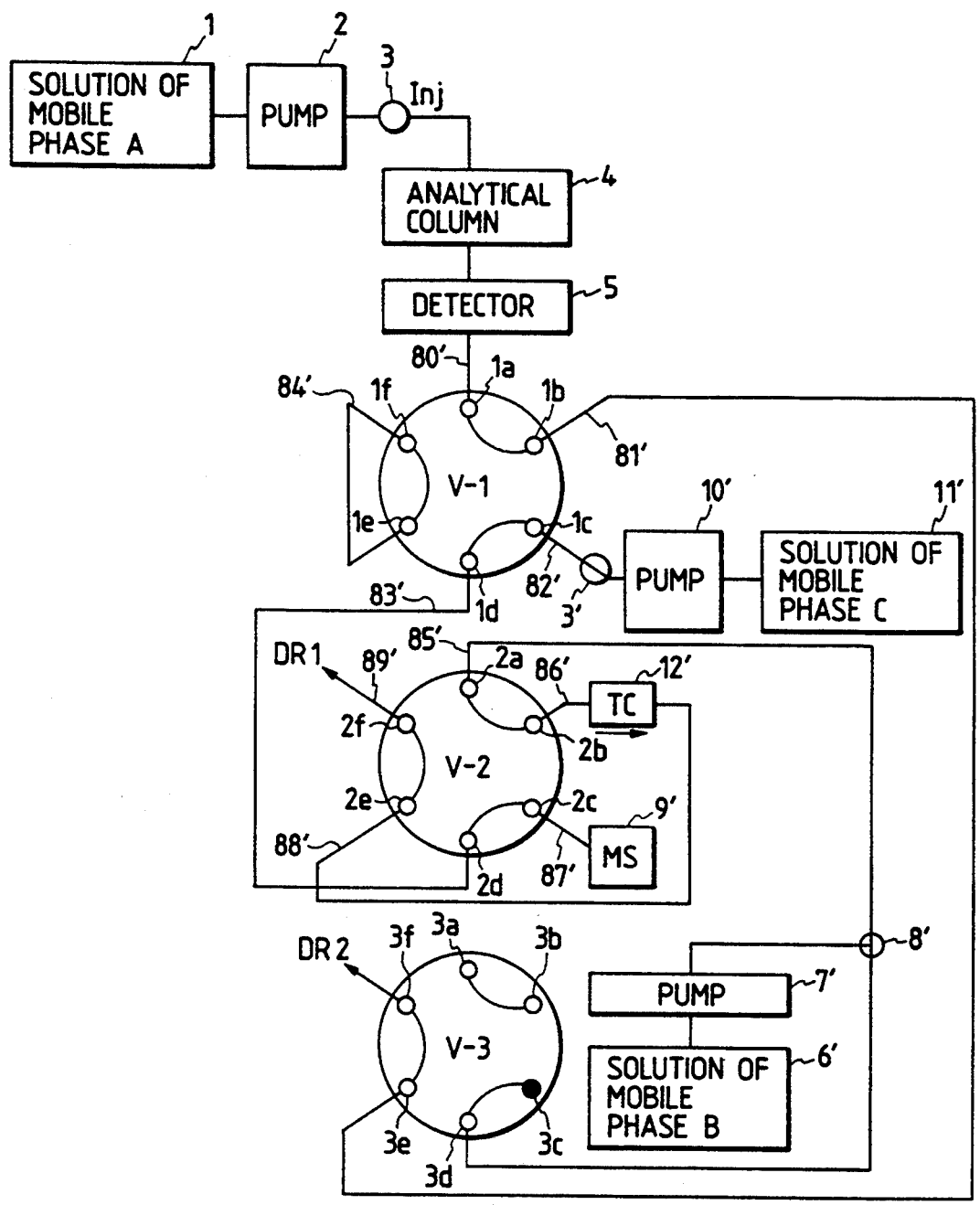
FIG. 38 is another embodiment of a fourth analytical mode of a LC/MS analytical system of the present invention.

The system shown in FIG. 38 corresponds to the fourth analytical mode in the above example 8.

The solution 6' of the mobile phase B is transmitted to the valve V-2 by the pump 7' from the tee through the thin tube 85. The port 3c of the valve V-3 is sealed. Further, the solution 6' of the mobile phase B washes the trapping column 12' by flowing through a path of ports 2a, 2b, and the thin tube 86' with a direction shown by an arrow in the figure. The eluate D from the trapping column 12' is drained through a path of the thin tube 88', ports 2e, 2f, the thin tube 89'.

The solution 11 of the mobile phase C is transmitted to the ion source 9' of the MS by the pump 10' through a path of the thin tube 82', ports 1c, 1d, the thin tube 83', ports 2d, 2d, and the thin tube 87'. Thereby the ion source 9' of the MS is washed.

In this analytical mode, the trapping column 12' may be washed and the desalting of the analytical component trapped in the column may be accomplished too.

In the example 9, the second, third and the fourth modes are changed-over in the same way as the example 8, thereby it becomes possible to trap and desalt the components of interest from the analyzing system containing the non-volatile salts, and introduce only the components of interest into the MS directly.

Further, the FIA is performed in the same way by providing a sample injection port 3' on the thin tube 82 of the flow path for the solution 11' of the mobile phase C and by injecting the sample solution in the fourth analytical mode.

EXAMPLE 10

Further, another embodiment of the LC/MS using two sets of sixteen way change-over valves in the present invention will be explained.

FIGS. 39 to 42 show explanatory views of a system of the LC/MS in the present invention.

In FIGS. 39 to 42, codes V-1, V-2 mean sixteen way change-over valves; 1a, 1b, 1c, 1d, 1e, 1f, 1g, 1h, 1i, 1j, 1k, 1l, 1m, 1n, 1o, 1q ports of the sixteen way change-over valve V-1; 2a, 2b, 2c, 2d, 2e, 2f, 2g, 2h, 2i, 2j, 2k, 2l, 2m, 2n, 2o, 2q ports of the sixteen way change-over valve V-2; 50' to 73' the thin tubes.

The four modes of the first, second, third and fourth modes may be applied in the same way as in the examples 8 and 9.

In this example 10, the sample injection port 3 becomes independent from the analytical column 4 at the fourth analytical mode, and the FIA may be possible by using the sample injection port 3. That is, the difference between this example and the examples 8 and 9 is that the sample injection port 3 for separating the components in the LC and the sample injection for FIA are the same one.

Such construction is useful in the case of a large system such as an auto-sampler which is a large sample injection system because there is no need to change distributing tubes for the solution.

Figure 39:
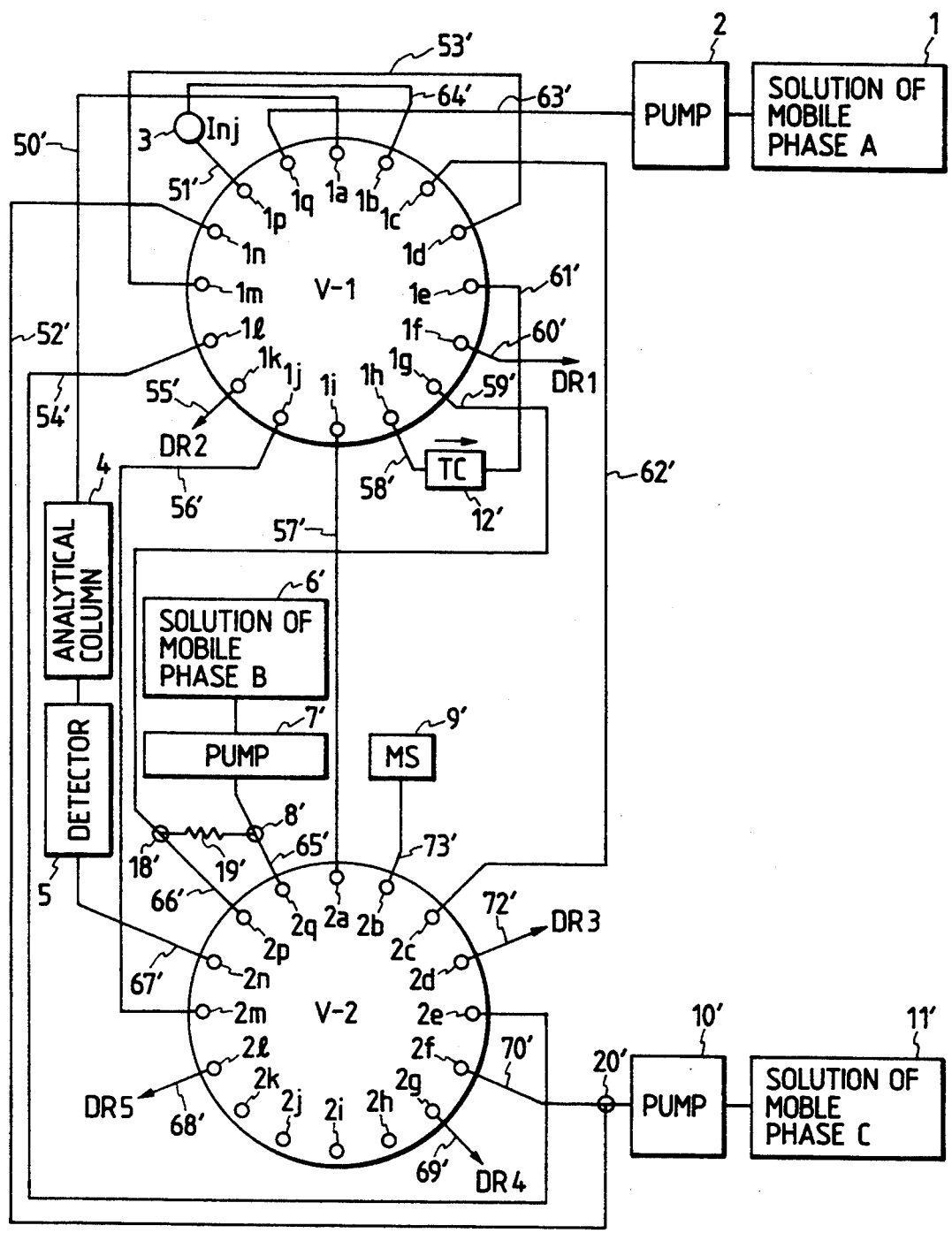
FIG. 39 is a further embodiment of a first analytical mode of a LC/MS analytical system of the present invention.

FIG. 39 corresponds to first analytical mode.

The solution 1 of the mobile phase A is transmitted to the sample injection port 3 by the pump 2 through a path of the thin tube 63', ports 1q, 1p of the valve V1, and the thin tube 51'. The sample solution is injected from the sample injection port 3 and flows into the analytical column 4 through a path of the thin tube 64', ports 1b, 1a, and the thin tube 50'.

The sample solution is eluted from the analytical column 4 according to the components thereof and after the components in the eluate A from the column 4 are detected by the detector 5, the components again flow into the valve V-1 through a path of the ports 2n, 2m of the valve V-2, and the thin tube 56'.

Further, the components again flow into the thin tube 57' of the valve V-2 through a path of ports 1j, 1i, and are introduced into the ion source 9' of the MS through a path of ports 2a, 2b, and the thin tube 73'.

The solution 6' of the mobile phase B is transmitted by the pump 7' and is divided at the tee 8' to a branched solution flow through a path of the thin tube 65', ports 2q, 2p, the thin tube 66' and a branched solution flows through the branched resistance column 19', and the two branched solution are confluenced again at the tee 18'. The confluenced solution 6' of the mobile phase B washes the trapping column 12' flowing through a path of the thin tube 59', ports 1g, 1h, and the thin tube 58' with a direction shown by an arrow in the figure.

After washing, the eluate D is wasted to the outside through the drain DR 1 through a path of the thin tube 61', ports 1e, 1f, and the thin tube 60'. The solution 11' of the mobile phase C is transmitted by the pump 10' and is branched at the tee 20'. One of the t paths branched the T shape tube 20' is transmitted to the valve V-1 through a path of the thin tube 70', ports 2f, 2e, and the thin tube 54', and wasted to the drain DR 2 through ports 1e, 1k, and the thin tube 55'. Other of the branched paths is wasted through the drain DR 3 i ports 1n, 1m, the thin tube 53', ports 1d, 1c, the thin tube 62', and ports 2c, 2d.

In the first analytical mode, the eluate A from the analytical column 4 is directly fed to the ion source 9' of the MS and all the while the trapping column 12' and the thin tube are washed by the solvent.

Figure 40:
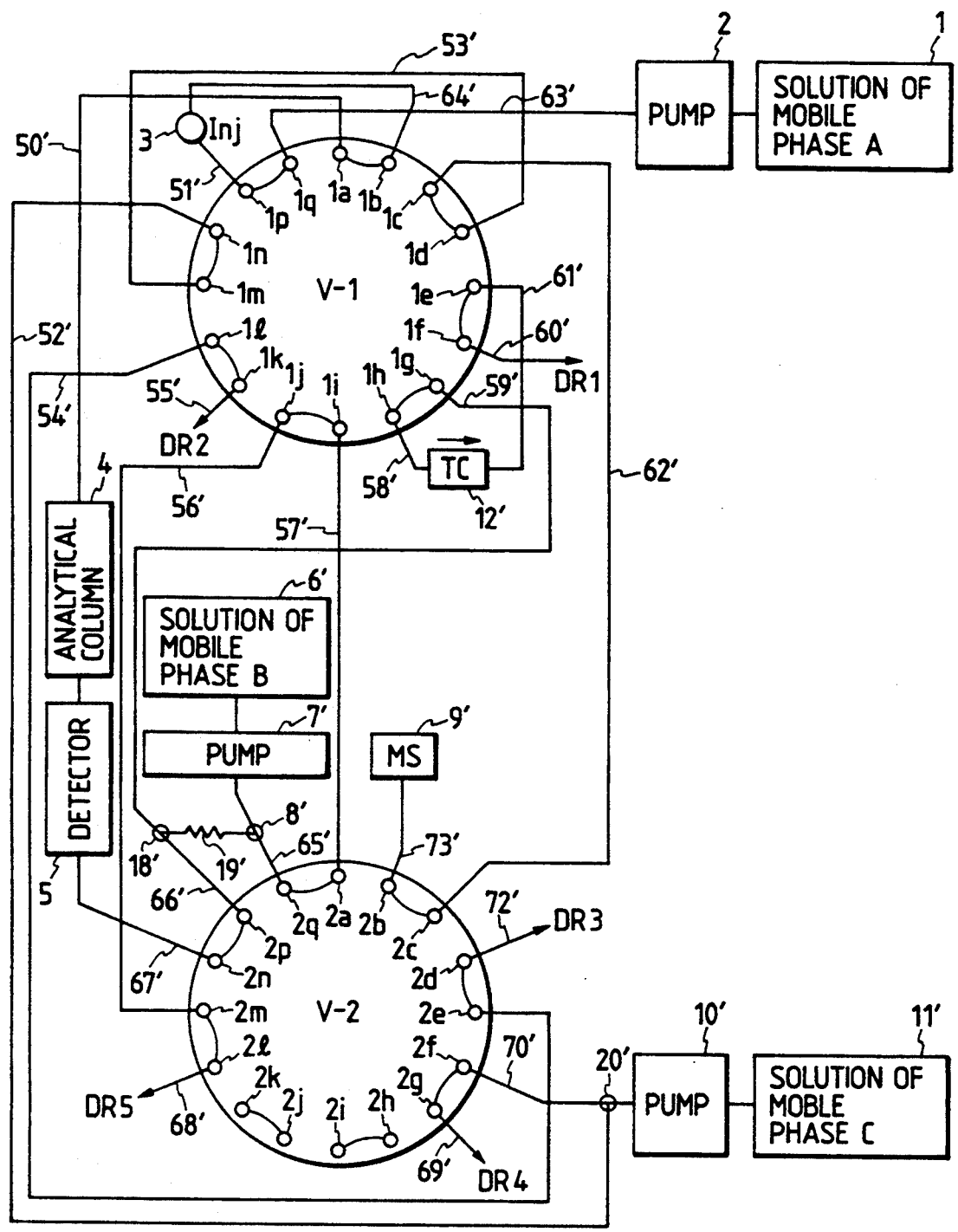
FIG. 40 is a further embodiment of a second analytical mode of a LC/MS analytical system of the present invention.

FIG. 40 corresponds to the second analytical mode.

The eluate eluted from the analytical column 4 flows into the tee 18' through a path of the ports 2n, 2p of the valve V-2, and the thin tube 66'. The solution 6' of the mobile phase B is transmitted by the pump 7' through the tee 8', and the branched resistance column 19' and confluenced with the eluate A at the tee 18'. The confluenced solution flows from the thin tube 58 to the trapping column 12' through the thin tube 59', and the ports 1g, 1h with a direction shown by an arrow in the figure.

After the component of analyte is trapped by the trapping column 12', the eluate B which contains non-trapped components is wasted through the drain DR 1 to the outside through a path of the thin tube 61', the ports 1e, 1f, and the thin tube 60'.

The solution 11' of the mobile phase C is transmitted by the pump 10' and divided into two paths at the tee 20'. The solution 11 of the mobile phase C in one of the two paths is wasted through the drain DR 4 to the outside through a path of the thin tube 70', ports 2f, 2g, and the thin tube 69'. The solution 11' in other of the paths is transmitted to the valve V-1 through the thin tube 52' and further transmitted to ion source 9' of the MS through a paths of the 1n, 1m, thin tube 53', ports 1d, 1c, the thin tube 62', ports 2c, 2b, and the thin tube 73'.

The analytical component from the analytical column 4 is trapped by the trapping column 12' in the second analytical mode and all the while, the ion source 9' of the MS is washed with the solution of the mobile phase C.

Figure 41:
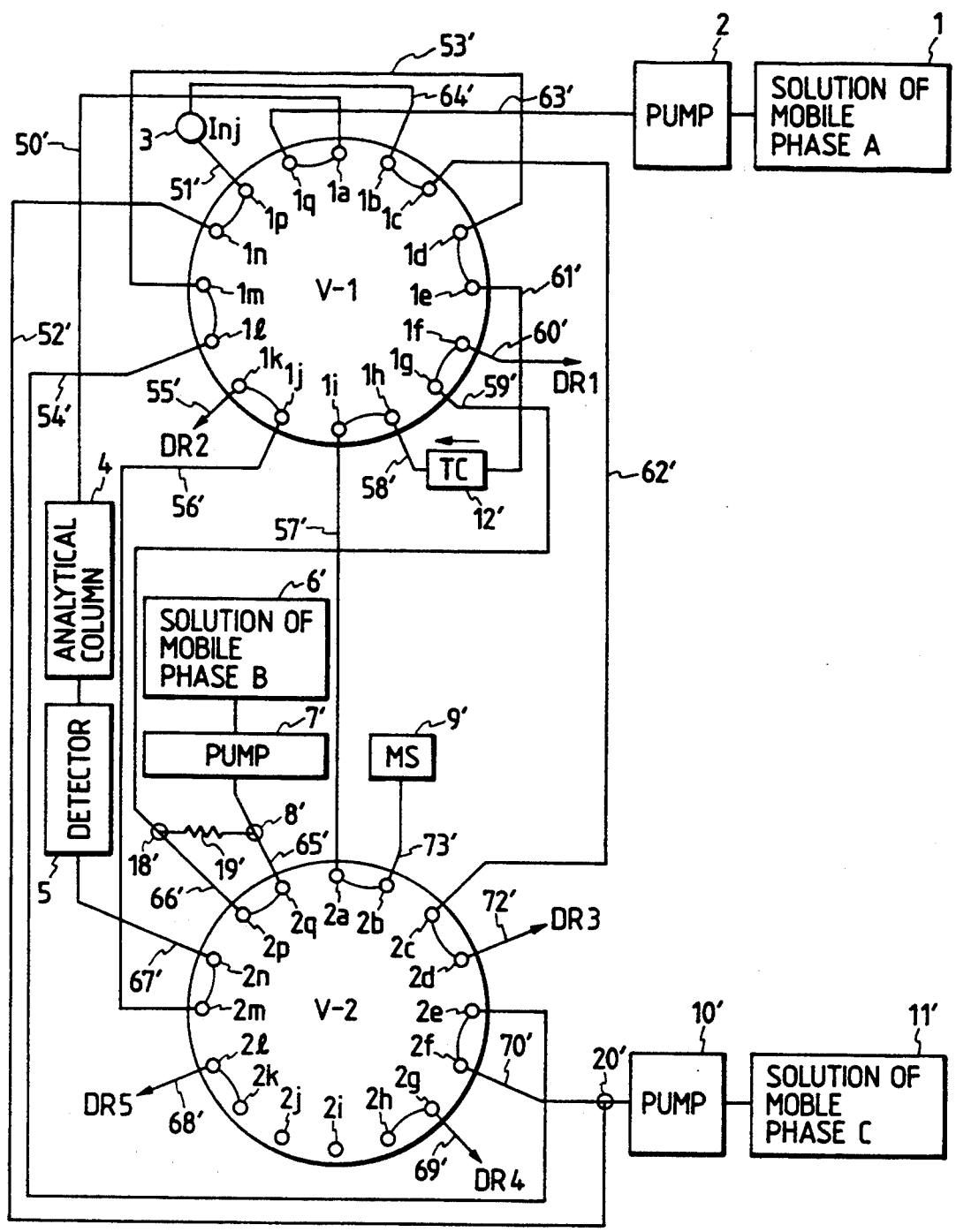
FIG. 41 is a further embodiment of a third analytical mode of a LC/MS analytical system of the present invention.

The system shown in FIG. 41 corresponds to the third analytical mode.

The eluate A eluted from the analytical column 4 is drained through the ports 2n, 2m, the thin tube 56', the ports 1j, 1k, the thin tube 55'.

The solution 6' of the mobile phase B is transmitted by the pump 7' and is divided into two paths at the tee 8'. The solution 6' of the mobile phase B in one of the two paths is transmitted through a path of the ports 2q, 2p, and the thin tube 66'. The solution 6' in other of the paths is transmitted through the branched resistance column 19' and the two branched solutions 6' are confluenced at the tee 18'. The confluenced solution 6' is wasted through the drain DR 1 to the outside through a path of the thin tube 59', and the ports 1g, 1f.

The solution 11' of the mobile phase C is transmitted by the pump 10 and branched at the tee 20'. One of the branched solution 11 of the mobile phase C flows into the trapping column 12' through a path of the thin tube 70', ports 2f, 2e, the thin tube 54', the ports 1l, 1m, the thin tube 53', the ports 1d, 1e, and the thin tube 61'.

Whereby, the analytical components trapped in the analytical column 12' is eluted by the back-flush. The eluate containing the analytical components introduced into the ion source 9' of the MS through a path of the thin tube 58', ports 1h 1i, the thin tube 57', the ports 2a, 2b and the thin tube 73', and provide the mass spectrum.

Other of the branched solution 11' of the mobile phase C washes the sample injection port 3 through a path of the thin tube 52', the ports 1n, 1p, the thin tube 51' and wasted through the drain DR 3 to the outside through a path of the thin tube 64, the ports 1b, 1c, the thin tube 62' and the ports 2c, 2d.

In the third analytical mode, the components of interest trapped in the column are eluted by the back-flush and provide the mass spectrum. Other flow paths are washed and the eluate A from the analytical column 4 is wasted to the outside.

Figure 42:
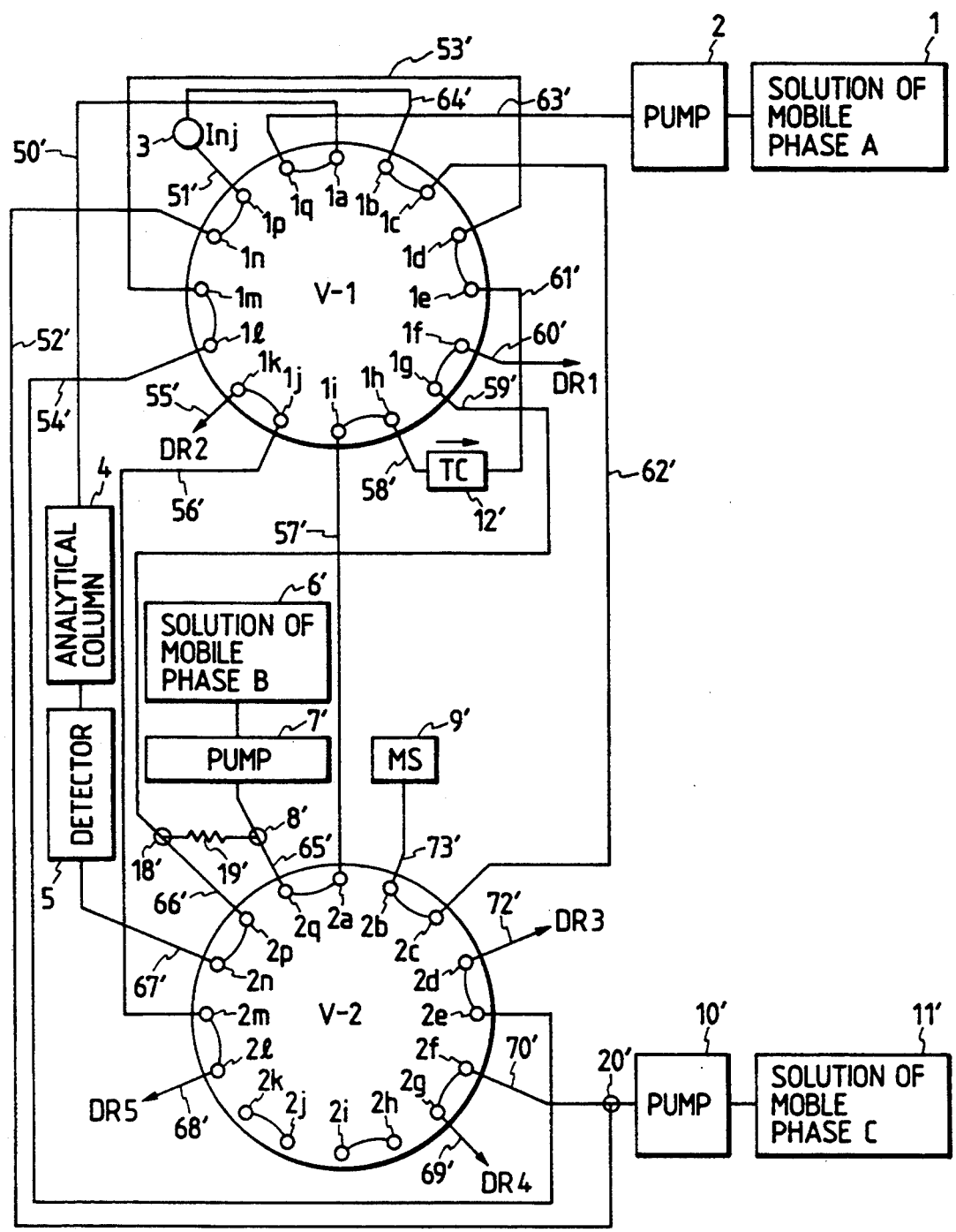
FIG. 42 is a further embodiment of a fourth analytical mode of a LC/MS analytical system of the present invention.

FIG. 42 shows a system corresponding to the fourth analytical mode. The solution 1 of the mobile phase A is transmitted to the analytical column 4 by the pump 2 through a path of the thin tube 63', the ports 1q, 1a, and the thin tube 50'. Then, the solution 1 of the mobile phase A is wasted through the drain DR 1 through a flow path of the detector 5, the thin tube 67', the ports 2n, 2p, the thin tube 66', the T shape tube 18', the thin tube 59', and the ports 1g, 1f.

The solution 11' of the mobile phase C is transmitted to the tee 20' so as to be divided into two branched flows. The solution 11' of one of the branched flows is wasted through the drain DR 4 through a path of the thin tube 70', the ports 2f, 2g, and the thin tube 69'. The solution 11' of other of the branched flows is transmitted to the ion source 9' of the MS through a path of the change-over valve V-1, the ports 1n, 1p, the thin tube 51', the sample injection port 3, the thin tube 64', the ports 1b, 1c, the thin tube 62', the ports 2c, 2b, and the thin tube 73'.

The solution 6' of the mobile phase B is transmitted to the trapping column 12' by the pump 7' through a path of the ports 2q, 2a the thin tube 57' the ports 1i, 1h, and the thin tube 58'. The solution of the mobile phase B washes the trapping column 12' by flowing as shown with an arrow in the figure.

After washing the column 12', the eluate D is wasted through the drain DR 3 through a path of the thin tube 61', the ports 1e, 1d, the thin tube 53', the ports 1m, 1l, the thin tube 54', the ports 2e, 2d, and the thin tube 72'.

In the fourth analytical mode, the trapping column 12' is washed with the solution of the mobile phase B and the ion source of the MS is washed with the solution 11 of the mobile phase C. The sample injection port 3 is independently provided in the flow path of the washing solution 11' of the mobile phase C which is separated from the analytical column 4, thereby it becomes possible to provide the FIA in the ion source 9' of the MS in the fourth analytical mode. At this time, the analytical column 4 is washing with the solution 1 of the mobile phase A.

In the examples stated above, it becomes possible to obtain the desalting of the sample solution, the direct analyzing by the LC/MS, the removal of the components of non-interest, and the FIA by changing over the four modes of the first, second, third and fourth analytical modes.

EXAMPLE 11

Figure 43:
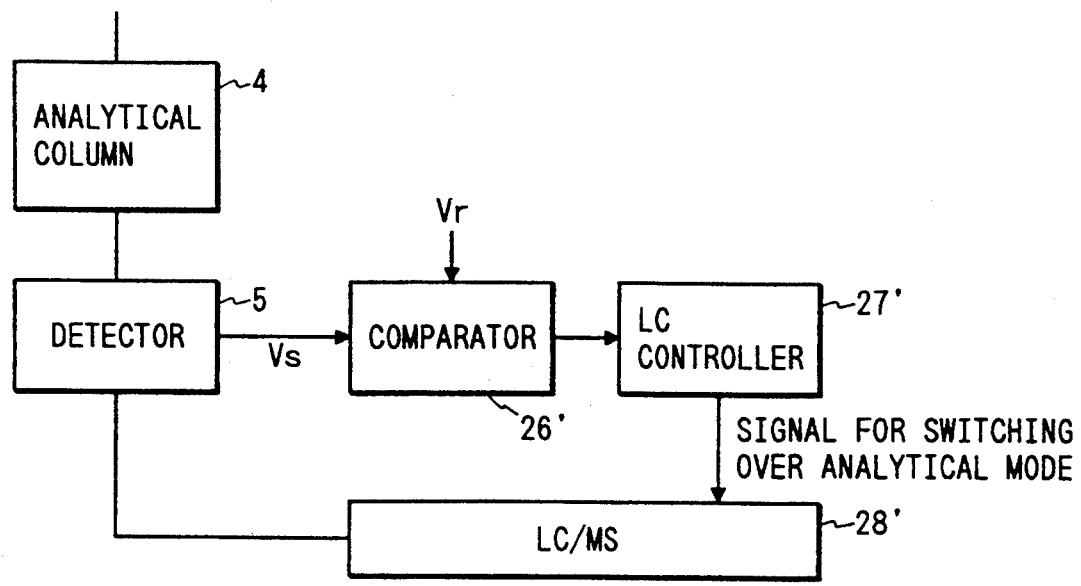
FIG. 43 is a block diagram of LC/MS of another further another embodiment of the present invention.
Figure 44:
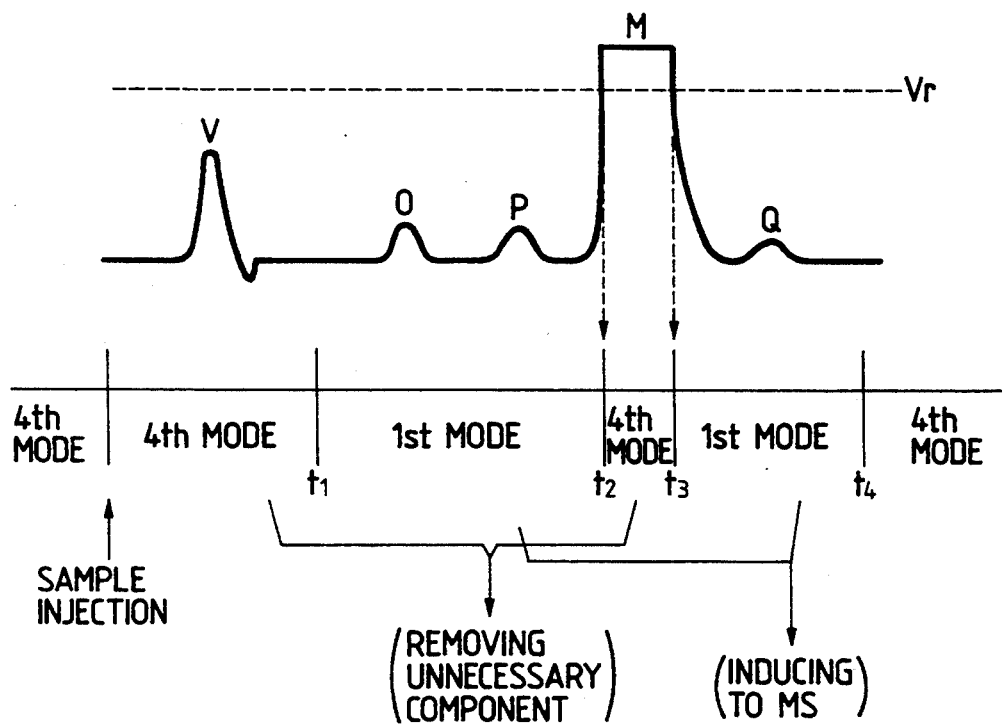
FIG. 44 is a explanatory view of analytical modes for automatically removing high concentration components.

FIG. 43 is a block diagram of LC/MS in another further embodiment of the present invention and FIG. 44 is a explanatory view of analytical modes for automatically removing high concentration components in the LC/MS shown in FIG. 43.

In FIG. 43, numeral 26' means a comparator; 27' a LC controller; 28' a LC/MS. In FIG. 44, code O, P, Q means components of interest; M main component; V component eluted by the void volume; and the codes M, V the components of non-interest.

As shown in FIG. 43, the detector 5 is disposed in a rear position of the analytical column 4 and monitors the components eluted from the analytical column 4. The comparator 26' always compares an output voltage Vs of the detector 5 with a comparing voltage Vr of the comparator.

When the components having high concentration are detected, the output voltage Vs from the detector 5 becomes higher than the comparing voltage Vr, and the LC controller 27' outputs an order signal to the LC/MS 28' so as to change into the fourth analytical mode.

After finishing the elution of the components having high concentration, the voltage Vs from the detector 5 becomes lower than the voltage Vr, and then the LC controller 27' give the order signal to the LC/MS 28' so as to return to the former mode.

Using FIG. 44, how to change the analytical modes will be explained.

After setting the fourth analytical mode, the sample solution is injected. The component V eluted by the void volume is wasted to the outside. At time t1, the first analytical mode is performed so as to measure the components of interest O, P.

When the component M having high concentration is eluted and the output voltage Vs from the detector 5 becomes higher than the voltage Vr of the comparator, the first analytical mode is automatically changed into the fourth analytical mode at time t2. In the case the output voltage Vs becomes lower than the comparing voltage Vr at the time t3, the analytical mode returns to the first analytical mode.

In this first analytical mode, the eluted component of analyte Q may be measured after the main component M is eluted. At time t4, the measuring by the LC/MS is finished and the analytical mode is changed into the fourth analytical mode in order to perform a next analytical process. In the example as above, the trapping time of the components having the high concentration is not known, it becomes possible to remove the component having the high concentration and to prevent their carry-over.

EXPERIMENTAL EXAMPLES

The experimental examples by using above examples will be explained hereinafter.

The sample used as the example is an anti-fungal having a molecular weight of 331. The system used for the sample is the example 9 as shown in FIG. 35 and the analytical conditions are shown in a following table.

| Item | Conditions |
| --- | --- |
| analytical column | 6 × 150 mm ODS column |
| ion source 9' | atmospheric pressure chemical ionization |
| trapping column 12 | 4 × 30 mm ODS.column |
| detector 5 | UV monitor |
| detecting wave length | 260 |

The sample is dissolved with the solution of the mobile phase for analysis and the concentration thereof is 100 pl/ml. The sample solution of 100 pl/ml (injection volume thereof: 10 μg) is injected from the sample injection port 3.

Figure 45:
FIG. 45 shows a liquid chromatogram of first experimental example.
Figure 46:
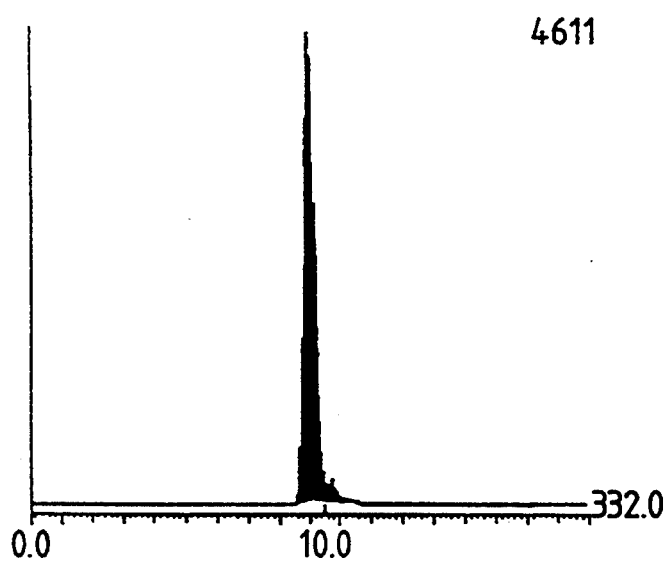
FIG. 46 shows a mass chromatogram of first experimental example.
Figure 47:
FIG. 47 shows a liquid chromatogram of second experimental example.
Figure 48:
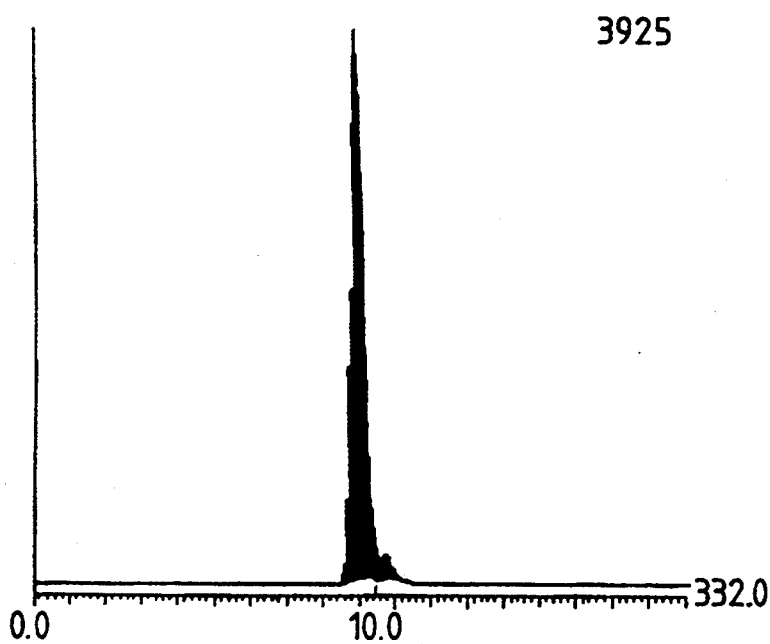
FIG. 48 shows a mass chromatogram of second experimental example.
Figure 49:
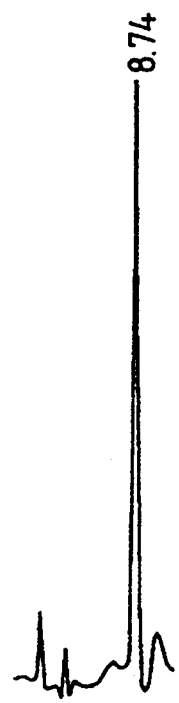
FIG. 49 shows a liquid chromatogram of third experimental example.
Figure 50:
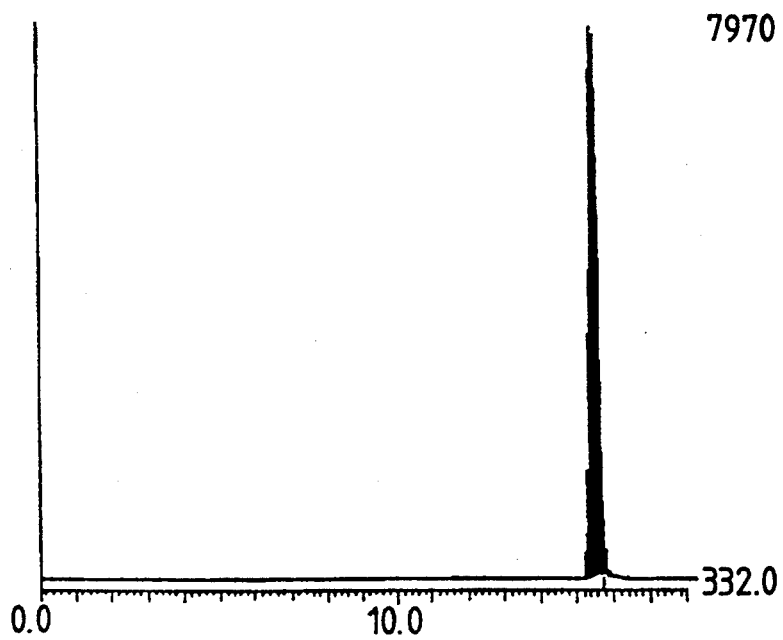
FIG. 50 shows a mass chromatogram of third experimental example.
Figure 51:
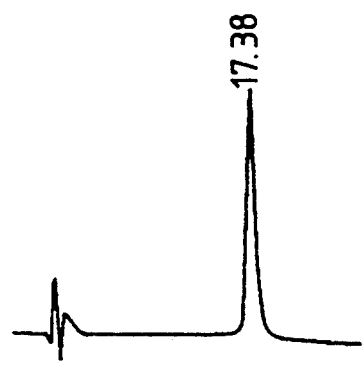
FIG. 51 shows a liquid chromatogram of fourth experimental example.
Figure 52:
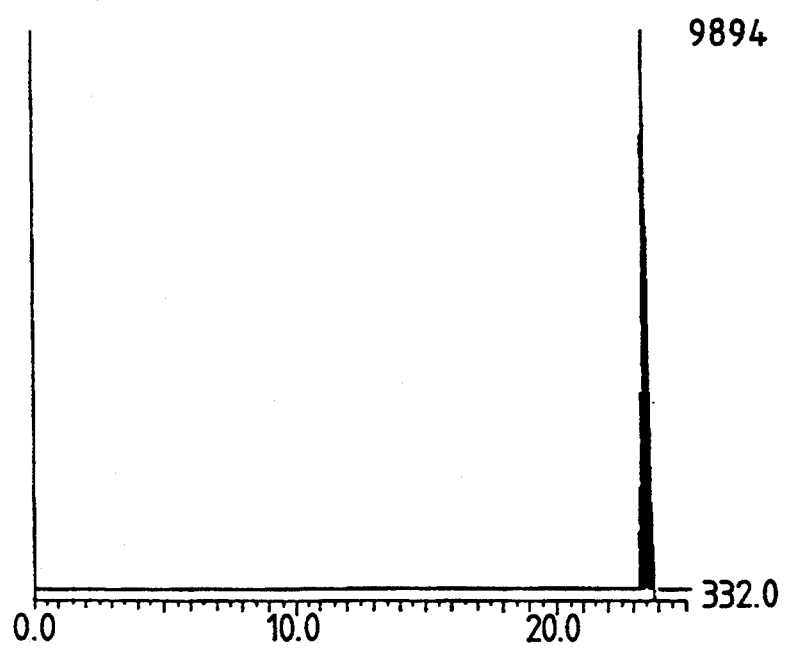
FIG. 52 shows a mass chromatogram of fourth experimental example.

FIG. 45 shows a liquid chromatogram of first experimental example. FIG. 46 shows a mass chromatogram of first experimental example. FIG. 47 shows a liquid chromatogram of second experimental example. FIG. 48 shows a mass chromatogram of second experimental example. FIG. 49 shows a liquid chromatogram of third experimental example. FIG. 50 shows a mass chromatogram of third experimental example. FIG. 51 shows a liquid chromatogram of fourth experimental example. FIG. 52 shows a mass chromatogram of fourth experimental example.

EXPERIMENTAL EXAMPLE 1

FIGS. 45, 46 show the example in the case where all of the eluate in the analytical system relating to the volatile solution of the mobile phase is introduced to the MS.

The solution 1 of the mobile phase A is a solution mixed with acetonitorile and aqueous solution 0.01M of ammonium acetate which are mixed with a ratio 5:1.

The liquid chromatogram shown in FIG. 45 is outputted from the detector 5 and the analyte are eluted at the time 8.78 minutes. FIG. 46 shows a mass chromatogram of pseudo-molecular ion (M+H) of m/z 332 detected by the LC/MS. This analysis of the component of interest is performed with the first analytical mode. That is, all of the eluate by the LC is introduced to ion source 9' of the MS.

In the FIG. 46, numerals 4611 on upper right handside of the mass chromatogram means a height of the peak, which corresponds to a maximum current (mA) when the pseudo-molecular ion of m/z 332 is detected.

EXPERIMENTAL EXAMPLE 2

FIGS. 47, 48 show the same chromatogram as in the FIGS. 45, 46 and show experimental examples of the component of interest introduced into the MS by removing the components eluted by the void volume.

FIG. 47 shows a liquid chromatogram monitored by the detector 5, and the component of analyte is eluted at the time 8.72 minutes and the components of noninterest are eluted by the void volume at the time 3.46 minutes.

The LC analysis is performed by injecting the sample after the fourth analytical mode is set. The fourth analytical mode is held until the time 7 minutes in order to remove the components of the void volume which appeared at three minutes after injection. After 7 minutes passed, the analytical mode is changed to the first analytical mode and the eluate A from the LC is introduced to the ion source 9' of the MS.

As explained above, the salt etc. which is eluted by the void volume are wasted to the outside and the components of interest are introduced to the ion source 9' of the MS.

The FIG. 48 shows a mass chromatogram by the pseudo-molecular ion of m/z 332 and the retention time of the components of interest does not change if the valve is changed over.

EXPERIMENTAL EXAMPLE 3

FIGS. 49, 50 show the same chromatogram as in the experimental examples 1, 2 and show experimental examples of the components of interest trapped by the trapping column and introduced into the MS after removing the components eluted by the void volume.

In FIG. 49, the solution 1 of the mobile phase A is an aqueous solution of ammonium acetate and there is not any special necessity to desalt the component in the LC/MS.

The experimental data shown in FIG. 49 is provided in order to prove the functions of the system in the present invention.

The fourth analytical mode continues till 7 minutes and the eluate A is wasted to the outside, and simultaneously the pretreatment of the trapping column 12' is performed. The second analytical mode is performed from 7 minutes to 9.8 minutes and the components of interest from the analytical column 4 is trapped by the trapping column 12'. The fourth analytical mode is again performed from 9.8 minutes to 15 minutes, and the components of interest are desalted and the eluate A is wasted to the outside. After 15 minutes, the third analytical mode is performed, and the component of interest trapped in the trapping column 12' is eluted by the back-flush.

Here, the matter to which attention should be paid is that the height of the peaks detected by the LC/MS in the experimental examples 1, 2 as shown in FIGS. 46, 48 are respectively 4611 and 3925, and the peak in this experimental example is 7970. This data means that the peak of the components of interest eluted by the back-flush becomes more sharp than that of the components eluted from the analytical column 4 and the height of the peak becomes higher. It is very useful for measuring the components of interest having very low concentration as the sensitivity of the apparatus becomes higher. Such a system as above is applicable to the volatile solution of the mobile phase.

EXPERIMENT EXAMPLE 4

FIGS. 51, 52 show chromatogram when using the non-volatile solution of the mobile phase. The solution 1 of the mobile phase A is an aqueous solution of methanol and potassium dihydrogenphosphate 0.05M mixed with a ratio 35:65 and the flow rate thereof is 1.2 ml/min.

The solution 11 of the mobile phase C for eluting the components of interest trapped in the trapping column 12' is an aqueous solution of acetonitrile of 90%. The solution 6' of the mobile phase B for diluting is pure water.

The sample is dissolved by the solution 1 of the mobile phase A to a concentration of 100 μg/ml and the sample of 100 μl is injected. The analytical column is ODS 6×150 mm and the trapping column is ODS 4×30 mm.

A chromatogram by the LC as above is shown in FIG. 51 and the peak arises at 17.38 minutes under a condition as above.

The chromatogram by the desalting system in this experimental example is shown in FIG. 52.

The fourth analytical mode is performed just after injecting the sample solution until 16 minutes, and the eluate A from the analytical column A is wasted to the outside and the trapping column 12' is washed with the solution 6' of the mobile phase B, that is, the water. After 16 minutes, the second analytical mode is performed and the components of interest are trapped by the trapping column 12'.

At 18.4 minutes when the elution of the component of interest is finished, the fourth analytical mode is performed the component trapped in the column 12' is desalted by flowing the solution 6' of the mobile phase B, that is, the water. At 23 minutes, the third analytical mode is preformed and the components trapped in the trapping column 12' is eluted by the back-flush of the solution 11' of the mobile phase C and introduced to the MS.

In this case, the height of the peak in the mass chromatogram is 9894 and becomes very sharp in the same way as in the analysis of ammonium acetate solution. The peak height becomes more than twice of the peak height 4611 in the case of directly introducing the ammonium acetate solution to the MS in the experimental example 1.

The system explained in the experimental example 4 is applied to the LC/MS which use both of the nonvolatile buffer and the non-volatile salt and the sensitivity thereof is improved.

Further, every example and every experimental example are explained relating to the system which directly connects the LC and the MS by selecting the four modes of the first, second, third and fourth analytical modes which are performed by easily changing over the valves V-1, V-2, V-3 and connecting the flow paths 91', 92' depending on the signal from the LC controller 27'.

We claim:

1. An apparatus for directly connecting an analytical column and a mass spectrometer comprising,
   a fixed member having at least four holes therein, said holes respectively introduce washing solution, eluate eluted from the analytical column which contains a component of interest, desalting solution, and eluent for eluting the component, and
   a movable member having at least four tubes around an axis, said tubes being changeably connected to the four holes by rotating the movable member with respect to the axis, and mounting four trapping columns which are respectively connected to one ends of the four trapping columns, whereby said four trapping columns are respectively washed, trapped, desalted and eluted in parallel.

2. An apparatus as defined in claim 1, wherein said fixed member has further one hole connected to the mass spectrometer and three drain holes, which are changeably connected to the other ends of the four trapping columns in parallel by rotating the movable member with respect to the axis.

3. An apparatus as defined in claim 1, wherein more than five trapping columns are mounted on said moveable member, and at least two of the columns are changeably connected to the hole for sequentially introducing to the same column the washing solution, the eluate, the desalting solution and the eluent.

4. An apparatus as defined in claim 1, wherein said four holes are selectively connected to at least two of the trapping columns in parallel.

5. An apparatus as defined in claim 1, wherein
said movable member further has a bypass tube between the tubes connected to the trapping columns for bypassing a drain from the fixed member.

6. An apparatus as defined in claim 1, wherein
said movable member further has bypass tubes provided between the four respective tubes for bypassing to a drain from the fixed member.

7. An apparatus as defined in claim 1, wherein
the flow directions of the washing solution and the eluate in the trapping columns are respectively opposite to a flowing direction of the eluent in the trapping columns.

8. An apparatus as defined in claim 1, wherein
said fixed member consists of first fixed member having three holes for respectively introducing the washing solution, the eluate and the desalting solution, and second fixed member having the hole for introducing the eluent, and
said movable member is disposed between the first and the second fixed members.

9. An apparatus as defined in claim 8, wherein
said first fixed member has further one hole connected to the mass spectrometer and said second fixed member has three drain holes, said other one hole and said three drain holes are respectively and changeably connected to the other ends of the four trapping columns by rotating the movable member with respect to the axis.

10. An apparatus as defined in claim 8, wherein
said movable member is installed trapping columns more than five, and at least two of the columns are changeably connected to the hole for introducing the same one of the washing solution, the eluate, the desalting solution and the eluent.

11. An apparatus as defined in claim 8, wherein said four holes are selectively connected to at least two of the trapping columns in parallel.

12. An apparatus as defined in claim 8, wherein
said movable member further has a bypass tube between the tubes connected to the trapping columns for bypassing to a drain from the fixed member.

13. An apparatus as defined in claim 8, wherein said movable member further has bypass tubes provided between the four respective tubes for bypassing a drain from the fixed member.

14. An apparatus as defined in claim 8, wherein
the flow directions of the washing solution and the eluate in the trapping columns are respectively opposite to a flowing direction of the eluent in the trapping columns.

15. A controlling method for directly connecting an analytical column and a mass spectrometer by using a trapping column and a plurality of change-over valves, comprising the steps of controlling the change-over valves with at least four modes of
   (1) first mode for washing the trapping column and introducing eluate from the analytical column to the mass spectrometer,
   (2) second mode for trapping a component contained in eluate eluted from the analytical column with the trapping column and washing the mass spectrometer, (3) third mode for eluting the component trapped in the trapping column and introducing the component to the mass spectrometer, and (4) fourth mode for washing the trapping column and the mass spectrometer, and for draining the eluate from analytical column.

16. A controlling method as defined in claim 15, wherein the flow directions of the washing solution in the trappping column and of the eluate from the analytical column in the trapping column are respectively opposite to a flowing direction of the eluent in the trapping columns.

17. A controlling method as defined in claim 15, wherein said first, second, third and fourth modes are respectively and independently selected by changing over the valves.

18. An apparatus for directly connecting an analytical column and a mass spectrometer, comprising:
a trapping column,
a plurality of change-over valves connected to the analytical column and the trapping column, and
a controller for controlling said change-over valves, wherein said trapping column being controlled by following modes;

(1) first mode for washing the trapping column and introducing eluate from the analytical column to the mass spectrometer, (2) second mode for trapping a component contained in eluate eluted from the analytical column by the trapping column and washing the mass spectrometer, (3) third mode for eluting the component trapped in the trapping column and introducing the component to the mass spectrometer, and (4) fourth mode for washing the trapping columns and the mass spectrometer, and for draining the eluate from analytical column.

19. An apparatus as defined in claim 18, wherein the flow directions of the washing solution in the trap columns and of the eluate from the analytical column in the trapping column are respectively opposite to a flowing direction of the eluent in the trapping column.

20. An apparatus as defined in claim 18, wherein said first, second, third and fourth modes are respectively and independently selected by changing over the valves.

* * * * *